United States Patent
Yost et al.

(10) Patent No.: US 10,857,201 B2
(45) Date of Patent: Dec. 8, 2020

(54) NNIF AND NNIF-RELATED PEPTIDES AND RELATED METHODS

(71) Applicant: UNIVERSITY OF UTAH RESEARCH FOUNDATION, Salt Lake City, UT (US)

(72) Inventors: Christian Con Yost, Salt Lake City, UT (US); Guy A. Zimmerman, Salt Lake City, UT (US); Andrew S. Weyrich, Salt Lake City, UT (US); Joshua Schiffman, Salt Lake City, UT (US)

(73) Assignee: Ballard Spahr LLP, Salt Lake City, UT (US)

( * ) Notice: Subject to any disclaimer, the term of this patent is extended or adjusted under 35 U.S.C. 154(b) by 0 days.

(21) Appl. No.: 16/328,697

(22) PCT Filed: Sep. 5, 2017

(86) PCT No.: PCT/US2017/050072
§ 371 (c)(1),
(2) Date: Feb. 26, 2019

(87) PCT Pub. No.: WO2018/045371
PCT Pub. Date: Mar. 8, 2018

(65) Prior Publication Data
US 2019/0201487 A1      Jul. 4, 2019

Related U.S. Application Data

(60) Provisional application No. 62/383,243, filed on Sep. 2, 2016, provisional application No. 62/492,019, filed on Apr. 28, 2017.

(51) Int. Cl.
*A61K 38/00*      (2006.01)
*A61K 38/17*      (2006.01)
*C07K 14/47*      (2006.01)
*A61P 29/00*      (2006.01)
*A61P 35/04*      (2006.01)

(52) U.S. Cl.
CPC .......... *A61K 38/1709* (2013.01); *A61P 29/00* (2018.01); *A61P 35/04* (2018.01); *C07K 14/47* (2013.01); *C07K 14/4703* (2013.01)

(58) Field of Classification Search
None
See application file for complete search history.

(56) References Cited

U.S. PATENT DOCUMENTS

2016/0194365 A1* 7/2016 Yost .................. A61K 38/1709
                                                          514/1.4

OTHER PUBLICATIONS

Olsson et al. Front Immunol. 2016; 7: 373).*
Adkins B., et al., "Neonatal immunology: responses to pathogenic microorganisms and epigenetics reveal an "immunodiverse" developmental state" *Immunologic research*. 2013;57 (1-3):246-57.
Araujo CV, et al., "A PPARy Agonist Enhances Bacterial Clearance Through Neutrophil Extracellular Trap Formation and Improves Survival In Sepsis" *Shock*. 2016;45 (4):393-403.
Arck PC, et al., "Fetomaternal immune cross-talk and its consequences for maternal and offspring's health" *Nature medicine*. 2013;19 (5):548-56.
Branzk N, et al., "Molecular mechanisms regulating NETosis in infection and disease" Semin Immunopathol. 2013;35 (4):513-30.
Brinkmann V, et al., "Neutrophil extracellular traps: is immunity the second function of chromatin?" *J Cell Biol*. 2012;198 (5):773-83.
Brinkmann V, et al., "Neutrophil extracellular traps kill bacteria" *Science*. 2004;303 (5663):1532-5.
Castellucci M, et al., "Immunohistochemical localization of serine-protease inhibitors in the human placenta Immunohistochemical localization of serine-protease inhibitors in the human placenta " *Cell and tissue research*. 1994;278 (2):283-9.
Caudrillier A, et al., "Platelets induce neutrophil extracellular traps in transfusion-related acute lung injury" *J Clin Invest*. 2012;122 (7):2661-71.
Cercek L, et al., Cancer-associated SCM-recognition, immunedefense suppression, and serine protease protection peptide. Part I. Isolation, amino acid sequence, homology, and origin: *Cancer Detect Prev*. 1992;16 (5-6):305-19.
Cercek L, et al., "Cancer-associated SCM-recognition, immunedefense suppression, and serine protease protection peptide. Part II. Immunedefense suppressive effects of the CRISPPs peptide" *Cancer Detect Prev*. 1993;17 (3):433-45.
Cercek L, et al., "Cancer-associated SCM-recognition, immunedefense suppression, and serine protease protection peptide. Part III. CRISPP peptide protection of serine proteases against inhibition" *Cancer Detect Prev*. 1993;17 (3):447-54.
Cheung R, et al. "Activation of MDL-1 (CLEC5A) on immature myeloid cells triggers lethal shock in mice" *J Clin Invest*. 2011;121 (11):4446-61.
Clark Sr, et al., "Platelet TLR4 activates neutrophil extracellular traps to ensnare bacteria in septic blood" *Nature medicine*. 2007;13 (4):463-9.
Cools-Lartigue J, et al., "Neutrophil extracellular traps sequester circulating tumor cells and promote metastasis" *J Clin Invest*. 2013;123 (8):3446-58.
Czaikoski PG, et al., "Neutrophil Extracellular Traps Induce Organ Damage during Experimental and Clinical Sepsis" *PloS one*. 2016;11 (2):e0148142.
Deshmukh HS, et al., "The microbiota regulates neutrophil homeostasis and host resistance to *Escherichia coli* K1 sepsis in neonatal mice" *Nat Med*. 2014;20 (5):524-30.
Dowling DJ, et al., "Ontogeny of early life immunity" *Trends in immunology*. 2014;35 (7):299310.

(Continued)

Primary Examiner — Jeanette M Lieb
(74) Attorney, Agent, or Firm — Ballard Spahr LLP

(57) ABSTRACT

Neonatal NET-Inhibitory Factor (nNIF) and nNIF-Related Peptides (NRPs) are provided. Methods for the treatment of and prophylaxis against inflammatory disorders and cancer are also provided. Additionally, methods for the inhibition of metastasis in patients having cancer are provided. The methods can include administering nNIF and/or a NRP to patients having, or at risk of developing, an inflammatory disorder or a cancer.

15 Claims, 14 Drawing Sheets

Specification includes a Sequence Listing.

(56) References Cited

OTHER PUBLICATIONS

Elahi S, et al., "Immunosuppressive CD71+ erythroid cells compromise neonatal host defence against infection" *Nature*. 2013;504 (7478):158-62.
Farley K, et al., "A serpinB1 regulatory mechanism is essential for restricting neutrophil extracellular trap generation" *Journal of immunology*. 2012;189 (9):4574-81.
Frenzel E, et al., "Does augmentation with alpha1-antitrypsin affect neutrophil extracellular traps formation?" *Int J Biol Sci*. 2012;8 (7):1023-5.
Frochaux V, et al., "Alpha-1-antitrypsin: a novel human high temperature requirement protease A1 (HTRA1) substrate in human placental tissue" *PloS one*. 2014;9 (10):e109483.
Fuchs TA, et al., "Novel cell death program leads to neutrophil extracellular traps" *J Cell Biol*. 2007;176 (2):231-41.
Gladwin MT, et al., "Erythroid DAMPs drive inflammation in SCD" *Blood*. 2014;123 (24):3689-90.
Gupta AK, et al., "Induction of neutrophil extracellular DNA lattices by placental microparticles and IL-8 and their presence in preeclampsia" *Hum Immunol*. 2005;66 (11):1146-54.
Hubbard WJ, et al., "Cecal Ligation and Puncture" *Shock*. 2005;24 Suppl 1 (52-7).
Jenne CN, et al. "Neutrophils recruited to sites of infection protect from virus challenge by releasing neutrophil extracellular traps" *Cell host & microbe*. 2013;13 (2):169-80.
Jost T, et al., "New insights in gut microbiota establishment in healthy breast fed neonates" *PloS one*. 2012;7 (8):e44595.
Kolaczkowska E, et al., "Molecular mechanisms of NET formation and degradation revealed by intravital imaging in the liver vasculature" *Nature communications*. 2015;6 (6673).
Levy O., "Innate immunity of the newborn: basic mechanisms and clinical correlates" *Nat Rev lmmunol*. 2007;7 (5):379-90).
Lewis HD, et al., "Inhibition of PAD4 activity is sufficient to disrupt mouse and human NET formation " *Nature chemical biology*. 2015.
Lood C, et al., "Neutrophil extracellular traps enriched in oxidized mitochondrial DNA are interferogenic and contribute to lupus-like disease" *Nature medicine*. 2016;22 (2):146-53.
Li P, et al., "PAD4 is essential for antibacterial innate immunity mediated by neutrophil extracellular traps" *J Exp Med*. 2010;207 (9):1853-62.
McDonald B, et al., "Intravascular neutrophil extracellular traps capture bacteria from the bloodstream during sepsis" *Cell host & microbe*. 2012;12 (3):32433.
McInturff AM, et al., "Mammalian target of rapamycin regulates neutrophil extracellular trap formation via induction of hypoxia-inducible factor 1 α" *Blood*. 2012;120 (15):3118-25.
Medzhitov R., "Origin and physiological roles of inflammation" *Nature*. 2008;454 (7203):428 35.
Nathan C., "Neutrophils and immunity: challenges and opportunities" *Nat Rev lmmunol*. 2006;6 (3):173-82.
Nathan C., "Points of control in inflammation" *Nature*. 2002;420 (6917):846-52.
Niemann MA, et al., "Inhibition of human serine proteases by SPAAT, the C-terminal 44-residue peptide from alpha1-antitrypsin" *Biochim Biophys Acta*. 1997;1340 (1):12330.
Niemann MA, et al., "Binding of SPAAT, the 44-residue C-terminal peptide of alpha 1-antitrypsin, to proteins of the extracellular matrix" *Journal of cellular biochemistry*. 1997;66 (3):346-57.
Niemann MA, et al., "Isolation and serine protease inhibitory activity of the 44-residue, C-terminal fragment of alpha 1-antitrypsin from human placenta" *Matrix*. 1992;12 (3):233-41.
Palmer C, et al., "Development of the human infant intestinal microbiota" *PLoS biology*. 2007;5 (7):e177.
Papayannopoulos V, et al., "Neutrophil elastase and myeloperoxidase regulate the formation of neutrophil extracellular traps" *J Cell Biol*. 2010;191 (3):677-91.
Pei D, et al., "Hydrolytic inactivation of a breast carcinoma cell-derived serpin by human stromelysin-3" *J Biol Chem*. 1994;269 (41):25849-55.
Pilsczek FH, et al., "A novel mechanism of rapid nuclear neutrophil extracellular trap formation in response to *Staphylococcus aureus*" *Journal of immunology*. 2010;185 (12):7413-25.
Raftery MJ, et al. "β2 integrin mediates hantavirus-induced release of neutrophil extracellular traps" *J Exp Med*. 2014;211 (7):1485-9743-45.
Saffarzadeh M, "Fighting against the dark side of neutrophil extracellular traps in disease: manoeuvres for host protection" et al., *Curr Opin Hematol*. 2013;20 (1):3-9.
Saitoh T, et al. "Neutrophil extracellular traps mediate a host defense response to human immunodeficiency virus-1" *Cell host & microbe*. 2012;12 (1):109-16.
Sangaletti S, et al., "Neutrophil extracellular traps mediate transfer of cytoplasmic neutrophil antigens to myeloid dendritic cells toward ANCA induction and associated autoimmunity" *Blood*. 2012;120 (15):3007-18.
Schauer C, et al., "Aggregated neutrophil extracellular traps limit inflammation by degrading cytokines and chemokines" *Nature medicine*. 2014;20 (5):511-7).
Sorensen OE, et al., "Neutrophil extracellular traps—the dark side of neutrophils" *Journal of clinical investigation*. 2016;126 (5):1612-20.
Tanaka K, et al., "In vivo characterization of neutrophil extracellular traps in various organs of a murine sepsis model" *PloS one*. 2014;9 (11):e111888.
Vieira-de-Abreu A, et al.,"Platelets: versatile effector cells in hemostasis, inflammation, and the immune continuum" *Semin lmmunopathol*. 2012;34 (1):5-30.
Wang Y, et al., "Histone hypercitrullination mediates chromatin decondensation and neutrophil extracellular trap formation" *J Cell Biol*. 2009;184 (2):205-13.
Wildhagen KC, et al., "Nonanticoagulant heparin prevents histone-mediated cytotoxicity in vitro and improves survival in sepsis" *Blood*. 2014;123 (7):1098101.
Yipp BG, et al., "NETosis: how vital is it?" *Blood*. 2013;122 (16):2784-94.
Yipp BG, et al., "Infection-induced NETosis is a dynamic process involving neutrophil multitasking in vivo" *Nature medicine*. 2012;18 (9):1386-93.
Yost CC, et al. "Impaired neutrophil extracellular trap (NET) formation: a novel innate immune deficiency of human neonates" *Blood*. 2009;113 (25):6419-27.
Zabieglo K, et al., "The inhibitory effect of secretory leukocyte protease inhibitor (SLPI) on formation of neutrophil extracellular traps" *Journal of leukocyte biology*. 2015;98 (1):99-106.
European Search Opinion and Supplementary Search Report dated Apr. 22, 2020 by the EP Patent Office for EP Application 17847679, filed Mar. 8, 2018 (Applicant—The University of Utah Research Foundation).
Chen G, et al., "Heme-induced neutrophil extracellular traps contribute to the pathogenesis of sickle cell disease" *Blood*. 2014;123 (24):3818-27.

\* cited by examiner

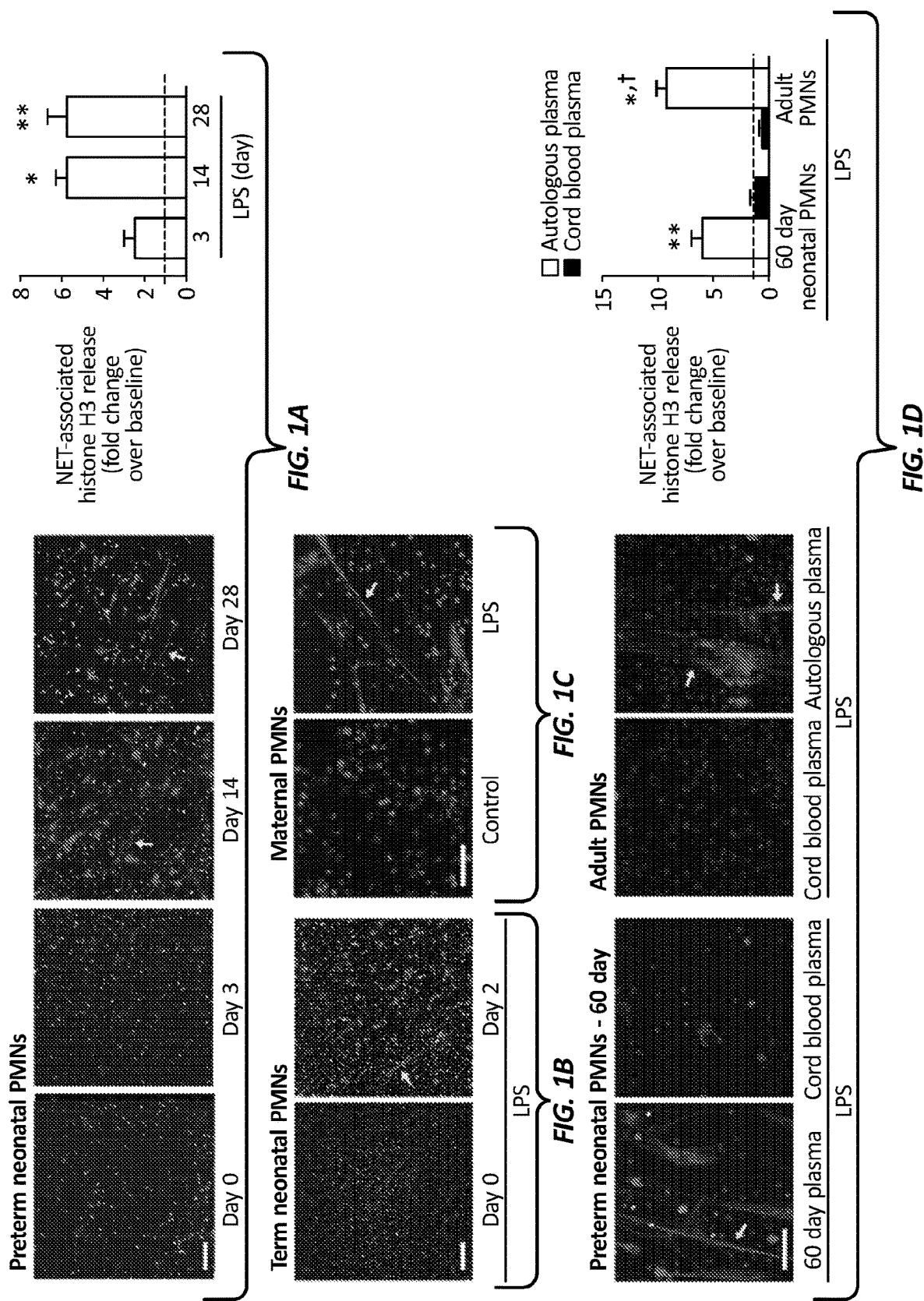

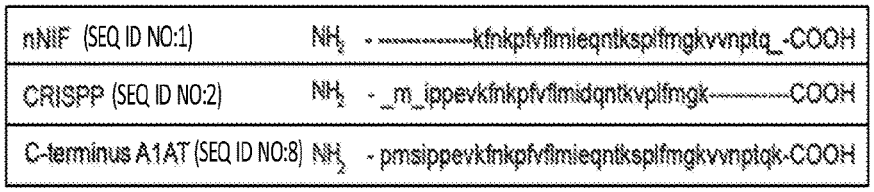
*FIG. 2A*
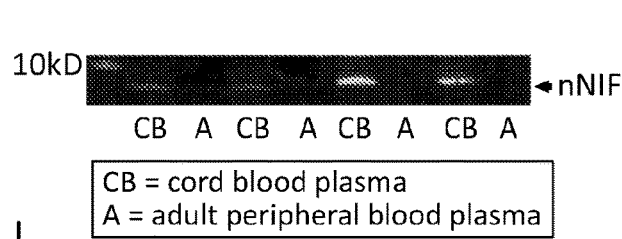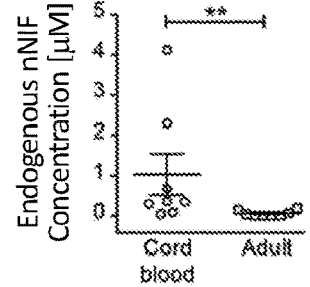
*FIG. 2B*
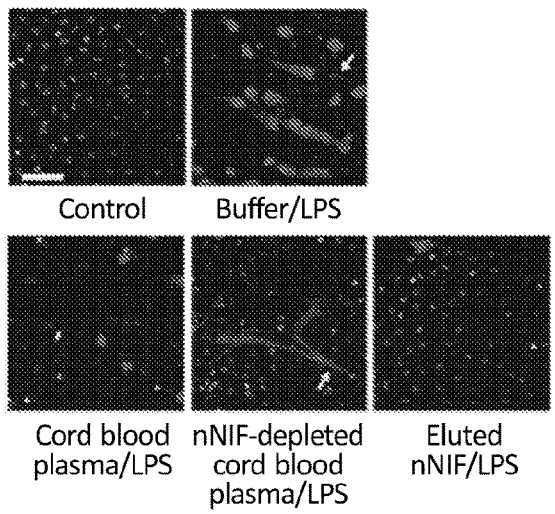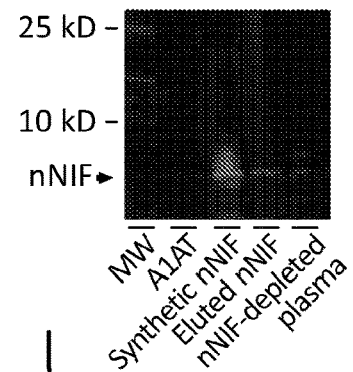
*FIG. 2C*      *FIG. 2D*
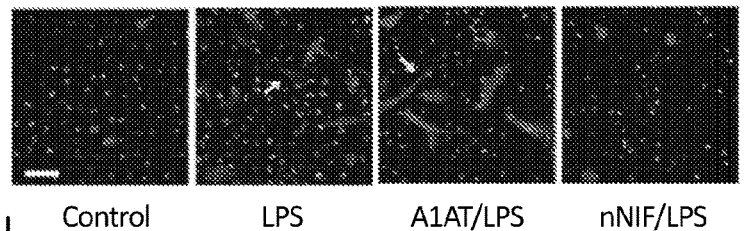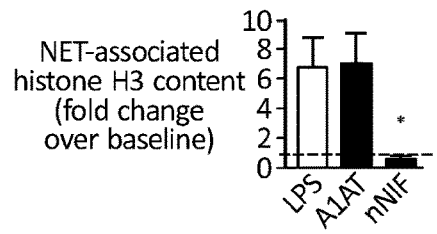
*FIG. 2E*

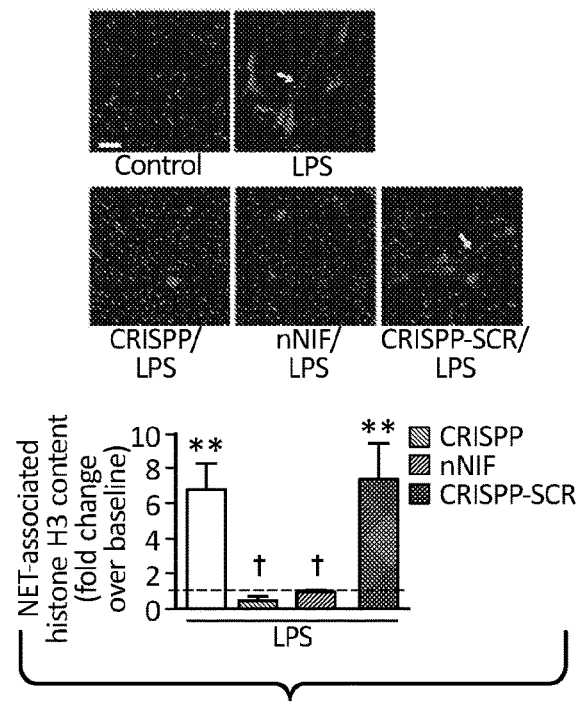
FIG. 3A
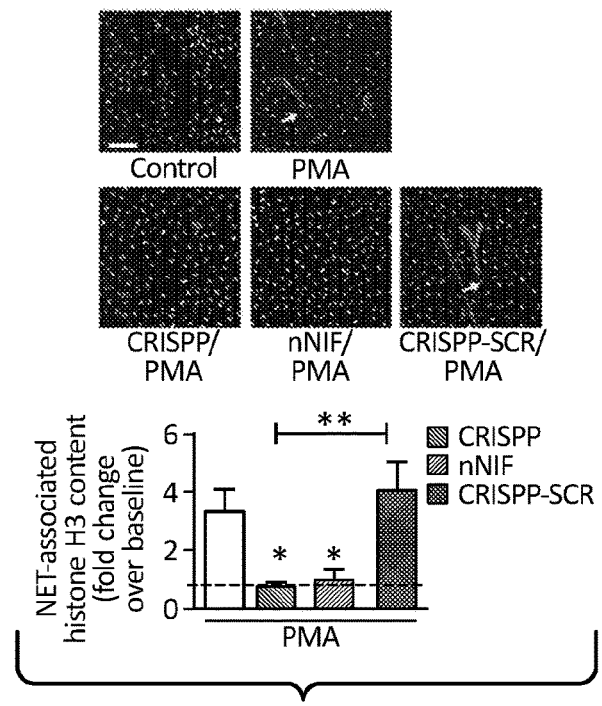
FIG. 3B
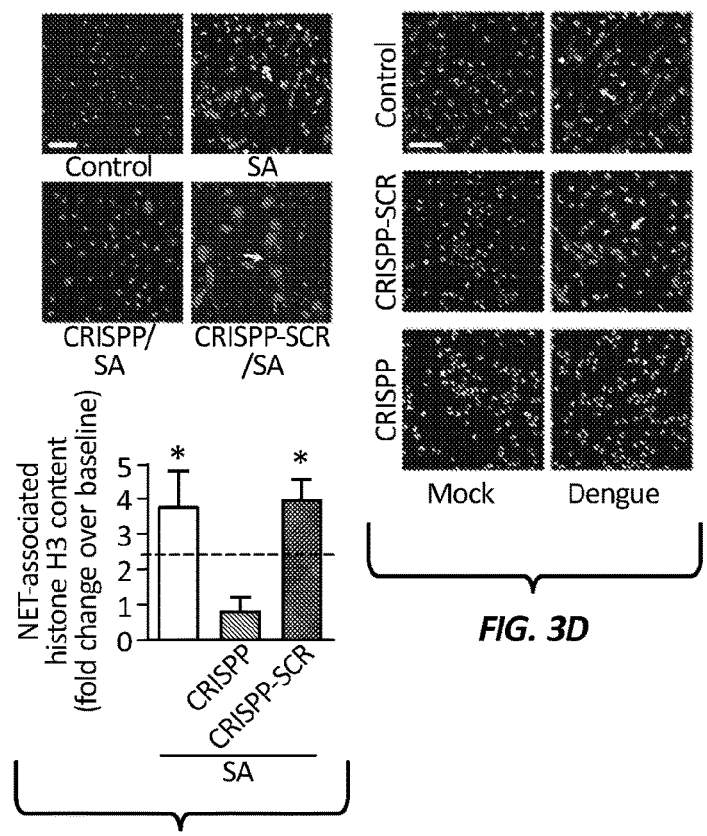
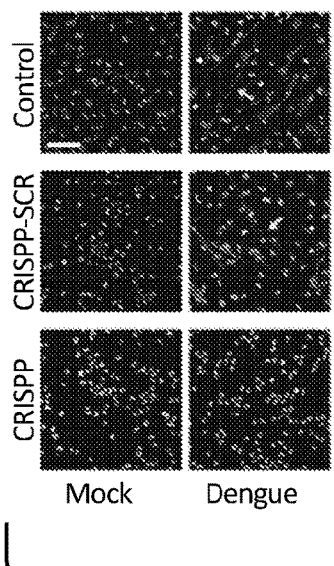
FIG. 3D
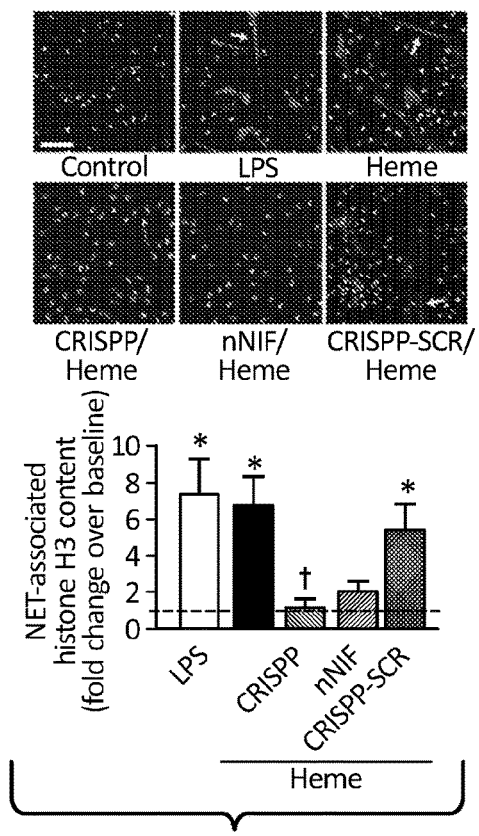
FIG. 3C
FIG. 3E

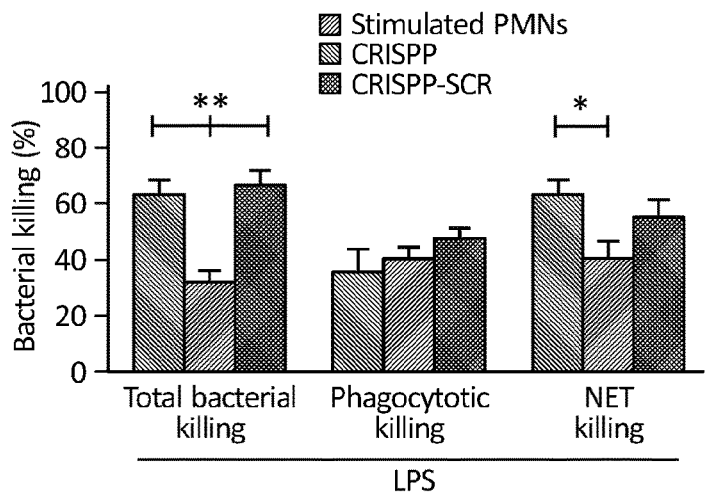
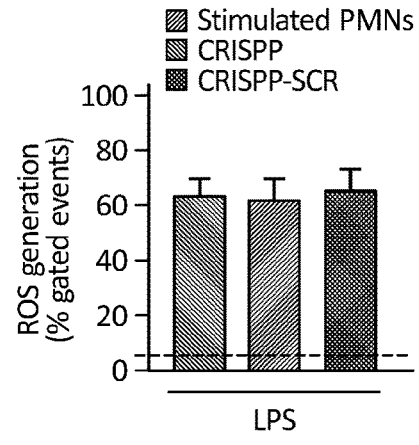
FIG. 6A
FIG. 6B
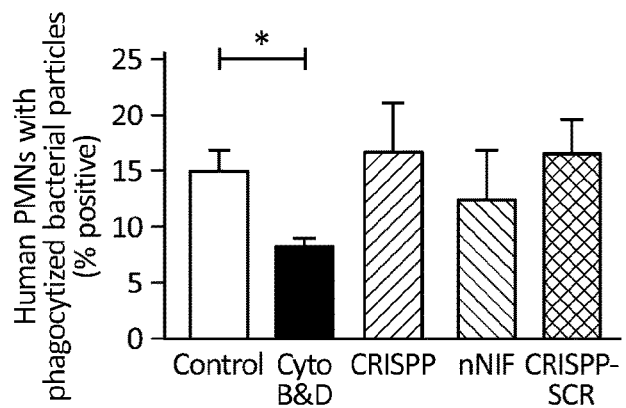
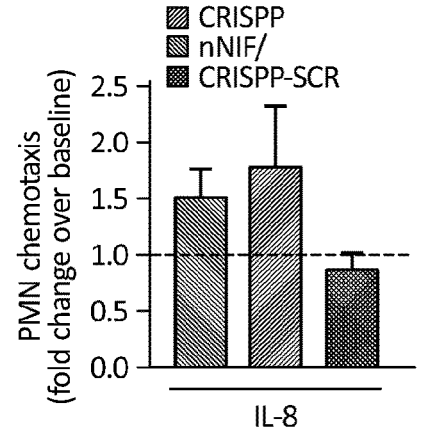
FIG. 6C
FIG. 6D
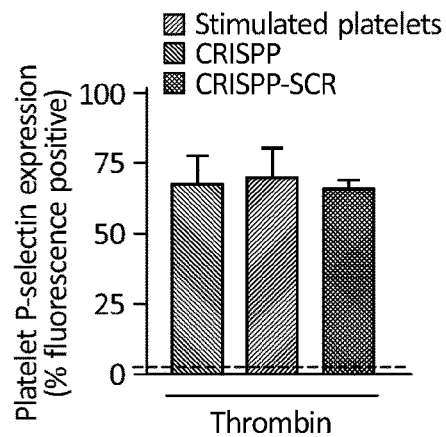
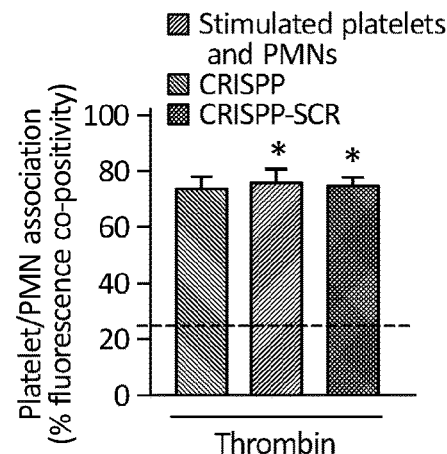
FIG. 6E
FIG. 6F

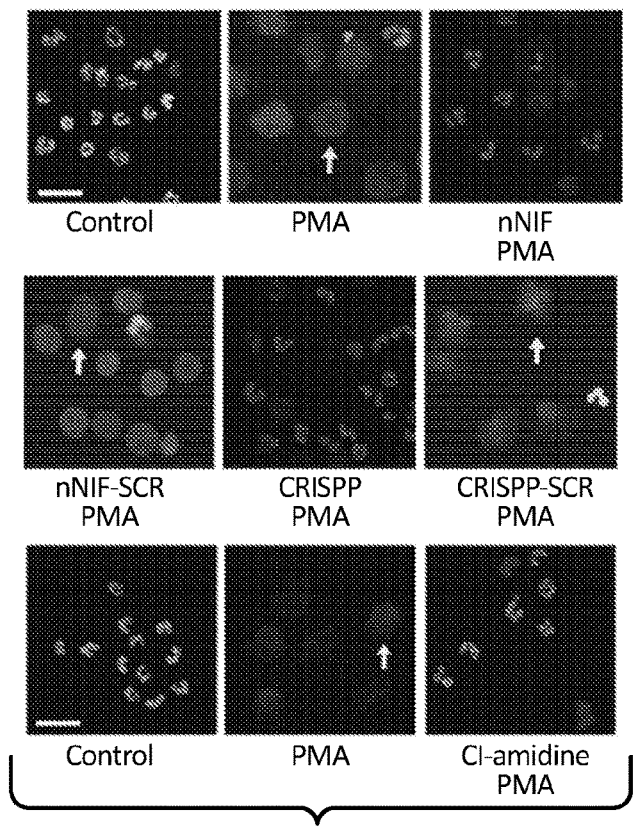
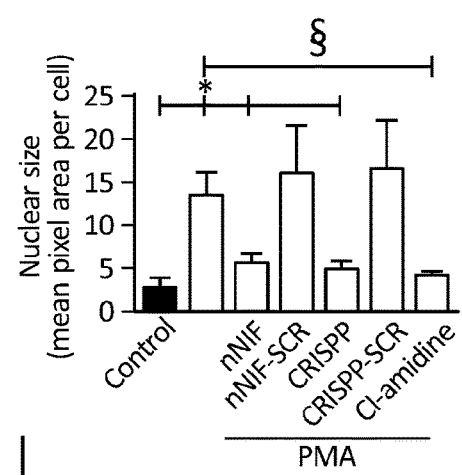
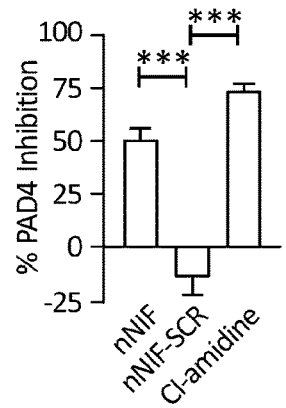
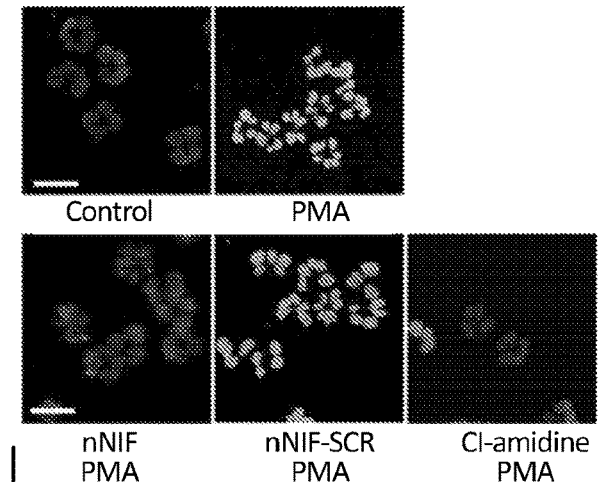
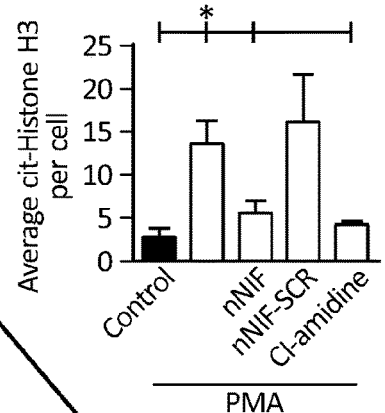
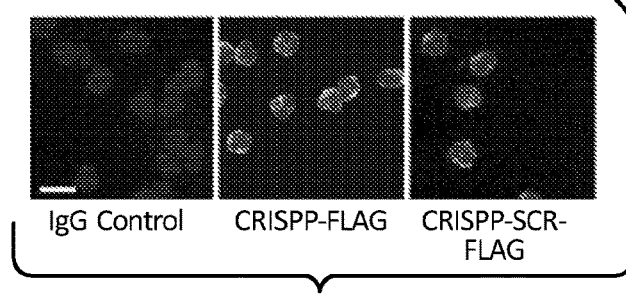
FIG. 7A
FIG. 7B
FIG. 7C
FIG. 7D
FIG. 7E

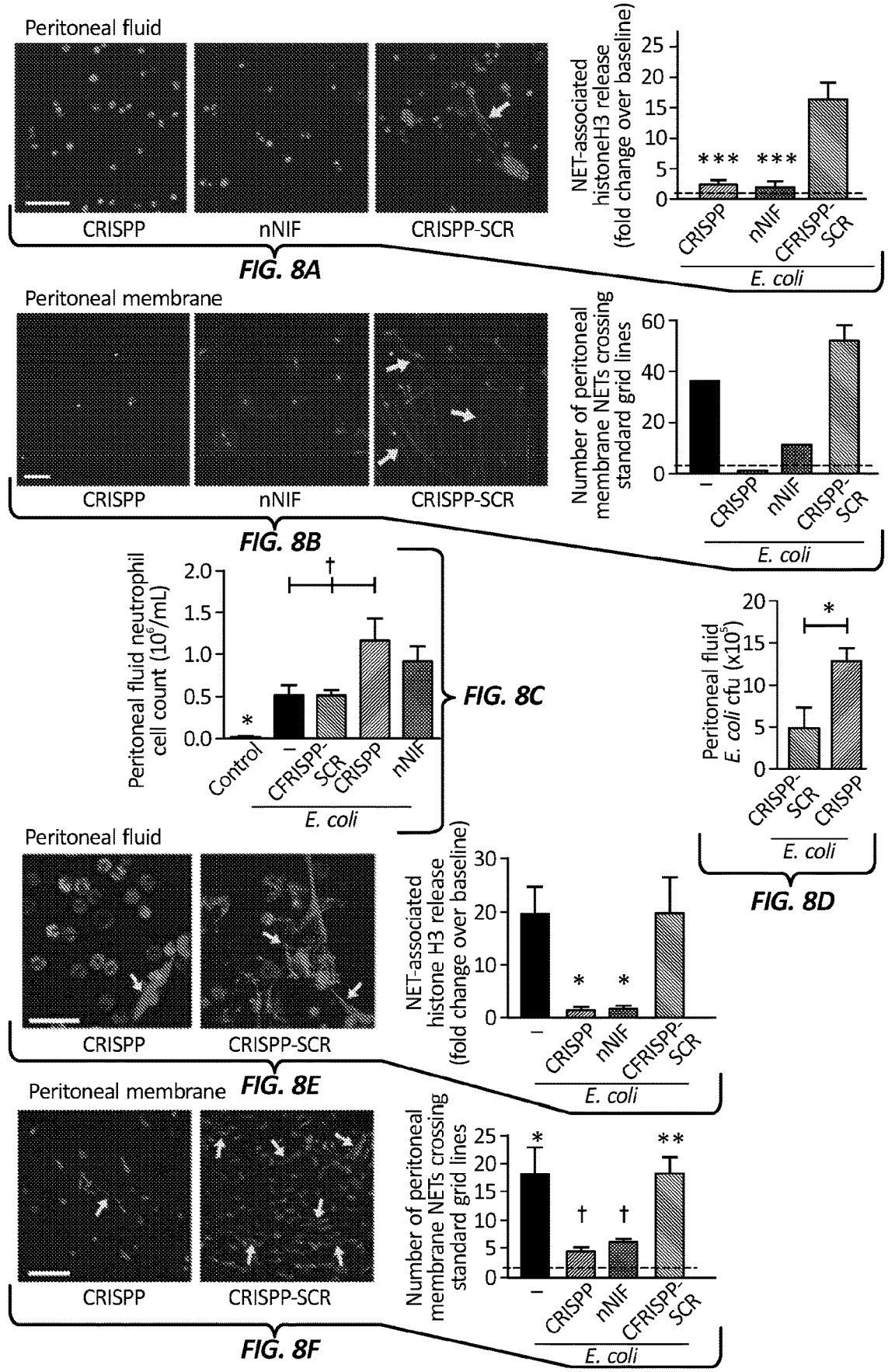

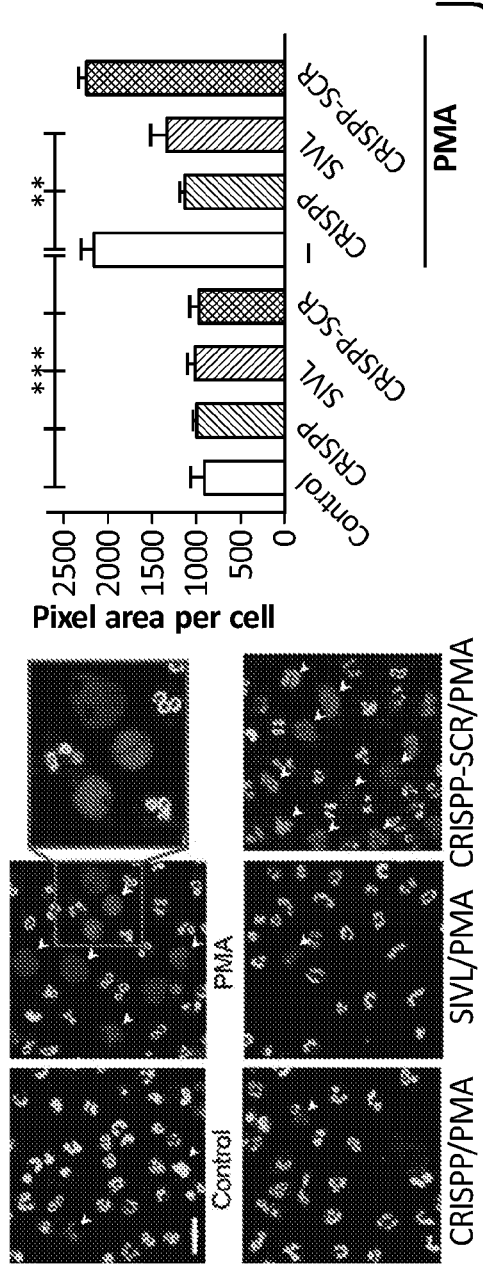
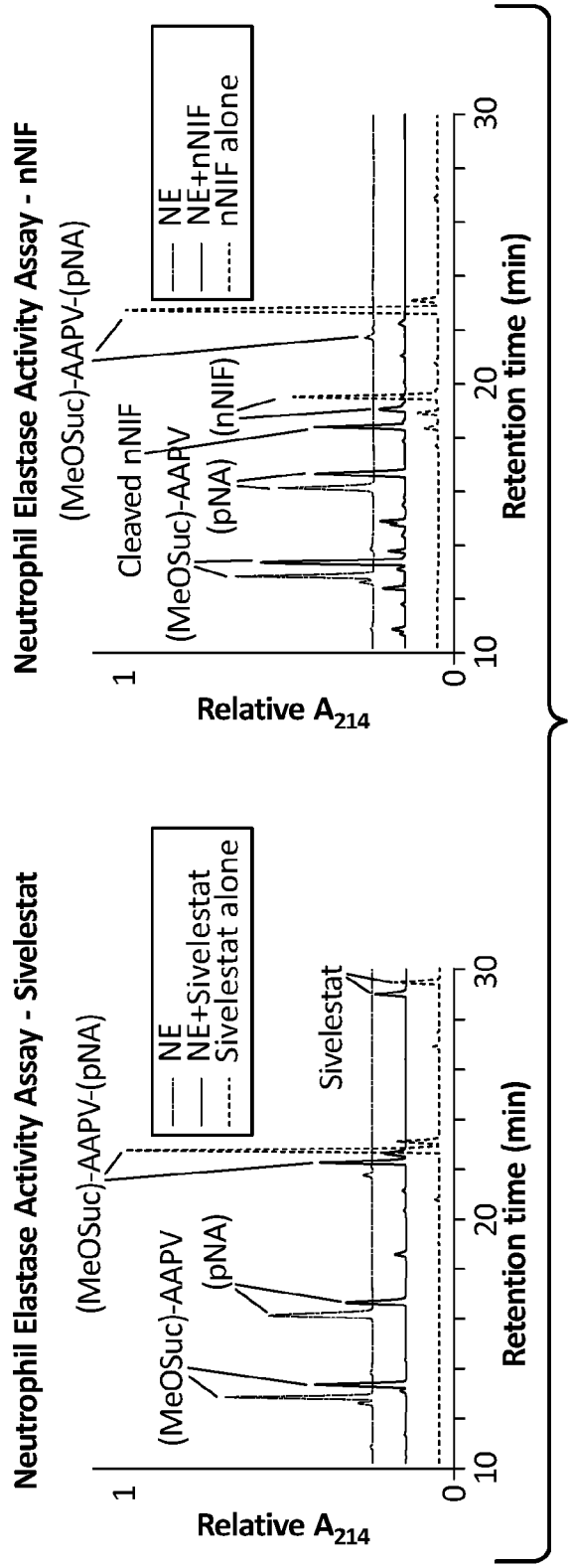
FIG. 12A
FIG. 12B

SEQUENCE LISTING

```
<160> NUMBER OF SEQ ID NOS: 10

<210> SEQ ID NO 1
<211> LENGTH: 29
<212> TYPE: PRT
<213> ORGANISM: Homo sapiens

<400> SEQUENCE: 1

Lys Phe Asn Lys Pro Phe Val Phe Leu Met Ile Glu Gln Asn Thr Lys
1               5                   10                  15

Ser Pro Leu Phe Met Gly Lys Val Val Asn Pro Thr Gln
            20                  25

<210> SEQ ID NO 2
<211> LENGTH: 30
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 2

Met Xaa Ile Pro Pro Glu Val Lys Phe Asn Lys Pro Phe Val Phe Leu
1               5                   10                  15

Met Ile Asp Gln Asn Thr Lys Val Pro Leu Phe Met Gly Lys
            20                  25                  30
```

<210> SEQ ID NO 3
<211> LENGTH: 40
<212> TYPE: PRT
<213> ORGANISM: Homo sapiens

<400> SEQUENCE: 3

Met Phe Leu Glu Ala Ile Pro Met Ser Ile Pro Pro Glu Val Lys Phe
1               5                   10                  15

Asn Lys Pro Phe Val Phe Leu Met Ile Glu Gln Asn Thr Lys Ser Pro
            20                  25                  30

Leu Phe Met Leu Lys Val Val Ser
        35                  40

<210> SEQ ID NO 4
<211> LENGTH: 35
<212> TYPE: PRT
<213> ORGANISM: Homo sapiens

<400> SEQUENCE: 4

Ser Ile Pro Pro Glu Val Lys Phe Asn Lys Pro Phe Val Phe Leu Met
1               5                   10                  15

Ile Glu Gln Asn Thr Lys Ser Pro Leu Phe Met Gly Lys Trp Asn Pro
            20                  25                  30

Thr Gln Lys
        35

<210> SEQ ID NO 5
<211> LENGTH: 29
<212> TYPE: PRT
<213> ORGANISM: Artificial Sequence
<220> FEATURE:
<223> OTHER INFORMATION: Scrambled Peptide Control

<400> SEQUENCE: 5

Leu Asn Thr Asn Lys Thr Lys Met Gly Val Gln Phe Pro Lys Met Pro
1               5                   10                  15

Phe Phe Lys Gln Ile Pro Val Asn Ser Leu Glu Phe Val
            20                  25

<210> SEQ ID NO 6
<211> LENGTH: 30
<212> TYPE: PRT
<213> ORGANISM: Artificial Sequence
<220> FEATURE:
<223> OTHER INFORMATION: Scrambled Peptide Control
<220> FEATURE:
<221> NAME/KEY: misc_feature
<222> LOCATION: (2)..(2)
<223> OTHER INFORMATION: Xaa can be any naturally occurring amino acid

<400> SEQUENCE: 6

Val Xaa Met Asp Ile Thr Pro Met Gln Val Gly Pro Leu Lys Met Lys
1               5                   10                  15

Pro Lys Val Ile Phe Asn Pro Phe Lys Leu Phe Glu Asn Phe
            20                  25                  30

<210> SEQ ID NO 7
<211> LENGTH: 40
<212> TYPE: PRT
<213> ORGANISM: Artificial Sequence
<220> FEATURE:
<223> OTHER INFORMATION: Scrambled Peptide Control

```
<400> SEQUENCE: 7

Pro Met Val Ser Val Ala Met Met Leu Ser Glu Asn Ile Phe Lys Leu
1               5                   10                  15

Pro Glu Val Lys Ser Val Pro Thr Glu Phe Phe Pro Lys Phe Ile Asn
                20                  25                  30

Met Lys Leu Leu Pro Phe Gln Ile
            35                  40

<210> SEQ ID NO 8
<211> LENGTH: 38
<212> TYPE: PRT
<213> ORGANISM: Homo sapiens

<400> SEQUENCE: 8

Pro Met Ser Ile Pro Pro Glu Val Lys Phe Asn Lys Pro Phe Val Phe
1               5                   10                  15

Leu Met Ile Glu Gln Asn Thr Lys Ser Pro Leu Phe Met Gly Lys Val
                20                  25                  30

Val Asn Pro Thr Gln Lys
            35

<210> SEQ ID NO 9
<211> LENGTH: 36
<212> TYPE: PRT
<213> ORGANISM: Homo sapiens

<400> SEQUENCE: 9

Ser Ile Pro Pro Glu Val Lys Phe Asn Lys Pro Phe Val Phe Leu Met
1               5                   10                  15

Ile Glu Gln Asn Thr Lys Ser Pro Leu Phe Met Gly Lys Val Val Asn
                20                  25                  30

Pro Thr Gln Lys
            35

<210> SEQ ID NO 10
<211> LENGTH: 36
<212> TYPE: PRT
<213> ORGANISM: Artificial Sequence
<220> FEATURE:
<223> OTHER INFORMATION: Scrambled Peptide Control

<400> SEQUENCE: 10

Phe Asn Val Val Pro Ser Asn Pro Thr Thr Val Pro Phe Gln Ile Pro
1               5                   10                  15

Val Phe Lys Glu Phe Glu Lys Ser Lys Asn Gln Met Leu Pro Leu Lys
                20                  25                  30

Met Gly Lys Ile
            35
```

NNIF AND NNIF-RELATED PEPTIDES AND RELATED METHODS

CROSS-REFERENCE TO RELATED APPLICATIONS

The present application is a national phase filing under 35 U.S.C. § 371 of International Application No. PCT/US2017/050072, filed on Sep. 5, 2017, which claims priority to and the benefit of U.S. Provisional Patent Application No. 62/492,019, filed Apr. 28, 2017 and U.S. Provisional Patent Application No. 62/383,243, filed Sep. 2, 2016, each of which is hereby incorporated by reference in its entirety.

REFERENCE TO SEQUENCE LISTING

The Sequence Listing submitted Feb. 26, 2019 as a text file named "21101_0375_U2 Sequence_Listing.txt," created on Feb. 26, 2019, and having a size of 4,400 bytes is hereby incorporated by reference pursuant to 37 C.F.R. § 1.52(e)(5).

STATEMENT REGARDING FEDERALLY SPONSORED RESEARCH

This invention was made with government support under Grant Numbers K08 HD049699, R01 HL044525 and R01 HL066277 awarded by the National Institutes of Health. The government has certain rights in the invention.

TECHNICAL FIELD

The present disclosure is directed to neonatal Neutrophil Inhibitory Factor (nNIF) and nNIF-Related Peptides (NRPs). The present disclosure is also directed to methods of using nNIF and NRPs for the inhibition of neutrophil extracellular trap (NET) formation. Furthermore, nNIF and NRPs can be used for the treatment of and the prophylaxis against inflammatory disorders and cancer.

BACKGROUND

Formation of neutrophil extracellular traps (NETs) can be an important component in the defensive armamentarium of neutrophils (polymorphonuclear leukocytes; PMNs) that allows them to capture, immobilize, and putatively kill microbes in the extracellular space (see Sorensen O E, et al., *Journal of clinical investigation.* 2016; 126 (5):1612-20; Brinkmann V, et al., *J Cell Biol.* 2012; 198 (5):773-83; Yipp B G, et al., *Blood.* 2013; 122 (16):2784-94; and Brinkmann V, et al., *Science.* 2004; 303 (5663):1532-5). NET formation occurs by a novel cell death process often called NETosis, although "vital" NETosis, in which the neutrophils do not immediately die, has also been described (see Yipp B G, et al., *Blood.* 2013; 122 (16):2784-94 and Yipp B G, et al., *Nature medicine.* 2012; 18 (9):1386-93). The molecular mechanisms leading to NET formation have not been completely dissected and may depend in part on the stimulus (see Sorensen O E, et al., *Journal of clinical investigation.* 2016; 126 (5):1612-20; Brinkmann V, et al., *J Cell Biol.* 2012; 198 (5):773-83; Yipp B G, et al., *Blood.* 2013; 122 (16):2784-94; and Papayannopoulos V, et al., *J Cell Biol.* 2010; 191 (3):677-91). Nevertheless, decondensation of chromatin and extrusion of DNA together with histones and granule contents are central events (see Sorensen O E, et al., *Journal of clinical investigation.* 2016; 126 (5):1612-20; Brinkmann V, et al., *J Cell Biol.* 2012; 198 (5):773-83; Yipp B G, et al., *Blood.* 2013; 122 (16):2784-94; Yipp B G, et al., *Nature medicine.* 2012; 18 (9):1386-93; Papayannopoulos V, et al., *J Cell Biol.* 2010; 191 (3):677-91). Deimination of histones mediated by peptidyl arginine deiminase 4 (PAD4) (see Wang Y, et al., *J Cell Biol.* 2009; 184 (2):205-13; Li P, et al. *J Exp Med.* 2010; 207 (9):1853-62; and Kolaczkowska E, et al. *Nature communications.* 2015; 6 (6673)) is thought to be a sine qua non for nuclear decondensation and NET formation (see Sorensen O E, et al., *Journal of clinical investigation.* 2016; 126 (5):1612-20).

NET-mediated capture and elimination of pathogens may complement traditional PMN antimicrobial activities including phagocytosis and intracellular killing (see Brinkmann V, et al., *J Cell Biol.* 2012; 198 (5):773-83 and Nauseef W M, *Immunol Rev.* 2007; 219 (88-102)). Clinical observations indicate that defects in NET formation contribute to intractable infections in some instances (see Brinkmann V, et al., *J Cell Biol.* 2012; 198 (5):773-83 and Bianchi M, et al., *Blood.* 2009; 114 (13):2619-22), but the importance of NETs in pathogen killing in vivo remains unclear (see Sorensen O E, et al., *Journal of clinical investigation.* 2016; 126 (5): 1612-20; Brinkmann V, et al., *J Cell Biol.* 2012; 198 (5):773-83; and Yipp B G, et al., *Blood.* 2013; 122 (16): 2784-94). Conversely, there is substantial evidence that NETs and NET-associated factors, including histones and granule proteases, mediate vascular and tissue injury and that NET-mediated injury is a previously-unrecognized mechanism of innate immune collateral damage to the host (see Sorensen O E, et al., *Journal of clinical investigation.* 2016; 126 (5): 1612-20; Brinkmann V, et al., *J Cell Biol.* 2012; 198 (5):773-83; Yipp B G, et al., *Blood.* 2013; 122 (16):2784-94; Kolaczkowska E, et al., *Nature communications.* 2015; 6 (6673); and Xu J, et al. *Nature medicine.* 2009; 15 (11):1318-21). Experimental models and limited clinical observations suggest that intra- or extravascular NET formation contributes to tissue injury in bacteremia (Kolaczkowska E, et al., *Nature communications.* 2015; 6 (6673); Clark S R, et al., *Nature medicine.* 2007; 13 (4):463-9; and McDonald B, et al. *Cell host & microbe.* 2012; 12 (3): 32433), transfusion-related acute lung injury (see Caudrillier A, et al., *J Clin Invest.* 2012; 122 (7):2661-71), primary graft dysfunction after lung transplantation (see Sayah D M, et al., *American journal of respiratory and critical care medicine.* 2015; 191 (4):455-63), sterile vasculopathies and immune inflammation (see Chen G, et al., *Blood.* 2014; 123 (24): 3818-27; and Lood C, et al., *Nature medicine.* 2016; 22 (2):146-53), thrombosis (see Fuchs T A, et al., *Proc Natl Acad Sci USA.* 2010; 107 (36):15880-5), and influenza (see Pillai P S, et al. *Science* (New York, N.Y.). 2016; 352 (6284):463-6). Thus, NET formation may be an important maladaptive activity of neutrophils (see Sorensen O E, et al., *Journal of clinical investigation.* 2016; 126 (5):1612-20) if it is triggered inappropriately or is unregulated in infection and inflammation.

Human neonates have unique and complicated immune regulation, susceptibility to infection, and inflammatory pathology. Although the infant is in a sterile environment in utero, it can be challenged by pathogens and their products before or during labor (see McDonagh S, et al., *Journal of infectious diseases.* 2004; 190 (4):826-34). Furthermore, newborns are rapidly colonized with bacteria after delivery, a process associated with increases in circulating and bone marrow neutrophils (see Palmer C, et al. *PLoS biology.* 2007; 5 (7):e177; Jost T, et al., *PloS one.* 2012; 7 (8):e44595; and Deshmukh H S, et al., *Nat Med.* 2014; 20 (5):524-30). Complex adaptations appear to have evolved that prevent excessive, injurious inflammation in the perinatal period and in the abrupt neonatal transition from the protected intrauterine environment to continuous microbial colonization and exposure (see Dowling D J, et al. *Trends in immunology.* 2014; 35 (7):299310; Adkins B., *Immunologic research.* 2013; 57 (1-3):246-57; and Elahi S, et al., *Nature.* 2013; 504 (7478):158-62). These adaptations may, however, be accompanied by increased susceptibility to infection (see Adkins B., *Immunologic research.* 2013; 57 (1-3):246-57 and Elahi S, et al., *Nature.* 2013; 504 (7478):158-62). It has been found that PMNs isolated from umbilical cord blood of preterm and term infants do not form NETs when stimulated and have a defect in NET-mediated bacterial killing, suggesting such an adaptation (see Yost C C, et al., *Blood.* 2009; 113 (25):6419-27). Other investigators subsequently reported temporally delayed NET formation when isolated neonatal neutrophils were stimulated in vitro (see Marcos V, et al. *Blood.* 2009; 114 (23):4908-11, author reply 11-2).

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1A is a series of images depicting neutrophils from seven preterm neonates that were longitudinally examined over the first 28 days after birth for NET formation in response to lipopolysaccharide (LPS) (100 ng/mL, 1 hour) assessed by live cell imaging (NETS=red fluorescence, yellow arrows; nuclear DNA=gray; 20× magnification, scale bar=100 µm), and release of NET-associated histone H3 (fold change over baseline; mean±SEM) is depicted in the graph. One way ANOVA with Tukey's post hoc testing. *$P<0.05$, **$P<0.01$ compared to control histone H3 release arbitrarily set at 1 (red dashed line).

FIG. 1B is two images depicting neutrophils isolated from cord blood of a healthy term neonate on the day of delivery (left panel) or from venous blood on day 2 after birth (right panel) that were stimulated with LPS (100 ng/mL, 1 hour) and imaged as in FIG. 1A. Analysis of NET formation by neutrophils from a second term neonate yielded the same pattern.

FIG. 1C is two images depicting neutrophils isolated from venous blood of a healthy pregnant woman on the day of delivery that were incubated in medium alone or stimulated with LPS (100 ng/mL) for 1 hour and imaged as in FIG. 1A (60× magnification, scale bar=100 µm). Neutrophils from a second healthy term mother also robustly formed NETs in response to LPS.

FIG. 1D is a series of images depicting neutrophils that were isolated from venous blood of 60-day-old preterm neonates (n=5), preincubated for 1 hour with day 60 autologous plasma or with stored autologous cord blood plasma, stimulated with LPS, and assessed for NET formation as in FIG. 1A (60× magnification, scale bar=100 µm). Neutrophils isolated from venous blood of healthy adults and preincubated in autologous or stored cord blood plasma were studied in parallel. Release of NET-associated histone H3 (fold change over baseline; mean±SEM) is depicted in the graph. One way ANOVA with Tukey's post hoc testing. *$P<0.05$ LPS/adult versus LPS/neonatal; **$P<0.01$ neonatal PMNs in autologous plasma versus cord blood plasma; †$P<0.001$ adult PMNs in autologous plasma versus cord blood plasma. FIGS. 1A-1D indicate that a NET-Inhibitory Factor is present in human umbilical cord blood.

FIG. 2A is a provisional partial sequence of nNIF from mass spectroscopy, and published sequences of CRISPP (see Cercek L, et al. *Cancer Detect Prev.* 1992; 16 (5-6):305-19) and A1AT.

FIG. 2B depicts samples of healthy term neonate cord blood plasma (n=4) and adult venous plasma (n=4) that were analyzed by western blotting using a polyclonal antibody against the carboxy-terminus of A1AT (left panel) (the full gel is shown in FIG. 10, which is described below). The right panel depicts use of size exclusion of full-length A1AT, quantitative western blotting with the same polyclonal antibody against the A1AT carboxy-terminus, and a standard curve generated using synthetic nNIF (see Table 2 below) to measure nNIF concentrations in cord blood plasma from preterm neonates and venous plasma from healthy adults (n=8 in each group). Student's t test, **$P<0.01$.

FIG. 2C is a series of images depicting NET formation by LPS-stimulated (100 ng/mL, 1 hour) adult neutrophils that were assessed as in FIG. 1A after preincubation of the PMNs in control medium, cord blood plasma, cord blood plasma depleted of nNIF using a polyclonal carboxy-terminus A1AT antibody coupled to affinity beads, or eluate from the affinity beads (60× magnification, scale bar=50 µm). This result was consistent in three experiments with neutrophils from different donors.

FIG. 2D is an image depicting full-length A1AT, synthetic nNIF, and samples of depleted cord blood plasma and eluate studied in FIG. 2C that were subjected to western blotting using the carboxy-terminus A1AT antibody. Full-length A1AT (52 kDa) was not detected on this 16.5% Tris-tricine gel due to its size.

FIG. 2E is a series of images depicting NET formation by LPS-activated adult PMNs that were assessed as in FIG. 1A after preincubation for 1 hour in control medium (second panel), or with full-length A1AT (2 µM) or synthetic nNIF (1 nM) (n=3). One way ANOVA with Tukey's post hoc testing. *$P<0.05$ nNIF versus both control medium/LPS and A1AT/LPS. NET-associated histone H3 content (fold change over baseline) is depicted in the graph. FIGS. 2A-2E indicate that nNIF and related NRPs represent a family of NET-Inhibitory Peptides.

FIG. 3A depicts LPS (100 ng/mL) activation. **$P<0.05$ for LPS and CRISPP-SCR/LPS compared to control, †$P<0.05$ for CRISPP/LPS and nNIF/LPS compared to both LPS and CRISPP-SCR/LPS.

FIG. 3B depicts phorbol myristate acetate (PMA) (20 nM) activation. *$P<0.05$ for both nNIF/PMA and CRISPP/PMA compared to PMA or CRISPP-SCR/PMA; **$P<0.01$ for CRISPP/PMA versus CRISPP-SCR/PMA.

FIG. 3C depicts *S. aureus* (SA; MOI 100:1) activation. *$P<0.05$ for CRISPP/SA compared to SA or CRISPP-SCR/SA.

FIG. 3D depicts dengue virus (MOI 0.05:1) activation. Viral culture medium alone served as a "mock" control (left panels) for dengue virus. Following incubation the PMNs were immediately fixed in the incubation medium (2% paraformaldehyde) prior to imaging, and quantitation of histone H3 release was not possible.

FIG. 3E depicts Heme (1 µM). *$P<0.05$ for Heme, LPS, and CRISPP-SCR/Heme versus control; †$P<0.05$ for CRISPP/Heme versus Heme. FIGS. 3A-3E indicate that nNIF and the NRP CRISPP inhibit in vitro NET formation triggered by a spectrum of NET-inducing agonists. Neutrophils from venous blood of healthy adults were preincubated in medium alone or with nNIF, CRISPP, or CRISPP-SCR (all 1 nM) for 1 hour, and activated with the indicated agonists (n≥3 for each), and NET formation was assessed after 1 hour of incubation as in FIG. 1A (20× magnification; scale bar=50 µm). All data are ±SEM. In FIGS. 3A, 3B, 3C, and 3E, control values arbitrarily set at 1 are indicated by dashed red lines. One way ANOVA with Tukey's post hoc testing was applied in FIGS. 3A, 3B, 3C, and 3E. nNIF was not studied in FIG. 3C or 3D.

FIGS. 4A and 4B indicate that NRPs do not dismantle NETs.

FIGS. 5A and 5B indicate that A1ATm$^{358}$ inhibits NET formation.

FIG. 6A is a graph depicting results, after preincubation, of neutrophils that were stimulated with LPS (100 ng/mL) to trigger NET formation and incubated with a pathogenic isolate of *E. coli*. Total, phagocytic, and NET-mediated bacterial killing were measured (see Yost C C, et al., Blood. 2009; 113 (25):6419-27). One way ANOVA with Bonferonni's post hoc testing; *P<0.05, **P<0.01.

FIG. 6B is a graph depicting reactive oxygen species generation that was measured by dihydrorhodamine detection after LPS stimulation (100 ng/mL, 1 hour).

FIG. 6C is a graph depicting phagocytosis of fluorescently-labeled *E. coli* bioparticles that were measured by microscopy after a 4 hour incubation. Treatment with cytochalasin B and D served as a control for inhibition of phagocytosis. Student's t test, *P<0.05.

FIG. 6D is a graph depicting chemotaxis in response to IL-8 (2 ng/mL) that was examined in a Boyden chamber assay. The dashed line indicates the response to IL-8 alone arbitrarily set at 1.

FIG. 6E is a graph depicting surface translocation of P-selectin on platelets activated by thrombin (0.1 U/mL) that was measured by flow cytometry. The dashed line indicates surface P-selectin on unstimulated platelets.

FIG. 6F is a graph depicting formation of platelet-neutrophil aggregates that was measured after mixing of platelets activated with thrombin (0.1 U/mL) and neutrophils activated with LPS (100 ng/mL). The dashed line indicates control aggregate formation in response to LPS stimulation of the PMNs alone. *P<0.05 for CRISPP and CRISPP-SCR compared to control. FIGS. 6A-6F are a series of graphs depicting isolated adult neutrophils or platelets that were preincubated with buffer or with CRISPP, nNIF, or CRISPP-SCR (1 nM, 1 hour for each) followed by measurement of functional responses. A minimum of three separate assays were done for each response. Error bars=SEM. Tukey's post hoc testing was applied in FIGS. 6B, 6D, 6E, and 6F. FIGS. 6A-6F indicate that NRPs selectively inhibit NET formation.

FIG. 7A is a series of images depicting neutrophils that were preincubated in medium alone, with nNIF, nNIF-SCR, CRISPP, or CRISPP-SCR (all 1 nM), or with the irreversible PAD4 inhibitor Cl-amidine (10 µM) for 1 hour; treated with PMA (20 nM); and then incubated on poly-L-lysine-coated coverslips for 2 hours, followed by examination for nuclear decondensation (arrows) by live cell imaging (green fluorescence=nuclear DNA; 60× magnification, scale bar=20 µm).

FIG. 7B is a graph depicting nuclear areas that were measured (n=4) using IMAGEJ™ software (mean nuclear pixel area per cell±SEM). Paired Student's t test, *P<0.05, § P=0.057.

FIG. 7C is a graph depicting nNIF (1 nM), nNIF-SCR (1 nM), and Cl-amidine (10 µM) that were examined in a cell-free deimination assay employing recombinant PAD4 and a synthetic substrate. One way ANOVA with Tukey's post hoc testing, ***P<0.001.

FIG. 7D is a series of images wherein the left panels depict neutrophils that were preincubated for 30 minutes in medium, with nNIF or nNIF-SCR (both 1 nM), or with Cl-amidine (10 µM), and activated for 15 minutes with PMA (20 nM), and citrullinated-histone H3 was detected by immunocytochemistry (n=3). Green fluorescence= citrullinated-histone H3, magenta fluorescence=nuclear DNA (60× magnification; scale bar=20 µm). The right panel depicts Histone H3 citrullination that was quantified using IMAGEJ™ software (mean citrullinated-histone H3 pixel area per cell±SEM) (n=3). One way ANOVA with Tukey's post hoc testing, *P<0.05.

FIG. 7E is a series of images depicting neutrophils that were incubated with FLAG-tagged CRISPP-FLAG or CRISPP-SCR-FLAG (1 nM for both) for 1 hour, activated with LPS (100 ng/mL) for a further 2 hours, and then examined by confocal microscopy using an anti-FLAG antibody (n=3). Yellow fluorescence=FLAG tag; blue fluorescence=nuclear counterstain (60× magnification, scale bar=20 µm). The FLAG-tagged peptides were not internalized by isolated human platelets (unpublished experiments). FIGS. 7A-7E indicate that NRPs inhibit nuclear decondensation and histone citrullination in activated neutrophils.

FIG. 8A depicts results of peritoneal fluid NET formation (red fluorescence, yellow arrow) assessed by live cell imaging (60× magnification, scale bar=50 µm) and histone H3 release (red dashed line=baseline arbitrarily set at 1). Three mice per group. One way ANOVA with Tukey's post hoc testing, ***P<0.001 for CRISPP and nNIF versus CRISPP-SCR.

FIG. 8B depicts results of NET formation on the surfaces of peritoneal membranes (red fluorescence, yellow arrows) that was quantified by counting the number of NETs that crossed standardized grid lines in four random microscopic fields (60× magnification; scale bar=50 µm) using IMAGEJ™ software. A second experiment yielded a similar pattern. FIGS. 8A and 8B depict C57BL/6 mice that were not pretreated or pretreated with nNIF, CRISPP, or CRISPP-SCR (10 mg/kg i.p.; 1 hour) and were inoculated with *E. coli* (4.5×10$^7$ bacteria i.p.). After 3 hours, the animals were sacrificed, and peritoneal fluid (FIG. 8A) and membranes (FIG. 8B) were collected for analysis.

FIG. 8C depicts C57BL/6 mice that were not pretreated (left two bars) or that were pretreated with CRISPP, nNIF, or CRISPP-SCR, and that were inoculated with *E. coli* i.p. as in FIGS. 8A and 8B. Neutrophil numbers in peritoneal fluid were counted after 3 hours (3-5 mice/group). One way ANOVA with Neuman-Keul's post hoc testing; †P<0.05 for CRISPP versus CRISPP-SCR or not pretreated; *P<0.05 for control versus all other groups.

FIG. 8D depicts C57BL/6 mice that were pretreated with CRISPP or CRISPP-SCR and that were inoculated with *E. coli* as in FIGS. 8A and 8B (5 animals/group). After 3 hours, bacteria colony forming units (cfu) in the peritoneal fluid were measured (single-tailed Mann-Whitney test; *P<0.05).

FIG. 8E depicts peritoneal fluid NET formation, imaged and measured as in FIG. 8A (10 mice/group). *P<0.05 for CRISPP/*E. coli* and nNIF/*E. coli* compared to CRISPP-SCR/*E. coli* and *E. coli*.

FIG. 8F depicts NET formation on peritoneal membrane surfaces, imaged and quantitated as in FIG. 8B (3 mice in each group). *P<0.05 for *E. coli* versus control (red dashed line); **P<0.01 for CRISPP-SCR/*E. coli* versus control; †P<0.05 for CRISPP/*E. coli* and nNIF/*E. coli* versus CRISPP-SCR/*E. coli*. One way ANOVA with Tukey's post-hoc testing applied in FIGS. 8E and 8F. In FIGS. 8E and 8F, Swiss-Webster mice that were not pretreated or that were pretreated with nNIF, CRISPP, or CRISPP-SCR were inoculated with *E. coli* i.p. as in FIGS. 8A and 8B. After 3 hours, peritoneal fluid and membranes were collected. FIGS. 8A-8F indicate that nNIF and CRISPP inhibit in vivo NET formation.

FIGS. 9A-9C indicate that nNIF and CRISPP improve survival in experimental systemic inflammation.

FIG. 12A depicts nuclear decondensation (white arrowheads and magnified image) that were assessed as in FIGS. 7A-7E after a 1 hour preincubation in medium alone, with neutrophil elastase (NE) inhibitor sivelestat (SIVL; 200 nM), or with CRISPP or CRISPP-SCR (both 1 nM) followed by treatment with PMA (20 nM) and an additional 1 hour incubation (n=3). Green fluorescence=nuclear DNA, (60× magnification, scale bar=20 µm). Nuclear area was quantified using IMAGEJ™ software (nuclear pixel area per cell±SEM). One way ANOVA with Tukey's post hoc testing; P<0.01, *P<0.001.

FIG. 12B depicts NE enzyme activity that was examined by cleavage of the synthetic substrate (MeOSuc)-AAPV-(pNA) to (MeOSuc)-AAPV and (pNA) as products detected by liquid chromatography and chromatogram peak identification by mass spectroscopy. (MeOSuc)-AAPV-(pNA) (160 µm) was incubated with NE (2 mU), sivelestat (160 µm), or NE and sivelestat (left panel) or with NE (2 mU), nNIF (10 nM), or NE and nNIF (right panel) for 3 hours at 37° C. Chromatograms are offset on the X and Y axes for ease of comparison. In the presence of NE alone, the (MeOSvc)-AAPV-(pNA) peak was almost completely eliminated and (MeOSvc)-AAPV and (pNA) peaks were generated. In the presence of sivelestat, this substrate cleavage was inhibited but not eliminated. In contrast, it was not inhibited by nNIF. This pattern was seen in three separate experiments. Using two additional assays employing different protocols, NE substrates, and detection methods, neither nNIF nor CRISPP inhibited NE activity in multiple experiments. FIGS. 12A and 12B indicate that NE mediates nuclear decondensation but nNIF and CRISPP do not inhibit NE activity in vitro.

DETAILED DESCRIPTION

Figure 4A:
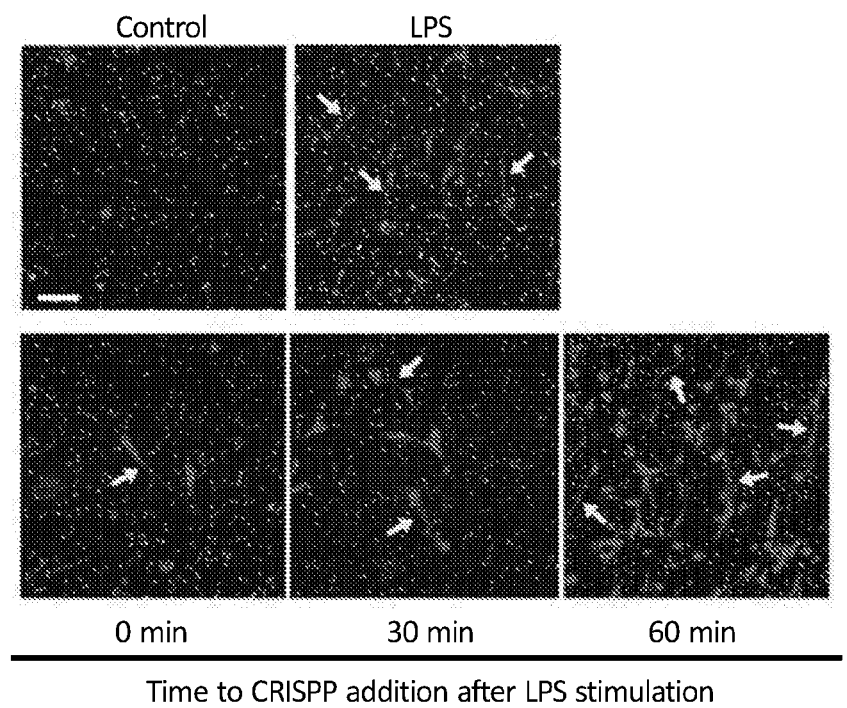
FIG. 4A is a series of images depicting neutrophils isolated from venous blood of healthy adults that were incubated in medium alone (Control) or activated with LPS (100 ng/mL). CRISPP (1 nM) was added at 0, 30, or 60 minutes after LPS, and the presence of NETs was assessed by live cell imaging as in FIG. 1A after an additional 1 hour of incubation (20× magnification; scale bar=100 µm). The images are representative of three separate experiments.

This disclosure relates to neonatal Neutrophil Inhibitory Factor (nNIF) and nNIF-Related Peptides (NRPs). The disclosure is also related to methods of using nNIF and NRPs for the inhibition of neutrophil extracellular trap (NET) formation. nNIF and NRPs can be used for the treatment of and the prophylaxis against inflammatory disorders and cancer. It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

Each and every patent, report, and other reference recited herein is incorporated by reference in its entirety.

A "NET-Inhibitory Peptide (NIP)" is an anti-inflammatory agent that inhibits neutrophil extracellular trap (NET) formation. Examples of NIPs include, but are not limited to: neonatal NET-Inhibitory Factor (nNIF); a pharmaceutically acceptable salt of nNIF; an analog of a naturally occurring form of nNIF, which nNIF analog inhibits NETosis and/or the formation of NETs and is structurally altered, relative to a given human nNIF, by at least one amino acid addition, deletion, or substitution, or by incorporation of one or more amino acids with a blocking group; a pharmaceutically acceptable salt of a nNIF analog; a nNIF-Related Peptide (NRP); a pharmaceutically acceptable salt of a NRP; a NRP analog; or a pharmaceutically acceptable salt of a NRP analog.

A "neonatal Neutrophil Inhibitory Factor peptide" or "nNIF peptide" is defined herein as a nNIF which is naturally occurring in mammals.

A "neonatal NIF-Related Peptide" or "NRP" is defined herein as a Cancer-Associated SCM-Recognition, Immune Defense Suppression, and Serine Protease Protection Peptide (CRISPP) which is naturally occurring in humans; A1ATm$^{358}$, which has been shown to inhibit NET formation; HTRA1-CF, other nNIF-Related Peptides; and analogs of naturally occurring forms of NRPs that inhibit NETosis and/or the formation of NETs and are structurally altered, relative to a given human NRP, by at least one amino acid addition, deletion, or substitution, or by incorporation of one or more amino acids with a blocking group.

"Inflammatory disorders" are defined herein as disorders characterized by pathological inflammation. Inflammatory disorders include, but are not limited to, conditions associated with infection, autoimmunity, and allergy. Inflammatory disorders as defined herein may include, but are not limited to, acute respiratory distress syndrome (ARDS); bronchopulmonary dysplasia (BPD); chronic obstructive pulmonary disease (COPD); cystic fibrosis; inflammation in cancer and its complications; inflammatory bowel disease (IBD); inflammatory lung disease (ILD); influenza-induced pneumonitis; necrotizing enterocolitis (NEC); neonatal chronic lung disease (CLD); periodontitis; pre-eclampsia; retinopathy of prematurity (ROP); sepsis; systemic inflammatory response syndrome (SIRS); thrombosis; transfusion-related acute lung injury (TRALI); vasculitis; autoimmune syndromes including, but not limited to, rheumatoid arthritis (RA), systemic lupus erythematosus (SLE), and Wegener's granulomatosis (WG); and disorders of nonresolved inflammation. There are other inflammatory disorders not listed herein but known to those skilled in the art. For example, see Kumar, et al., Robbins and Cotran Pathologic Basis of Disease, pp. 43-77, 8th Edition, 2010, Saunders Elsevier, Philadelphia, Pa.; Nathan, Nature, 2002, 420: 846-852; and Amulic, et al., Annu Rev Immunol, 2012, 30: 459-489.

The phrase "does not globally depress polymorphonuclear leukocyte (PMN) function," when used in connection with a NIP, means that although the NIP may inhibit or substantially inhibit NETosis, the NIP does not inhibit or substantially inhibit other PMN functions. Other PMN functions include, but are not limited to, chemotaxis, chemokine synthesis and secretion, cytokine synthesis and secretion, extracellular bacterial killing, intracellular bacterial killing, phagocytosis, and/or reactive oxygen species (ROS) generation. Methods of assaying these functions are known in the art. For example, Example 16 describes methods of assaying phagocytic bacterial killing.

This disclosure relates to therapeutic and related uses of NET Inhibitory Peptides (NIPs), neonatal NET-Inhibitory Factor (nNIF), nNIF analogs, nNIF-Related Peptides (NRPs), and NRP analogs. In some embodiments, the NIPs, nNIF, nNIF analogs, NRPs, and/or NRP analogs may be used for inhibiting NETosis and/or the formation of neutrophil extracellular traps (NETs).

In exploring the mechanism(s) for blunted neonatal NET deployment, a peptide was discovered in umbilical cord blood that inhibits NET formation in vitro and in vivo, and that appears to be an endogenous regulator of NET generation. Related peptides that inhibit NETosis were also identified. These previously-unrecognized modulators of NET formation may have potential as selective anti-inflammatory agents, in addition to regulatory activities in specific inflammatory settings or tissue compartments.

A first aspect of the disclosure relates to methods of treating inflammatory disorders. In certain embodiments, this disclosure provides methods of treating a patient having an inflammatory disorder, the methods comprising administering to the patient an effective amount of a pharmaceutical composition comprising a NIP, or a pharmaceutically acceptable salt of a NIP, and a pharmaceutically acceptable carrier to reduce a pathological effect or symptom of the inflammatory disorder. The pathological effects or symptoms may include one or more of the following: pain, heat, redness, swelling and/or edema, hypotension, fibrosis and/or post-inflammatory fibrosis, end organ failure (i.e., renal, cardiac, hepatic), tissue damage, and/or loss of function.

In some embodiments, this disclosure provides methods of treating a patient having an inflammatory disorder, the methods comprising administering to the patient an effective amount of a pharmaceutical composition comprising a nNIF, or a pharmaceutically acceptable salt of a nNIF, and a pharmaceutically acceptable carrier to reduce a pathological effect or symptom of the inflammatory disorder.

In other embodiments, the disclosure provides methods of treating a patient having an inflammatory disorder, the methods comprising administering to the patient an effective amount of a pharmaceutical composition comprising a nNIF analog, or a pharmaceutically acceptable salt of a nNIF analog, and a pharmaceutically acceptable carrier to reduce a pathological effect or symptom of the inflammatory disorder.

In yet other embodiments, the disclosure provides methods of treating a patient having an inflammatory disorder, the methods comprising administering to the patient an effective amount of a pharmaceutical composition comprising a NRP, or a pharmaceutically acceptable salt of a NRP, and a pharmaceutically acceptable carrier to reduce a pathological effect or symptom of the inflammatory disorder.

In still other embodiments, the disclosure provides methods of treating a patient having an inflammatory disorder, the methods comprising administering to the patient an effective amount of a pharmaceutical composition comprising a NRP analog, or a pharmaceutically acceptable salt of a NRP analog, and a pharmaceutically acceptable carrier to reduce a pathological effect or symptom of the inflammatory disorder.

In some embodiments, the patient may be a mammal. In certain embodiments the patient may be a human. Any patient or subject requiring inhibition of NETosis and/or NET formation may potentially be a candidate for treatment with a NIP, a pharmaceutically acceptable salt of a NIP, a nNIF, a pharmaceutically acceptable salt of a nNIF, a nNIF analog, a pharmaceutically acceptable salt of a nNIF analog, a NRP, a pharmaceutically acceptable salt of a NRP, a NRP analog, and/or a pharmaceutically acceptable salt of a NRP analog.

In some embodiments, the inflammatory disorder may at least partially involve or be at least partially caused by neutrophil extracellular trap (NET) formation and/or NETosis. In some embodiments, the inflammatory disorder may be an acute inflammatory disorder, a chronic inflammatory disorder, and/or an immune disorder. In other embodiments, the inflammatory disorder may be an autoimmunity disorder. In yet other embodiments, the inflammatory disorder may be a disorder of coagulation.

In some embodiments, the inflammatory disorder may be one or more of, but is not limited to, acute respiratory distress syndrome (ARDS); bronchopulmonary dysplasia (BPD); chronic obstructive pulmonary disease (COPD); cystic fibrosis; inflammation in cancer and its complications; inflammatory bowel disease (IBD); inflammatory lung disease (ILD); influenza-induced pneumonitis; necrotizing enterocolitis (NEC); neonatal chronic lung disease (CLD); periodontitis; pre-eclampsia; retinopathy of prematurity (ROP); sepsis; systemic inflammatory response syndrome (SIRS); thrombosis; transfusion-related acute lung injury (TRALI); vasculitis; autoimmune syndromes including, but not limited to, rheumatoid arthritis (RA), systemic lupus erythematosus (SLE), and Wegener's granulomatosis (WG); and disorders of nonresolved inflammation. There are other inflammatory disorders not listed herein but known to those skilled in the art. For example, see Kumar, et al., Robbins and Cotran Pathologic Basis of Disease, pp. 43-77, 8th Edition, 2010, Saunders Elsevier, Philadelphia, Pa.; Nathan, Nature, 2002, 420: 846-852; and Amulic et al., Annu Rev Immunol, 2012, 30: 459-489.

In another aspect, this disclosure relates to methods for treating a patient having a cancer. In some embodiments, the cancer may be at least one of melanoma, ovarian cancer, stomach cancer, lung cancer, or another suitable cancer. In certain embodiments, the methods for treating a patient having a cancer may include administering to the patient an effective amount of a pharmaceutical composition including a NIP. The pharmaceutical composition may also include a NIP and a pharmaceutically acceptable carrier. In various embodiments, the pharmaceutical composition may reduce, or be configured to reduce, a pathological effect or symptom of the cancer.

In some embodiments, the NIP may be one of a nNIF, a pharmaceutically acceptable salt of a nNIF, a nNIF analog, a pharmaceutically acceptable salt of a nNIF analog, a NRP, a pharmaceutically acceptable salt of a NRP, a NRP analog, and/or a pharmaceutically acceptable salt of a NRP analog. In certain embodiments, the pharmaceutical composition may inhibit or substantially inhibit NET formation. For example, the pharmaceutical composition may, at least in part, reduce a pathological effect or symptom of the cancer by inhibiting NET formation in the patient having cancer. As stated above, the patient may be a mammal, such as a human.

In another aspect, this disclosure relates to methods for treating a patient at risk of developing a cancer. As discussed above, the cancer may be at least one of melanoma, ovarian cancer, stomach cancer, lung cancer, or another suitable cancer. In certain embodiments, the methods for treating a patient at risk of developing a cancer may include administering to the patient an effective amount of a pharmaceutical composition including a NIP. The pharmaceutical composition may also include a NIP and a pharmaceutically acceptable carrier. In various embodiments, the pharmaceutical composition may reduce, or be configured to reduce, the risk of developing the cancer.

In some embodiments, the NIP may be one of a nNIF, a pharmaceutically acceptable salt of a nNIF, a nNIF analog, a pharmaceutically acceptable salt of a nNIF analog, a NRP, a pharmaceutically acceptable salt of a NRP, a NRP analog, and/or a pharmaceutically acceptable salt of a NRP analog. In certain embodiments, the pharmaceutical composition may inhibit or substantially inhibit NET formation. For example, the pharmaceutical composition may, at least in part, reduce the risk of developing the cancer by inhibiting NET formation in the patient at risk of developing the cancer. As stated above, the patient may be a mammal, such as a human.

In another aspect, this disclosure relates to methods for inhibiting, or substantially inhibiting, metastasis in a patient having cancer. The cancer may be at least one of melanoma, ovarian cancer, stomach cancer, lung cancer, or another suitable cancer. In certain embodiments, the methods for inhibiting metastasis may include administering to the patient an effective amount of a pharmaceutical composition including a NIP. The pharmaceutical composition may also include a NIP and a pharmaceutically acceptable carrier. In various embodiments, the pharmaceutical composition may reduce, or be configured to reduce, the risk of metastasis in the patient.

In some embodiments, the NIP may be one of a nNIF, a pharmaceutically acceptable salt of a nNIF, a nNIF analog, a pharmaceutically acceptable salt of a nNIF analog, a NRP, a pharmaceutically acceptable salt of a NRP, a NRP analog, and/or a pharmaceutically acceptable salt of a NRP analog. In certain embodiments, the pharmaceutical composition may inhibit or substantially inhibit NET formation. For example, the pharmaceutical composition may, at least in part, reduce the risk of metastasis by inhibiting NET formation in the patient having a cancer. As stated above, the patient may be a mammal, such as a human.

In certain embodiments, the pharmaceutical composition comprising the NIP may not globally depress functions of PMNs. The functions of PMNs include, but are not limited to, chemotaxis, phagocytosis, reactive oxygen species (ROS) generation, cytokine/chemokine synthesis and secretion, NET formation/NETosis, and/or intracellular/extracellular bacterial killing. In certain embodiments, the pharmaceutical composition may not inhibit or substantially inhibit PMN phagocytosis. In other embodiments, the pharmaceutical composition may not inhibit or substantially inhibit PMN chemotaxis. In yet other embodiments, the pharmaceutical composition may not inhibit or substantially inhibit generation of ROS. In other embodiments, the pharmaceutical composition may not inhibit or substantially inhibit PMN intracellular bacterial killing. Accordingly, administration of the pharmaceutical composition comprising the NIP to treat a patient having cancer, or at risk of developing cancer, may avoid some of the side effects of chemotherapy regimens used in the treatment of or prophylaxis against cancer.

In another aspect, this disclosure relates to methods for treating patients having a cancer, wherein the methods include identifying NET formation at or adjacent cancerous cells in a patient. In some embodiments, the methods may further include administering to the patient having NET formation (e.g., the patient wherein NET formation is identified) an effective amount of a pharmaceutical composition including a NIP and a pharmaceutically acceptable carrier to reduce a pathological effect or symptom of the cancer. In certain embodiments, the methods may include obtaining a sample of cancerous cells from the patient. The cancerous cells, or the sample including cancerous cells, can be examined and/or tested to identify the presence of NET formation.

In another aspect, this disclosure relates to methods for treating patients at risk of developing cancer. In various embodiments, the methods may include identifying NET formation in a patient. Upon identification of NET formation in a patient at risk of developing cancer, the methods may include administering to the patient an effective amount of a pharmaceutical composition including a NIP and a pharmaceutically acceptable carrier, to reduce the patient's risk of developing the cancer.

In some embodiments, the pharmaceutical composition may substantially inhibit NET formation and/or NETosis. In other embodiments, the pharmaceutical composition may inhibit or substantially inhibit NET-mediated inflammatory tissue damage.

In another aspect, this disclosure relates to methods of diagnosing a patient having cancer who would benefit from treatment with a NET-Inhibitory Peptide (NIP). In certain embodiments, the method may include obtaining a sample of cancerous cells from the patient, detecting whether NET formation is present in the sample of cancerous cells, and/or diagnosing the patient as a patient who would benefit from treatment with a NIP when the presence of NET formation in the sample of cancerous cells is detected.

In various embodiments, the cancerous cells may include at least one of melanocytes, ovarian cells, stomach cells, lung cells, or another suitable type of cancerous cells.

In another aspect, this disclosure relates to methods of diagnosing and treating a patient having cancer who would benefit from treatment with a NET-Inhibitory Peptide (NIP). In some embodiments, the method may include obtaining a sample of cancerous cells from the patient, detecting whether NET formation is present in the sample of cancerous cells, diagnosing the patient as a patient who would benefit from treatment with a NIP when the presence of NET formation in the sample of cancerous cells is detected, and/or administering an effective amount of a pharmaceutical composition comprising a NIP to the diagnosed patient.

In certain embodiments, the NIP may be one of neonatal NET-Inhibitory Factor (nNIF), a pharmaceutically acceptable salt of nNIF, a nNIF analog, a pharmaceutically acceptable salt of a nNIF analog, a nNIF-Related Peptide (NRP), a pharmaceutically acceptable salt of a NRP, a NRP analog, and/or a pharmaceutically acceptable salt of a NRP analog. In various embodiments, the cancerous cells may include at least one of melanocytes, ovarian cells, stomach cells, lung cells, or another suitable type of cancerous cells. As discussed above, the pharmaceutical composition may substantially inhibit NET formation. Furthermore, the patient may be a mammal. In some embodiments, the patient may be a human.

The particular form of NIP, nNIF, nNIF analog, NRP, NRP analog, and/or salt thereof selected for inhibiting NETosis and/or NET formation can be prepared by a variety of techniques known for generating peptide products. For example, vertebrate forms of nNIF and NRP can be obtained by extraction from the natural source, using an appropriate combination of protein isolation techniques. Other techniques are also within the scope of this disclosure.

In certain embodiments, NIPs, nNIF, nNIF analogs, NRPs, NRP analogs, and/or salts thereof can be synthesized using standard techniques of peptide chemistry and can be assessed for inhibition of NETosis and/or NET formation activity. With respect to synthesis, the selected NIP, nNIF, nNIF analog, NRP, NRP analog, and/or salt thereof can be prepared by a variety of techniques for generating peptide products. Those NIPs, nNIF, nNIF analogs, NRPs, NRP analogs, and/or salts thereof that incorporate only L-amino acids can be produced in commercial quantities by application of recombinant DNA technology. For this purpose, DNA coding for the desired NIP, nNIF, nNIF analog, NRP, and/or NRP analog is incorporated into an expression vector and transformed into a host cell (e.g., yeast, bacteria, or a mammalian cell), which is then cultured under conditions appropriate for NIP, nNIF, nNIF analog, NRP, and/or NRP analog expression. A variety of gene expression systems have been adapted for this purpose, and typically drive expression of the desired gene from expression regulatory elements used naturally by the chosen host.

In an approach applicable to the production of a selected NIP, nNIF, nNIF analog, NRP, and/or NRP analog, and one that may be used to produce a NIP, nNIF, nNIF analog, NRP, and/or NRP analog that incorporates non-genetically encoded amino acids and N- and C-terminally derivatized forms, the techniques of automated peptide synthesis may be employed, general descriptions of which appear, for example, in Stewart and Young, Solid Phase Peptide Synthesis, 2nd Edition, 1984, Pierce Chemical Company, Rockford, Ill.; Bodanszky and Bodanszky, The Practice of Peptide Synthesis, 1984, Springer-Verlag, New York, N.Y.; and Applied Biosystems 430A User's Manual, 1987, ABI Inc., Foster City, Calif. In these techniques, a NIP, nNIF, nNIF analog, NRP, and/or NRP analog is grown from its C-terminal, resin-conjugated residue by the sequential addition of appropriately protected amino acids, using either the 9-fluorenylmethyloxycarbonyl (Fmoc) or tert-butyloxycarbonyl (t-Boc) protocols, as described for instance by Orskov, et al., FEBS Lett, 1989, 247(2): 193-196.

Once the desired NIP, nNIF, nNIF analog, NRP, and/or NRP analog has been synthesized, cleaved from the resin and fully deprotected, the peptide may then be purified to ensure the recovery of a single oligopeptide having the selected amino acid sequence. Purification may be achieved using any of the standard approaches, which include, but are not limited to, reversed-phase high-pressure liquid chromatography (RP-HPLC) on alkylated silica columns (e.g., C4-, C8-, or C18-silica). Such column fractionation is generally accomplished by running linear gradients (e.g., 10-90%) of increasing percentage organic solvent (e.g., acetonitrile, in aqueous buffer), usually containing a small amount (e.g., 0.1%) of pairing agent such as trifluoroacetic acid (TFA) or triethanolamine (TEA). Alternatively, ion-exchange HPLC can be employed to separate peptide species on the basis of their charge characteristics. Column fractions are collected, and those containing peptide of the desired and/or required purity are optionally pooled. In some embodiments, the NIP, nNIF, nNIF analog, NRP, and/or NRP analog may then be treated in the established manner to exchange the cleavage acid (e.g., TFA) with a pharmaceutically acceptable acid, such as acetic, hydrochloric, phosphoric, maleic, tartaric, succinic, and the like, to generate a pharmaceutically acceptable acid addition salt of the peptide.

Analogs of human NIPs, nNIF, and/or NRPs can be generated using standard techniques of peptide chemistry and can be assessed for inhibition of NETosis and/or NET formation activity, all according to the guidance provided herein. In some embodiments, the analogs are based, at least in part, upon the sequences of human nNIF (SEQ ID NO:1), CRISPP (SEQ ID NO:2), A1ATm$^{358}$ (SEQ ID NO:3), and/or HTRA1-CF (SEQ ID NO:4) as follows (wherein X can be any naturally occurring amino acid):

```
                                              (SEQ ID NO: 1)
KFNKPFVFLMIEQNTKSPLFMGKVVNPTQ (SEQ ID NO: 2)
MXIPPEVKFNKPFVFLMIDQNTKVPLFMGK (SEQ ID NO: 3)
MFLEAIPMSIPPEVKFNKPFVFLMIEQNTKSPLFMLKVVS (SEQ ID NO: 4)
SIPPEVKFNKPFVFLMIEQNTKSPLFMGKWNPTQK
```

Any substitution, addition, or deletion of an amino acid or amino acids of a NIP, nNIF, and/or NRP that does not destroy the NET-inhibitory activity of the NIP, nNIF, and/or NRP may be usefully employed in this disclosure. In certain embodiments, the NIP, nNIF, and/or NRP analogs are at least as active as the native human NIP, nNIF, and/or NRP. NET-inhibitory activity may be determined in vitro as described in this disclosure. In other embodiments, the NIP, nNIF, and/or NRP analog has one or more enhanced properties compared with the native human NIP, nNIF, and/or NRP. For example, such analogs may exhibit enhanced serum stability, enhanced receptor binding, and enhanced signal-transducing activity. Other modifications to NIPs, nNIF, nNIF analogs, NRPs, and/or NRP analogs that may usefully be employed in this disclosure are those which render the molecule resistant to oxidation.

A researcher may determine whether a particular NIP, nNIF, nNIF analog, NRP, NRP analog, and/or salt thereof may be used to treat an inflammatory disorder by administering the peptide or analog to individuals who have the inflammatory disorder. The researcher may then determine, using diagnostic biomarkers, whether the individuals thus treated show decreased inflammation and improvement of the inflammatory condition.

The disclosure also encompasses non-conservative substitutions of amino acids in any vertebrate NIP, nNIF, and/or NRP sequence, provided that the non-conservative substitutions occur at amino acid positions known to vary in NIPs, nNIF, and/or NRPs isolated from different species. Non-conserved residue positions are readily determined by aligning known vertebrate NIP, nNIF, and/or NRP sequences.

For administration to patients, the NIP, nNIF, nNIF analog, NRP, NRP analog, and/or salt thereof may be provided in pharmaceutically acceptable form (e.g., as a preparation that is sterile-filtered, e.g., through a 0.22p filter, and substantially pyrogen-free). It may be desired that the NIP, nNIF, and/or NRP peptide to be formulated migrates as a single or individualized peak on HPLC, exhibits uniform and authentic amino acid composition and sequence upon analysis thereof, and otherwise meets standards set by the various national bodies which regulate quality of pharmaceutical products.

The aqueous carrier or vehicle may be supplemented for use as an injectable with an amount of gelatin that serves to depot the NIP, nNIF, nNIF analog, NRP, NRP analog, and/or salt thereof at or near the site of injection, for its slow release to the desired site of action. Concentrations of gelatin effective to achieve the depot effect are expected to lie in the range from 10% to 20%. Alternative gelling agents, such as hyaluronic acid (HA), may also be useful as depoting agents.

The NIPs, nNIF, nNIF analogs, NRPs, NRP analogs, and/or salts thereof of the present disclosure may also be formulated as slow-release implantation formulations for extended and sustained administration of the NIP, nNIF, nNIF analog, NRP, NRP analog, and/or salt thereof. Examples of such sustained release formulations include composites of biocompatible polymers, such as poly(lactic acid), poly(lactic-co-glycolic acid), methylcellulose, hyaluronic acid, collagen, and the like. The structure, selection, and use of degradable polymers in drug delivery vehicles have been reviewed in several publications, including Domb et al., Polym Advan Technol, 1992, 3: 279-292. Additional guidance in selecting and using polymers in pharmaceutical formulations can be found in the text by Chasin and Langer (eds.), Biodegradable Polymers as Drug Delivery Systems, Vol. 45 of Dekker, Drugs and the Pharmaceutical Sciences, 1990, New York, N.Y. Liposomes may also be used to provide for the sustained release of a nNIF, nNIF analog, NRP, NRP analog, and/or salt thereof. Details concerning how to use and make liposomal formulations of drugs of interest can be found in, among other places, U.S. Pat. Nos. 4,944,948; 5,008,050; 4,921,706; 4,927,637; 4,452,747; 4,016,100; 4,311,712; 4,370,349; 4,372,949; 4,529,561; 5,009,956; 4,725,442; 4,737,323; and 4,920,016. Sustained release formulations may be of particular interest when it is desirable to provide a high local concentration of a NIP, nNIF, nNIF analog, NRP, NRP analog, and/or salt thereof (e.g., near the site of inflammation to inhibit NETosis and/or NET formation, etc.).

The NIPs, nNIF, nNIF analogs, NRPs, NRP analogs, and/or salts thereof of the present disclosure may also be incorporated into a device or devices, both implanted or topical, for extended and sustained administration of the NIP, nNIF, nNIF analog, NRP, NRP analog, and/or salt thereof.

For therapeutic use, the chosen NIP, nNIF, nNIF analog, NRP, NRP analog, and/or salt thereof may be formulated with a carrier that is pharmaceutically acceptable and is appropriate for delivering the peptide by the chosen route of administration. Suitable pharmaceutically acceptable carriers are those used conventionally with peptide-based drugs, such as diluents, excipients and the like. Reference may be made to Remington: The Science and Practice of Pharmacy, 22nd Edition, 2012, Pharmaceutical Press, London, UK. In certain embodiments, the compounds may be formulated for administration by infusion or by injection (e.g., subcutaneously, intramuscularly, or intravenously), and may be accordingly utilized as aqueous solutions in sterile and pyrogen-free form and optionally buffered to physiologically tolerable pH (e.g., a slightly acidic or physiological pH). Thus, the compounds may be administered in a vehicle such as distilled water, saline, phosphate buffered saline, or 5% dextrose solution. Water solubility of the NIP, nNIF, nNIF analog, NRP, NRP analog, and/or salt thereof may be enhanced, if desired, by incorporating a solubility enhancer, such as acetic acid.

Another aspect of the disclosure relates to methods of treating complications of prematurity.

In embodiments, this disclosure provides for methods of treating a patient having a complication of prematurity, the methods comprising administering to the patient an effective amount of a pharmaceutical composition comprising a NIP, or a pharmaceutically acceptable salt of a NIP, and a pharmaceutically acceptable carrier to reduce a pathological effect or symptom of the complication of prematurity, such as the prolonged need for oxygen support associated with neonatal chronic lung disease or the need for surgical intervention or prolonged total parenteral nutrition in infants that develop necrotizing enterocolitis.

In some embodiments, this disclosure provides for methods of treating a patient having a complication of prematurity, the methods comprising administering to the patient an effective amount of a pharmaceutical composition comprising a nNIF, or a pharmaceutically acceptable salt of a nNIF, and a pharmaceutically acceptable carrier to reduce a pathological effect or symptom of the complication of prematurity.

In other embodiments, the disclosure provides methods of treating a patient having a complication of prematurity, the methods comprising administering to the patient an effective amount of a pharmaceutical composition comprising a nNIF analog, or a pharmaceutically acceptable salt of a nNIF analog, and a pharmaceutically acceptable carrier to reduce a pathological effect or symptom of the complication of prematurity.

In yet other embodiments, the disclosure provides methods of treating a patient having a complication of prematurity, the methods comprising administering to the patient an effective amount of a pharmaceutical composition comprising a NRP, or a pharmaceutically acceptable salt of a NRP, and a pharmaceutically acceptable carrier to reduce a pathological effect or symptom of the complication of prematurity.

In still other embodiments, the disclosure provides methods of treating a patient having a complication of prematurity, the methods comprising administering to the patient an effective amount of a pharmaceutical composition comprising a NRP analog, or a pharmaceutically acceptable salt of a NRP analog, and a pharmaceutically acceptable carrier to reduce a pathological effect or symptom of the complication of prematurity.

In some embodiments, the patient may be a mammal. In certain embodiments, the patient may be a human.

In some embodiments, the complication of prematurity may at least partially involve or be at least partially caused by neutrophil extracellular trap (NET) formation and/or NETosis. In certain embodiments, the pharmaceutical composition may substantially inhibit NET formation and/or NETosis. In other embodiments, the pharmaceutical composition may inhibit or substantially inhibit NET-mediated inflammatory tissue damage.

In some embodiments, the complication of prematurity may be one or more of, but not limited to, necrotizing enterocolitis (NEC), respiratory distress syndrome (RDS), pneumonia, bronchopulmonary dysplasia (BPD), neonatal chronic lung disease (CLD), neurodevelopmental delay, retinopathy of prematurity (ROP), and/or sepsis.

A further aspect of the disclosure relates to methods of prophylaxis against inflammatory disorders.

In some embodiments, the disclosure provides for methods of prophylaxis against an inflammatory disorder in a patient at risk of developing an inflammatory disorder, the methods comprising administering to the patient an effective amount of a pharmaceutical composition comprising a NIP, or a pharmaceutically acceptable salt of a NIP, and a pharmaceutically acceptable carrier to reduce the risk of developing a pathological effect or symptom of the inflammatory disorder.

In some embodiments, the disclosure provides for methods of prophylaxis against an inflammatory disorder in a patient at risk of developing an inflammatory disorder, the methods comprising administering to the patient an effective amount of a pharmaceutical composition comprising a nNIF, or a pharmaceutically acceptable salt of a nNIF, and a pharmaceutically acceptable carrier to reduce the risk of developing a pathological effect or symptom of the inflammatory disorder.

In other embodiments, the disclosure provides for methods of prophylaxis against an inflammatory disorder in a patient at risk of developing an inflammatory disorder, the methods comprising administering to the patient an effective amount of a pharmaceutical composition comprising a nNIF analog, or a pharmaceutically acceptable salt of a nNIF analog, and a pharmaceutically acceptable carrier to reduce the risk of developing a pathological effect or symptom of the inflammatory disorder.

In yet other embodiments, the disclosure provides for methods of prophylaxis against an inflammatory disorder in a patient at risk of developing an inflammatory disorder, the methods comprising administering to the patient an effective amount of a pharmaceutical composition comprising a NRP, or a pharmaceutically acceptable salt of a NRP, and a pharmaceutically acceptable carrier to reduce the risk of developing a pathological effect or symptom of the inflammatory disorder.

In still other embodiments, the disclosure provides for methods of prophylaxis against an inflammatory disorder in a patient at risk of developing an inflammatory disorder, the methods comprising administering to the patient an effective amount of a pharmaceutical composition comprising a NRP analog, or a pharmaceutically acceptable salt of the NRP analog, and a pharmaceutically acceptable carrier to reduce the risk of developing a pathological effect or symptom of the inflammatory disorder.

In some embodiments, the patient may be a mammal, including a human.

In some embodiments, the inflammatory disorder may at least partially involve or be at least partially caused by neutrophil extracellular trap (NET) formation and/or NETosis. In some embodiments, the inflammatory disorder may be an acute inflammatory disorder. In other embodiments, the inflammatory disorder may be a chronic inflammatory disorder. In other embodiments, the inflammatory disorder may be an autoimmunity disorder. In yet other embodiments, the inflammatory disorder may be a disorder of coagulation.

In some embodiments, the inflammatory disorder may be one or more of, but not limited to, the inflammatory disorders defined and/or listed above.

In some embodiments, the pharmaceutical composition may substantially inhibit NET formation and/or NETosis. In other embodiments, the pharmaceutical composition may inhibit or substantially inhibit NET-mediated inflammatory tissue damage.

Another aspect of the disclosure relates to methods of prophylaxis against complications of prematurity.

In embodiments, this disclosure provides methods of prophylaxis against complications of prematurity in a patient at risk of developing a complication of prematurity, the methods comprising administering to the patient an effective amount of a pharmaceutical composition comprising a neonatal NIP, or a pharmaceutically acceptable salt of a NIP, and a pharmaceutically acceptable carrier to reduce the risk of developing a pathological effect or symptom of the complication of prematurity.

In some embodiments, this disclosure provides methods of prophylaxis against complications of prematurity in a patient at risk of developing a complication of prematurity, the methods comprising administering to the patient an effective amount of a pharmaceutical composition comprising a neonatal nNIF, or a pharmaceutically acceptable salt of a nNIF, and a pharmaceutically acceptable carrier to reduce the risk of developing a pathological effect or symptom of the complication of prematurity.

In certain embodiments, the disclosure provides methods of prophylaxis against complications of prematurity in a patient at risk of developing a complication of prematurity, the methods comprising administering to the patient an effective amount of a pharmaceutical composition comprising a nNIF analog, or a pharmaceutically acceptable salt of a nNIF analog, and a pharmaceutically acceptable carrier to reduce the risk of developing a pathological effect or symptom of the complication of prematurity.

In yet other embodiments, the disclosure provides methods of prophylaxis against complications of prematurity in a patient at risk of developing a complication of prematurity, the methods comprising administering to the patient an effective amount of a pharmaceutical composition comprising a nNIF-Related Peptide (NRP), or a pharmaceutically acceptable salt of a NRP, and a pharmaceutically acceptable carrier to reduce the risk of developing a pathological effect or symptom of the complication of prematurity.

In still other embodiments, the disclosure provides methods of prophylaxis against complications of prematurity in a patient at risk of developing a complication of prematurity, the methods comprising administering to the patient an effective amount of a pharmaceutical composition comprising a NRP analog, or a pharmaceutically acceptable salt of a NRP analog, and a pharmaceutically acceptable carrier to reduce the risk of developing a pathological effect or symptom of the complication of prematurity.

In some embodiments, the patient may be a mammal, including a human.

In some embodiments, the complication of prematurity may at least partially involve or be at least partially caused by neutrophil extracellular trap (NET) formation and/or NETosis. In other embodiments, the pharmaceutical composition may substantially inhibit NET formation and/or NETosis. In yet other embodiments, the pharmaceutical composition may inhibit or substantially inhibit NET-mediated inflammatory tissue damage.

In other embodiments, the complication of prematurity may be one or more of, but not limited to, necrotizing enterocolitis (NEC), respiratory distress syndrome (RDS), pneumonia, bronchopulmonary dysplasia (BPD), neonatal chronic lung disease (CLD), neurodevelopmental delay, retinopathy of prematurity (ROP), and/or sepsis.

In a further aspect, this disclosure relates to pharmaceutical compositions comprising NIPs.

In some embodiments, the pharmaceutical composition may comprise neonatal NET-Inhibitory Factor (nNIF), or a pharmaceutically acceptable salt of a nNIF, and a pharmaceutically acceptable carrier. In another embodiment, the pharmaceutical composition may comprise a nNIF analog, or a pharmaceutically acceptable salt of a nNIF analog, and a pharmaceutically acceptable carrier. In yet other embodiments, the pharmaceutical composition may comprise a nNIF-Related Peptide (NRP), or a pharmaceutically acceptable salt of a NRP, and a pharmaceutically acceptable carrier. In still other embodiments, the pharmaceutical composition may comprise a NRP analog, or a pharmaceutically acceptable salt of a NRP analog, and a pharmaceutically acceptable carrier.

In certain embodiments, the pharmaceutical composition may comprise nNIF (e.g., human nNIF), or a salt thereof, and the nNIF, or the salt thereof, may comprise at least a portion of the amino acid sequence:

(SEQ ID NO: 1)
KFNKPFVFLMIEQNTKSPLFMGKVVNPTQ

In various embodiments, the pharmaceutical composition may comprise CRISPP, or a salt thereof, and the CRISPP, or the salt thereof, may comprise at least a portion of the amino acid sequence:

(SEQ ID NO: 2)
MXIPPEVKFNKPFVFLMIDQNTKVPLFMGK

In some embodiments, the pharmaceutical composition may comprise A1ATm$^{358}$, or a salt thereof, and the A1ATm$^{358}$, or the salt thereof, may comprise at least a portion of the amino acid sequence:

(SEQ ID NO: 3)
MFLEAIPMSIPPEVKFNKPFVFLMIEQNTKSPLFMLKVVS

In certain embodiments, the pharmaceutical composition may comprise HTRA1-CF, or a salt thereof, and the HTRA1-CF, or the salt thereof, may comprise at least a portion of the amino acid sequence:

(SEQ ID NO: 4)
SIPPEVKFNKPFVFLMIEQNTKSPLFMGKWNPTQK

In other embodiments, at least one amino acid of the nNIF, the salt of the nNIF, the nNIF analog, the salt of the nNIF analog, the NRP, the salt of the NRP, the NRP analog, the salt of the NRP analog, the CRISPP, the salt of the CRISPP, the A1ATm$^{358}$, the salt of the A1ATm$^{358}$, the HTRA1-CF, or the salt of the HTRA1-CF may be bound to a chemical modifier. In some embodiments, the chemical modifier may be selected from at least one of a lipid, a polyethylene glycol (PEG), a saccharide, or any other suitable molecule. Other chemical modifications of the pharmaceutical composition—for example, cationization, methylization, and cyclization—are also within the scope of this disclosure.

Attachment of a lipid to the peptide (lipidization) may increase lipophilicity of the pharmaceutical composition.

Attachment of a PEG to the peptide (PEGylation) increases the molecular weight of the peptide. In some embodiments, PEGylation may improve solubility of the pharmaceutical composition. In other embodiments, PEGylation may reduce dosage frequency and/or toxicity of the pharmaceutical composition. In other embodiments, PEGylation may extend circulating life of the pharmaceutical composition, and/or extend stability of the pharmaceutical composition, and/or may enhance protection of the pharmaceutical composition from proteolytic degradation. PEGylation may also reduce immunogenicity and/or antigenicity of the pharmaceutical composition.

Attachment of one or more saccharides to the peptide (glycosylation) may serve a variety of functional and/or structural roles in the pharmaceutical composition. Glycosylation may improve delivery of the pharmaceutical composition to a target or to targets of choice. Glycosylation may also reduce the toxicity of the pharmaceutical composition.

In some embodiments, the pharmaceutical composition comprising the nNIF, the salt of the nNIF, the nNIF analog, the salt of the nNIF analog, the NRP, the salt of the NRP, the NRP analog, or the salt of the NRP analog may be present in an amount effective to inhibit, or to substantially inhibit, damage selected from at least one of inflammatory tissue injury and/or inflammatory vascular injury.

In some embodiments, the pharmaceutical composition comprising the nNIF, the salt of the nNIF, the nNIF analog, the salt of the nNIF analog, the NRP, the salt of the NRP, the NRP analog, or the salt of the NRP analog may not globally depress functions of PMNs. As discussed above, the functions of PMNs include, but are not limited to, chemotaxis, phagocytosis, reactive oxygen species (ROS) generation, cytokine/chemokine synthesis and secretion, NET formation/NETosis, and/or intracellular/extracellular bacterial killing. In certain embodiments, the pharmaceutical composition may not inhibit or substantially inhibit PMN phagocytosis. In other embodiments, the pharmaceutical composition may not inhibit or substantially inhibit PMN chemotaxis. In yet other embodiments, the pharmaceutical composition may not inhibit or substantially inhibit generation of ROS. In other embodiments, the pharmaceutical composition may not inhibit or substantially inhibit PMN intracellular bacterial killing.

In some embodiments, the pharmaceutical composition may comprise a nNIF analog, a salt of a nNIF analog, a NRP analog, or a salt of a NRP analog, and the analog or the salt of the analog may not be a naturally occurring analog or salt of the analog.

In some embodiments, the pharmaceutical composition may be present in an amount effective to inhibit, or to substantially inhibit, NET formation and/or NETosis. In some embodiments, the NET formation and/or NETosis may be stimulated by a bacterium, a fungus, a parasite, a virus, and/or any other appropriate stimulator of NET formation and/or NETosis. In certain embodiments, the virus may be a hemorrhagic fever virus. Hemorrhagic fever viruses are described, e.g., in Borio et al., JAMA, 2002, 287(18): 2391-2405, and include, but are not limited to, filoviruses such as Ebola virus and Marburg virus, arenaviruses such as Lassa virus, hantaviruses, and flaviviruses such as dengue virus and yellow fever virus. In other embodiments, the NET formation and/or NETosis may be stimulated by one or more bacterial species, including, but not limited to, *Bacillus* species, *Escherichia* species, *Francisella* species, *Streptococcus* species, *Staphylococcus* species, *Yersinia* species, and/or any other appropriate gram-negative or gram-positive bacterium or bacteria. In embodiments, the *Bacillus* species may be *Bacillus anthracis* (anthrax). In embodiments, the *Escherichia* species may be *Escherichia coli*. In embodiments, the *Francisella* species may be *Francisella tularensis* (tularemia). In embodiments, the *Staphylococcus* species may be *Staphylococcus aureus*.

In other embodiments, the NET formation and/or NETosis may be stimulated by beta-defensin 1, HIV-1, lipopolysaccharide (LPS), phorbol myristate acetate (PMA), and/or *Staphylococcus aureus* alpha-toxin.

In some embodiments, the pharmaceutical composition may comprise a NRP and/or a NRP analog. In certain embodiments, the pharmaceutical composition may comprise Cancer-Associated SCM-Recognition, Immune Defense Suppression, and Serine Protease Protection Peptide (CRISPP) and/or a CRISPP analog. In various embodiments, the pharmaceutical composition may comprise A1ATm$^{358}$ and/or an A1ATm$^{358}$ analog. In some embodiments, the pharmaceutical composition may comprise HTRA1-CF and/or a HTRA1-CF analog. In some other embodiments, the pharmaceutical may comprise another NRP. In certain embodiments, the NRP may be an isolated and purified component of umbilical cord blood.

In an additional aspect, this disclosure relates to compositions for inhibiting the formation of NETs and/or NETosis in a mammal.

In some embodiments, a composition for inhibiting the formation of NETs and/or NETosis in a mammal may comprise a nNIF, a pharmaceutically acceptable salt of the nNIF, a nNIF analog, a pharmaceutically acceptable salt of the nNIF analog, a NRP, a pharmaceutically acceptable salt of the NRP, a NRP analog, or a pharmaceutically acceptable salt of the NRP analog, and a pharmaceutically acceptable carrier. In certain embodiments the mammal may be a human.

In a further aspect, this disclosure relates to a NET-Inhibitory Peptide (NIP).

In some embodiments, the NIP may be an isolated and purified nNIF protein comprising SEQ ID NO:1. In certain other embodiments, the isolated and purified nNIF protein may comprise at least 24 contiguous amino acids of SEQ ID NO:1. In yet other embodiments, the isolated and purified nNIF protein may comprise at least 12 contiguous amino acids of SEQ ID NO:1. In still other embodiments, the isolated and purified nNIF protein may comprise at least six contiguous amino acids of SEQ ID NO:1.

In certain embodiments, the NIP may be an isolated and purified nNIF protein wherein the sequence may be at least 80% identical to SEQ ID NO:1. In other embodiments, the isolated and purified nNIF may be at least 60% identical to SEQ ID NO:1. In yet other embodiments, the isolated and purified nNIF may be at least 40% identical to SEQ ID NO:1. In still other embodiments, the isolated and purified nNIF may be at least 20% identical to SEQ ID NO:1.

In some embodiments, the NIP may be an isolated and purified CRISPP protein comprising SEQ ID NO:2. In certain other embodiments, the isolated and purified CRISPP protein may comprise at least 24 contiguous amino acids of SEQ ID NO:2. In yet other embodiments, the isolated and purified CRISPP protein may comprise at least 12 contiguous amino acids of SEQ ID NO:2. In still other embodiments, the isolated and purified CRISPP protein may comprise at least six contiguous amino acids of SEQ ID NO:2.

In certain embodiments, the NIP may be an isolated and purified CRISPP protein wherein the sequence may be at least 80% identical to SEQ ID NO:2. In other embodiments, the isolated and purified CRISPP may be at least 60% identical to SEQ ID NO:2. In yet other embodiments, the isolated and purified CRISPP may be at least 40% identical to SEQ ID NO:2. In still other embodiments, the isolated and purified CRISPP may be at least 20% identical to SEQ ID NO:2.

In some embodiments, the NIP may be an isolated and purified A1ATm$^{358}$ protein comprising SEQ ID NO:3. In certain other embodiments, the isolated and purified A1ATm$^{358}$ protein may comprise at least 24 contiguous amino acids of SEQ ID NO:3. In yet other embodiments, the isolated and purified A1ATm$^{358}$ protein may comprise at least 12 contiguous amino acids of SEQ ID NO:3. In still other embodiments, the isolated and purified A1ATm$^{358}$ protein may comprise at least six contiguous amino acids of SEQ ID NO:3.

In certain embodiments, the NIP may be an isolated and purified A1ATm$^{358}$ protein wherein the sequence may be at least 80% identical to SEQ ID NO:3. In other embodiments, the isolated and purified A1ATm$^{358}$ may be at least 60% identical to SEQ ID NO:3. In yet other embodiments, the isolated and purified A1ATm$^{358}$ may be at least 40% identical to SEQ ID NO:3. In still other embodiments, the isolated and purified A1ATm$^{358}$ may be at least 20% identical to SEQ ID NO:3.

In some embodiments, the NIP may be an isolated and purified HTRA1-CF protein comprising SEQ ID NO:4. In certain other embodiments, the isolated and purified HTRA1-CF protein may comprise at least 24 contiguous amino acids of SEQ ID NO:4. In yet other embodiments, the isolated and purified HTRA1-CF protein may comprise at least 12 contiguous amino acids of SEQ ID NO:4. In still other embodiments, the isolated and purified HTRA1-CF protein may comprise at least six contiguous amino acids of SEQ ID NO:4.

In certain embodiments, the NIP may be an isolated and purified HTRA1-CF protein wherein the sequence may be at least 80% identical to SEQ ID NO:4. In other embodiments, the isolated and purified HTRA1-CF may be at least 60% identical to SEQ ID NO:4. In yet other embodiments, the isolated and purified HTRA1-CF may be at least 40% identical to SEQ ID NO:4. In still other embodiments, the isolated and purified HTRA1-CF may be at least 20% identical to SEQ ID NO:4.

In another aspect, this disclosure relates to a nNIF protein analog, a CRISPP protein analog, an A1ATm$^{358}$ analog, and/or a HTRA1-CF analog. In some embodiments, the nNIF protein analog may be an isolated and purified nNIF analog, the CRISPP protein analog may be an isolated and purified CRISPP analog, the A1ATm$^{358}$ protein analog may be an isolated and purified A1ATm$^{358}$ analog, and/or the HTRA1-CF protein analog may be an isolated and purified HTRA1-CF analog.

An effective dosage and treatment protocol may be determined by conventional means, e.g., by starting with a low dose in laboratory animals and then increasing the dosage while monitoring the effects, and systematically varying the dosage regimen as well. Numerous factors may be taken into consideration by a clinician when determining an optimal dosage for a given subject. Primary among these is whether any NIPs are normally circulating in the plasma and, if so, the amount of any such NIPs. Additional factors include the size of the patient, the age of the patient, the general condition of the patient, the particular disorder being treated, the severity of the disorder, the presence of other drugs in the patient, and the in vivo activity of the NIP, nNIF, nNIF analog, NRP, NRP analog, salt thereof, and the like. The trial dosages may be chosen after consideration of the results of animal studies and the clinical literature.

There are many specific therapeutic regimens used to assess whether a molecule has a desired effect. A researcher faced with the task of determining whether a particular NIP, nNIF, nNIF analog, NRP, and/or NRP analog may be used for inhibition of NETosis and/or NET formation would choose the appropriate regimen to make this determination.

Delivery methods and formulations useful for administering peptides to individuals are known in the art, and a skilled person would be able to determine the suitability of any particular method of delivery of a peptide to an individual for particular circumstances. For the purposes of illustration only, the following examples of methods and formulations for administering peptides to individuals are provided.

Peptides may be administered to individuals orally; however, actions of the digestive system may reduce the bioavailability of the peptide. In order to increase peptide oral bioavailability, peptides may be administered in formulations containing enzyme inhibitors, or the peptides may be administered as part of a micelle, nanoparticle, or emulsion in order to protect the peptide from digestive activity.

Peptides may also be administered by means of an injection. The peptides may be injected subcutaneously, intramuscularly, or intravenously. Further disclosure regarding methods of administering peptides through injection is found, e.g., in U.S. Pat. No. 5,952,301.

Peptides may further be administered by pulmonary delivery. A dry powder inhalation system may be used, wherein peptides are absorbed through the tissue of the lungs, allowing delivery without injection, while bypassing the potential reduction in bioavailability seen with oral administration. See Onoue et al., Expert Opin Ther Pat, 2008, 18: 429.

For use in inhibiting NETosis and/or NET formation in a mammal, including a human, the present disclosure provides in one of its aspects a package or kit, in the form of a sterile-filled vial or ampoule, that contains a NETosis and/or NET formation inhibiting amount of a NIP, nNIF, nNIF analog, NRP, NRP analog, and/or salt thereof in either unit dose or multi-dose amounts, wherein the package or kit incorporates a label instructing use of its contents for the inhibition of such NETosis and/or NET formation. In various embodiments, the package or kit contains the NIP, nNIF, nNIF analog, NRP, NRP analog, and/or salt thereof and the desired carrier, as an administration-ready formulation. Alternatively, and according to some other embodiments, the package or kit provides the NIP, nNIF, nNIF analog, NRP, NRP analog, and/or salt thereof in a form, such as a lyophilized form, suitable for reconstitution in a suitable carrier, such as phosphate-buffered saline.

In one embodiment, the package or kit is a sterile-filled vial or ampoule containing an injectable solution which comprises an effective, NETosis and/or NET formation inhibiting amount of NIP, nNIF, nNIF analog, NRP, NRP analog and/or salt thereof dissolved in an aqueous vehicle.

Inflammatory pathways and immune mechanisms have checkpoints and modulatory brakes that prevent inappropriate initiation or unregulated propagation of effector events, which could otherwise cause pathologic collateral injury to the host (see Nathan C., *Nature*. 2002; 420 (6917):846-52 and Medzhitov R., *Nature*. 2008; 454 (7203):428-35). Tight control and modulation of inflammatory responses appear to be particularly important in the fetus and neonate, but the cellular and molecular mechanisms involved remain incompletely defined (see Dowling D J, et al., *Trends in immunology*. 2014; 35 (7):299310; Adkins B., et al., *Immunologic research*. 2013; 57 (1-3):246-57; Elahi S, et al., *Nature*. 2013; 504 (7478):158-62; Arck P C, et al., *Nature medicine*. 2013; 19 (5):548-56; and Levy O., *Nat Rev Immunol*. 2007; 7 (5):379-90). nNIF in umbilical cord blood and A1ATm$^{358}$ in the placental matrix may represent regulatory factors that modulate NETosis in the perinatal milieu. Placental IL-8, a NETosis-inducing chemokine (see Fuchs T A, et al., *J Cell Biol*. 2007; 176 (2):231-41), and syncytiotrophoblast microparticles trigger NET formation in vitro, and NETs are present in placentas of women with pre-eclampsia (see Gupta A K, et al., *Hum Immunol*. 2005; 66 (11):1146-54). Thus NET-inducing stimuli appear to be generated at the maternal-fetal interface, suggesting that unregulated NET formation can cause inflammatory pathology in the fetomaternal environment. Excessive intrapartum NET formation could also have additional negative consequences, including long-term neonatal immune dysregulation (see Brinkmann V, et al., *J Cell Biol*. 2012; 198 (5):773-83; Yipp B G, et al., Blood. 2013; 122 (16):2784-94; Dowling D J, et al., 2014; 35 (7):299310; Adkins B. et al., Immunologic research. 2013; 57 (1-3):246-57; Arck P C, et al., Nature medicine. 2013; 19 (5):548-56; and Sangaletti S, et al., Blood. 2012; 120 (15):3007-18). Immediately after delivery, the neonate is at risk for NET-mediated vascular injury and thrombosis (see Sorensen O E, et al., Journal of clinical investigation. 2016; 126 (5):1612-20; Brinkmann V, et al., J Cell Biol. 2012; 198 (5):773-83; and Yipp B G, et al., Blood. 2013; 122 (16):2784-94; Kolaczkowska E, et al., Nature communications. 2015; 6 (6673); Clark S R, et al., Nature medicine. 2007; 13 (4):463-9; Fuchs T A, et al., Proc Natl Acad Sci USA. 2010; 107 (36):15880-5; and Saffarzadeh M, et al., Curr Opin Hematol. 2013; 20 (1):3-9) triggered by microbial colonization (see Palmer C, et al., PLoS biology. 2007; 5 (7):e177 and Jost T, et al., PloS one. 2012; 7 (8):e44595) and consequent neutrophil mobilization (see Deshmukh H S, et al., Nat Med. 2014; 20 (5):524-30) if NET formation is not tightly controlled. nNIF in neonatal plasma and the related NRP A1ATm$^{358}$ in the placental interstitium (see Niemann M A, et al., Journal of cellular biochemistry. 1997; 66 (3):346-57) represent potential "stop signals" (see Nathan C., Nature. 2002; 420 (6917):846-52) that selectively limit NET formation before and immediately after birth. Rapid development of full NET competency by neonatal PMNs (see FIGS. 1A-1D) and decreased nNIF in neonatal blood in the first few days of extrauterine life parallel establishment of the resident microbiota of the human infant (see Palmer C, et al., PLoS biology. 2007; 5 (7):e177 and Jost T, et al., PloS one. 2012; 7 (8):e44595) and suggest that these are regulated features of immune development. In initial screens, nNIF was not detected, or was minimally present, in plasma samples from healthy adults or adult patients with chronic inflammatory syndromes (see FIG. 2B). This suggests, but without being bound any specific theory, that nNIF expression may largely be a feature of the fetus and neonate, as are certain other immunoregulatory mechanisms (see Dowling D J, et al., Trends in immunology. 2014; 35 (7):299310; Adkins B., Immunologic research. 2013; 57 (1-3):246-57; and Elahi S, et al., Nature. 2013; 504 (7478): 158-62).

Studies and previous observations suggest that nNIF and A1ATm$^{358}$ are generated by proteolytic cleavage of A1AT in the placenta. A1AT is abundant in human placental tissue compartments (see Castellucci M, et al., Cell and tissue research. 1994; 278 (2):283-9 and Frochaux V, et al., PloS one. 2014; 9 (10):e109483). It has been proposed that progressive proteolytic cleavage of A1AT occurs in the placenta, and proteases that mediate enzymatic fragmentation of A1AT to A1ATm$^{358}$ in vitro are known (see Niemann M A, et al., Matrix. 1992; 12 (3):233-41; Niemann M A, et al., Biochim Biophys Acta. 1997; 1340 (1):12330; and Pei D, et al., J Biol Chem. 1994; 269 (41):25849-55), although a specific placental protease has not been identified. A protease that is increased in human placental syncytiotrophoblasts in the third trimester of pregnancy, high temperature requirement protease 1, cleaves A1AT in the carboxy terminus (see Frochaux V, et al., PloS one. 2014; 9 (10): e109483). These findings, without being bound by any specific theory, suggest a mechanism for generation of biologically-active fragments of A1AT in the placenta that would no longer be active after delivery and separation of the neonate.

In addition to nNIF and A1ATm$^{358}$, CRISPP was identified as a NRP. CRISPP-related peptides have been detected in plasma from patients with multiple types of cancer (see Cercek L, et al., Cancer Detect Prev. 1992; 16 (5-6):305-19; Cercek L, et al., Cancer Detect Prev. 1993; 17 (3):433-45; and Cercek L, et al., Cancer Detect Prev. 1993; 17 (3):447-54) but have not been linked to regulation of NETosis. NET formation facilitates experimental metastasis (see Cools-Lartigue J, et al., J Clin Invest. 2013; 123 (8):3446-58), and may also contribute to outcomes in cancer-associated infection and sepsis. Thus, endogenous CRISPP-related peptides may have significant influences on neoplastic complications by inhibiting formation of NETs.

Figure 13:
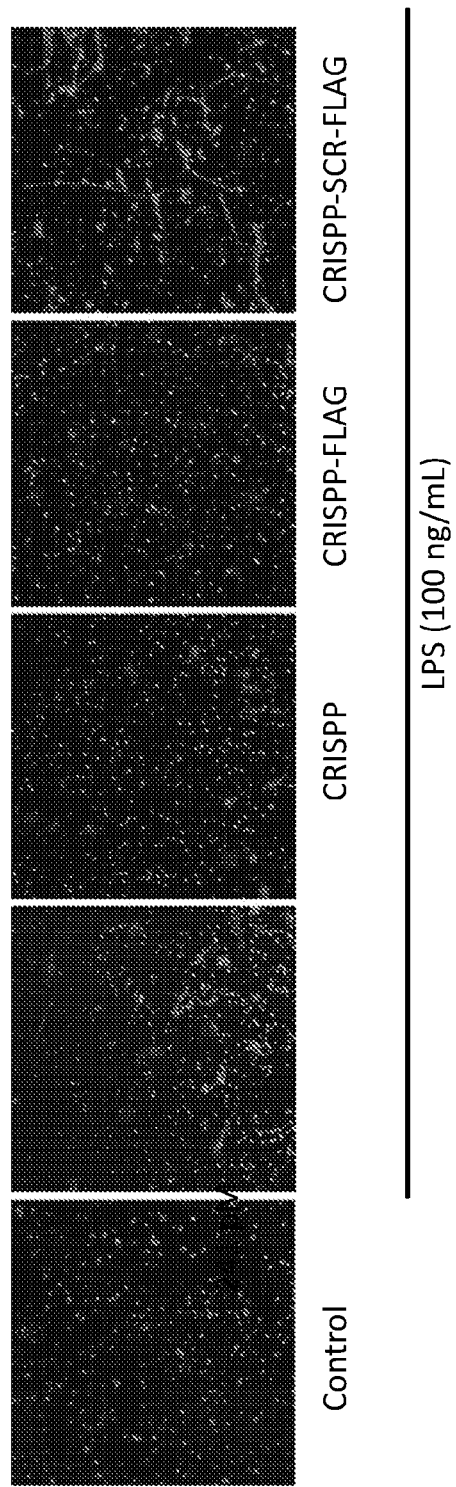
FIG. 13 is a series of images depicting that FLAG-tagged CRISPP inhibits NET formation by LPS-activated neutrophils. Adult neutrophils were preincubated for 30 minutes in medium alone or with CRISPP, FLAG-tagged CRISPP (CRISPP-FLAG), or FLAG-tagged CRISPP-SCR (CRISPP-SCR-FLAG) (1 nM for all); stimulated with LPS (100 ng/mL); and incubated for 1 hour, followed by live cell imaging as in FIG. 1A to assess NET formation (red fluorescence=NETs; green fluorescence=nuclear DNA; 20× magnification). Inhibition of NET formation by CRISPP-FLAG and CRISPP but not CRISPP-SCR-FLAG was seen in three separate experiments with neutrophils from different donors.

It was found that nNIF and CRISPP inhibit in vitro NET deployment induced by S. aureus, the bacterial toxin LPS, a previously-unrecognized viral trigger, dengue, a host-derived DAMP, heme, and the potent pharmacologic agonist, PMA. This analysis indicates that NRPs interrupt NET formation triggered by diverse stimuli (e.g., fungal agonists, etc.) that may be mediated by distinct activation pathways (see Sorensen O E, et al., Journal of clinical investigation. 2016; 126 (5):1612-20). Furthermore, nNIF and CRISPP inhibited in vivo NET formation in a murine model of E. coli peritonitis (see FIGS. 8A-8F). Here, NET formation is likely induced by the bacteria, LPS, and host-derived mediators, suggesting that NRPs can inhibit NET deployment by neutrophils stimulated by multiple agonists that act in combinational fashion in a complex inflammatory milieu and that, perhaps, induce NET formation via more than one pathway simultaneously (see Yipp B G, et al., Blood. 2013; 122 (16):2784-94). Validation of nNIF and CRISPP as inhibitors of NET deployment in this model (see FIGS. 8A-8F) also complements analysis of in vitro inhibition (see FIGS. 3A-3E) since it is suggested that pathways to NET formation vary in vivo and in vitro (see Sorensen O E, et al., Journal of clinical investigation. 2016; 126 (5):1612-20).

nNIF and CRISPP were utilized as probes to explore the mechanism(s) by which NRPs inhibit NET formation. While NETosis induced by a number of agonists involves ROS generation (see Sorensen O E, et al., Journal of clinical investigation. 2016; 126 (5):1612-20; Brinkmann V, et al., J Cell Biol. 2012; 198 (5):773-83; Yipp B G, et al., Blood. 2013; 122 (16):2784-94; Brinkmann V, et al., Science. 2004; 303 (5663):1532-5; Papayannopoulos V, et al., J Cell Biol. 2010; 191 (3):677-91; Lood C, et al., Nature medicine. 2016; 22 (2):146-53; Branzk N, et al., Semin Immunopathol. 2013; 35 (4):513-30; and Schauer C, et al., Nature medicine. 2014; 20 (5):511-7), current (see FIG. 6B) and previous (see Yost C C, et al., Blood. 2009; 113 (25):6419-27) experiments indicate that NRPs act at a different step or steps. Based on studies to date, chromatin decondensation plays a role in NET deployment regardless of the agonist (see Sorensen O E, et al., Journal of clinical investigation. 2016; 126 (5): 1612-20; Brinkmann V, et al., J Cell Biol. 2012; 198 (5):773-83; Yipp B G, et al., Blood. 2013; 122 (16):2784-94; Yipp B G, et al., Nature medicine. 2012; 18 (9):1386-93; Papayannopoulos V, et al., J Cell Biol. 2010; 191 (3):677-91; Farley K, et al., Journal of immunology. 2012; 189 (9):4574-81; Pilsczek F H, et al., Journal of immunology. 2010; 185 (12):7413-25; and Branzk N, et al., Semin immunopathol. 2013; 35 (4):513-30). It has been found that nNIF and CRISPP inhibit loss of lobules and expansion of nuclei in PMA-stimulated neutrophils (see FIGS. 7A, 12A, and 12B) in an assay based on earlier studies of chromatin decondensation in NETosis (see Papayannopoulos V, et al., J Cell Biol. 2010; 191 (3):677-91). Neutrophil heterochromatin decondensation is mediated by PAD4, which catalyzes conversion of histone arginines to citrullines with consequent weakening of histone-DNA binding and unwinding of nucleosomes (see Sorensen O E, et al., Journal of clinical investigation. 2016; 126 (5):1612-20; Wang Y, et al., J Cell Biol. 2009; 184 (2):205-13; Li P, et al., *J Exp Med.* 2010; 207 (9):1853-62; and Kolaczkowska E, et al., *Nature communications.* 2015; 6 (6673)). In a cell-free assay of PAD4 activity based on deimination of a synthetic substrate, inhibition by nNIF was found in parallel with Cl-amidine, an established PAD4 inhibitor (see FIG. 7C). This is consistent with inhibition of nuclear decondensation by each agent (see FIG. 7A). In live, intact human neutrophils activated with PMA, nNIF and Cl-amidine inhibited nuclear histone citrullination, which occurred before nuclear decondensation (see FIG. 7D). In preliminary assays, CRISPP also inhibited PAD4 activity and nuclear histone citrullination. Together, these findings indicate that NRPs inhibit nuclear decondensation and NET formation at least in part by inhibiting PAD4 activity and nuclear histone deimination. NE is also thought to play a role in NETosis (see Sorensen O E, et al., *Journal of clinical investigation.* 2016; 126 (5):1612-20). NE mediates nuclear histone cleavage in PMA-activated neutrophils (see Papayannopoulos V, et al., *J Cell Biol.* 2010; 191 (3):677-91); inhibitors of NE activity block nuclear decondensation (see Sorensen O E, et al., *Journal of clinical investigation.* 2016; 126 (5):1612-20; Papayannopoulos V, et al., *J Cell Biol.* 2010; 191 (3):677-91; and Farley K, et al., *Journal of immunology.* 2012; 189 (9):4574-81) (see FIGS. 12A and 12B) and NET formation in vivo (see Cools-Lartigue J, et al., *J Clin Invest.* 2013; 123 (8):3446-58); endogenous regulators of NE influence NETosis (see Farley K, et al., *Journal of immunology.* 2012; 189 (9):4574-81 and Zabieglo K, et al., *Journal of leukocyte biology.* 2015; 98 (1):99-106); and NET generation is impaired in NE-deficient mice (see Kolaczkowska E, et al., *Nature communications.* 2015; 6 (6673)). Nevertheless, it was found that NRPs do not directly inhibit NE activity in in vitro assays (see FIGS. 12A and 12B). NRPs, however, may interrupt NE-mediated events in NETosis pathways in other ways. A FLAG-tagged construct of CRISPP that inhibits NET formation (see FIG. 13) was internalized by activated PMNs (see FIG. 7E) and was closely localized near NE in the neutrophil cytoplasm, suggesting, without being bound by a specific theory, that NRPs may have more than one site and mechanism of action.

nNIF and CRISPP effectively inhibit NET formation by both human and murine neutrophils (see FIGS. 3A-3E and 8A-8F), whereas it has been reported that synthetic inhibitors of PAD4 have differential efficacy as inhibitors of NETosis by human and mouse neutrophils (see Lewis H D, et al., Nature chemical biology. 2015). In initial analysis of outcomes when NRPs are administered in vivo, nNIF and CRISPP were examined in mice challenged with LPS, which causes sterile systemic inflammation, NET formation, organ damage, and mortality (see Clark S R, et al., *Nature medicine.* 2007; 13 (4):463-9; McDonald B, et al., *Cell host & microbe.* 2012; 12 (3):32433; Tanaka K, et al., *PloS one.* 2014; 9 (11):e111888; and Wildhagen K C, et al., *Blood.* 2014; 123 (7):1098101). The NRPs provided an early survival advantage in this model (see FIG. 9A), suggesting, without being bound by any specific theory, that NETs are agents of inflammatory damage in the absence of pathogens and a consequent requirement for their containment and elimination. nNIF also improved mortality in the CLP model of polymicrobial sepsis (see FIGS. 9B and 9C), supporting existing evidence that NETs are effectors of collateral vascular and tissue injury in this experimental syndrome (see Czaikoski P G, et al., *PloS one.* 2016; 11 (2):e0148142). The results in both models suggest that NET generation, like other neutrophil effector functions (see Nathan C., *Nature.* 2002; 420 (6917):846-52), has evolved to contain and eliminate pathogens but can also injure the host if it is activated by pathologic inflammatory signals in the absence of infection or by microbes in an uncontrolled fashion. NRPs may also have potential as anti-inflammatory therapies (see Nathan C., *Nat Rev Immunol.* 2006; 6 (3):173-82) in specific syndromes in which NET formation contributes to acute or progressive pathologic inflammation.

EXAMPLES

To further illustrate these embodiments, the following examples are provided. These examples are not intended to limit the scope of the claimed invention, which should be determined solely on the basis of the attached claims.

Example 1—NET Formation by Human Neonatal Neutrophils can be Regulated by a Peptide in Umbilical Cord Blood In vitro NET deployment by neutrophils from umbilical cord blood on the day of delivery and from peripheral blood of infants collected at later days of life was examined. NET formation was assessed qualitatively using live cell imaging with SYTO® Green (cell permeable) and SYTOX® Orange (cell impermeable) DNA stains and quantitatively by supernatant NET-associated histone H3 measurement (see McInturff A M, et al., *Blood.* 2012; 120 (15):3118-25). PMNs isolated from cord blood (day 0), whether from preterm (N=8) or healthy term infants (N=2), did not form NETs when stimulated (see FIGS. 1A and 1B), consistent with earlier observations (see Yost C C, et al. *Blood.* 2009; 113 (25):6419-27). Nevertheless, term and preterm neonates rapidly developed durable capacity to form NETs (see FIGS. 1A and 1B). NET formation over the first 60 days of extrauterine life was serially assessed for seven premature neonates. Stimulated NET formation was demonstrable by day 3 ex utero for even the most prematurely-born infants (see Table 1 below), and maximal NET forming capacity was achieved between day 3 and day 14 (see FIG. 1A). Impaired perinatal NET formation is a feature of the neonate. PMNs isolated from healthy pregnant women immediately before delivery robustly formed NETs (see FIG. 1C).

TABLE 1

| Clinical Characteristics and Infectious Complications of Preterm Infant Subjects | |
|---|---|
| Gestational ages at birth | 23⁵⁄₇-29²⁄₇ weeks |
| Birth weight | 570-1160 g |
| Female gender | 55% |
| Indication for pre-term delivery | |
| Prolonged premature rupture of membranes or preterm labor | 8 |
| Pregnancy induced hypertension | 1 |
| Placental abruption/preterm labor | 0 |
| Bacterial blood culture results | |
| *E. coli* | 0 |
| Coagulase (−) *Staphylococcus* | 2 |
| Group B *Streptococcus* | 0 |
| Negative | 6 |
| Meningitis | 2 |
| Pneumonia | 2 |
| Antibiotic treatment | All treated, 2-14 days |

Rapid development of NET competency (see FIG. 1A) indicates that a factor in umbilical cord blood modulates NET formation. "Switch" experiments in which PMNs from 60-day-old preterm neonates were pre-incubated with stored, day 0 autologous cord blood plasma or with freshly-collected autologous day 60 venous blood plasma were performed. PMNs from healthy adults were pre-incubated in day 0 cord blood plasma or, in parallel, in autologous adult plasma. Pre-incubation in day 0 cord blood plasma depressed NET formation by day 60 neonatal PMNs and control adult PMNs stimulated with LPS, whereas freshly isolated autologous plasma did not (see FIG. 1D). This result, and the time course of NET competency (see FIG. 1A), is consistent with a cord blood plasma factor that inhibits NET formation and that rapidly decreases in the circulation of the infant after delivery.

FIG. 2A), and it was found that this synthetic nNIF has potent NET-inhibitory activity (see FIG. 2E). A scrambled control peptide (nNIF-SCR; see Table 2 below) does not. These results may demonstrate that nNIF, or a larger protein that encompasses it, is an endogenous inhibitor of NET formation in cord blood plasma from preterm and term neonates (see FIG. 2B). Commercially available, active, full-length A1AT purified from human plasma and recombinant A1AT did not inhibit NET formation (see FIG. 2E), consistent with previous reports (see Farley K, et al., *Journal of immunology.* 2012; 189 (9):4574-81 and Frenzel E, et al., *Int J Biol Sci.* 2012; 8 (7):1023-5), indicating that intact A1AT does not contribute to NET-inhibitory activity.

TABLE 2

Sequences for the NET-Inhibitory Peptides and Their Specific Scrambled Peptide Controls

| | |
|---|---|
| nNIF | KFNKPFVFLMIEQNTKSPLFMGKVVNPTQ (SEQ ID NO: 1) |
| nNIF-SCR | LNTNKTKMGVQFPKMPFFKQIPVNSLEFV (SEQ ID NO: 5) |
| CRISPP | M_IPPEVKFNKPFVFLMIDQNTKVPLFMGK (SEQ ID NO: 2) |
| CRISPP-SCR | V_MDITPMQVGPLKMKPKVIFNPFKLFENF (SEQ ID NO: 6) |
| A1ATm$^{358}$ | MFLEAIPMSIPPEVKFNKPFVFLMIEQNTKSPLFMLKVVS (SEQ ID NO: 3) |
| A1ATm$^{358}$-SCR | PMVSVAMMLSENIFKLPEVKSVPTEFFPKFINMKLLPFQI (SEQ ID NO: 7) |

Experiments involving heat denaturation, proteinase K treatment, and lipid extraction of cord blood plasma to identify the NET-Inhibitory Factor indicated that it is a protein. The proteomes of day 0 cord blood plasma and day 28 venous blood plasma from a preterm infant whose NET-forming capacity was determined in experiments summarized in FIG. 1A were examined. Two-dimensional gel electrophoresis demonstrated protein and peptide clusters with differential representations in cord blood and day 28 plasma samples. Trypsin digest and tandem mass spectroscopic analysis of proteins from one of the clusters, using the NCBI human trypsin-specific database, yielded partial or complete sequences including a peptide in cord blood plasma with a predicted molecular mass of ≈4 kDa. Its sequence is identical to the sequence in the carboxy terminus of alpha-1-antitrypsin (A1AT) (see FIG. 2A), a known 52 kDa plasma protease inhibitor with anti-inflammatory and immunomodulatory properties (see Janciauskiene S M, et al., *Respir Med.* 2011; 105 (8):1129-39 and Jonigk D, et al., *Proc Natl Acad Sci USA.* 2013; 110 (37):15007-12). Using western blotting with a polyclonal antibody raised against the carboxy terminal 18 amino acids of A1AT, a ≈4-6 kDa peptide was found in term infant cord blood plasma in much greater abundance than in venous plasma from healthy adults (see FIG. 2B, left panel), and that was provisionally termed neonatal NET-Inhibitory Factor (nNIF). Cord blood plasma was then immunodepleted using the anti-A1AT carboxy terminus antibody immobilized on affinity resin beads. Depleted plasma and peptides eluted from the affinity beads were examined for NET-inhibitory activity. Unaltered cord blood plasma inhibited NET formation by LPS-stimulated adult PMNs, as in previous experiments (see FIG. 1C), as did peptides eluted from the immunoaffinity beads, whereas immunodepleted plasma did not (see FIG. 2C). A 4-6 kDa candidate nNIF peptide was found in much higher quantity in the affinity purification eluate compared to the depleted plasma (see FIG. 2D). In parallel, the 29 amino acid peptide detected in cord blood plasma was synthesized (see With an assay utilizing quantitative western blotting with the anti-A1AT carboxy terminus antibody and a standard curve constructed with different concentrations of synthetic nNIF, nNIF was detected in preterm cord blood plasma samples, whereas it was undetectable, or detectable in only trace levels, in plasma from healthy adults (see FIG. 2B, right panel). Using the same assay, a peptide of appropriate molecular mass was not detected in plasma samples from adult subjects (N=10) with chronic inflammatory syndromes (granulomatosis with polyangiitis, giant cell arteritis, or rheumatoid arthritis) that might conceivably induce NET regulatory factors. Thus, nNIF may be restricted to placental blood and blood of neonates in the first few days of life.

Figure 4B:
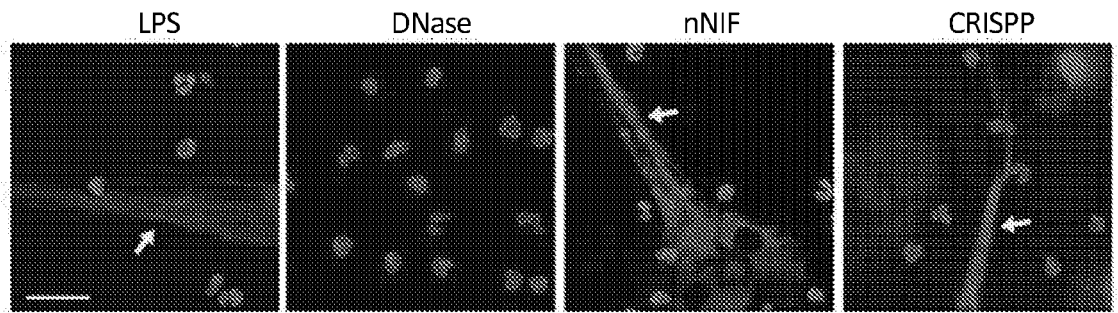
FIG. 4B is a series of images depicting isolated adult neutrophils that were stimulated with LPS (100 ng/mL, 1 hour), DNase (3.78 U/mL), nNIF (1 nM), or CRISPP (1 nM), and NETs were imaged as in FIG. 4A after an additional 1 hour incubation (60× magnification, scale bar=20 µm). In a second experiment NETs were also intact after treatment with nNIF or CRISPP but dismantled by DNase.
Figure 5A:
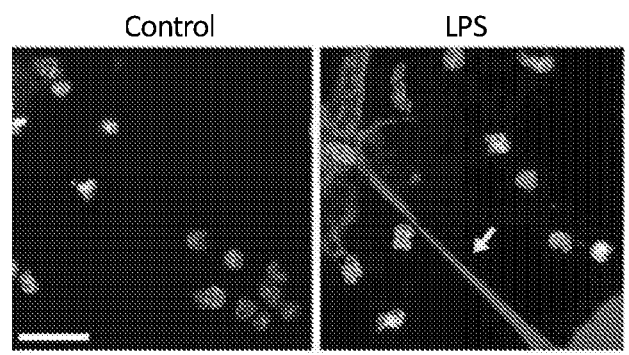
FIG. 5A is two images depicting isolated adult neutrophils that were preincubated in medium (1 hour) and then incubated alone (Control) or with LPS (100 ng/mL, 1 hour) followed by live cell imaging as in FIG. 1A (60× magnification, scale bar=20 µM).
Figure 5B:
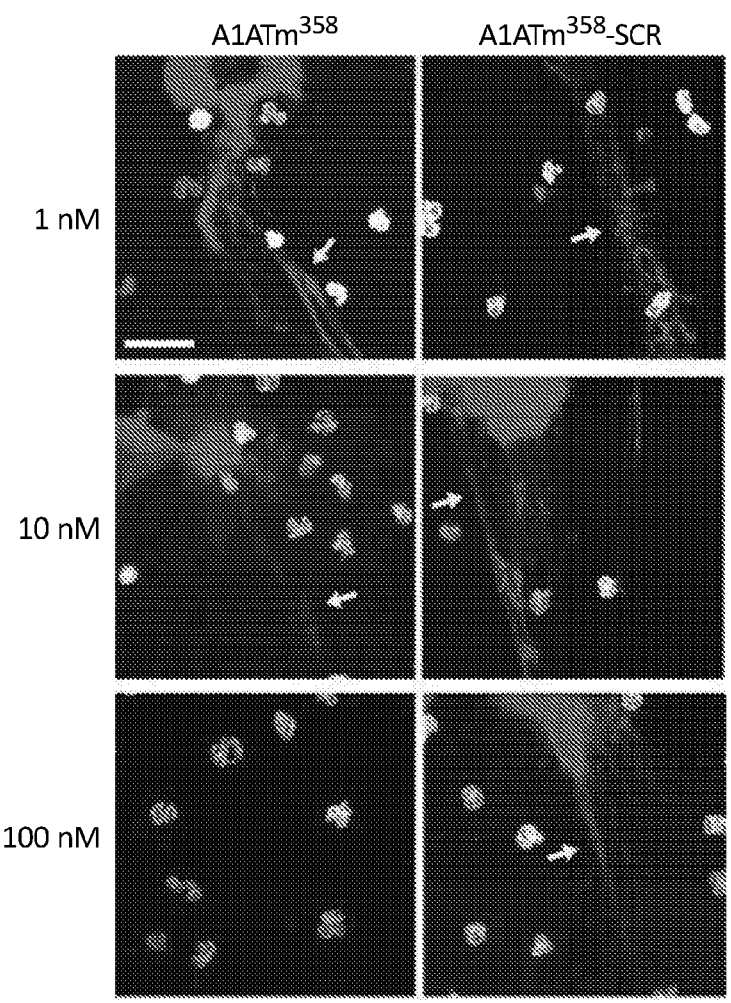
FIG. 5B is a series of images depicting, in parallel, neutrophils that were preincubated with synthesized A1ATm$^{358}$ or scrambled A1ATm$^{358}$ (A1ATm$^{358}$-SCR) (1, 10, or 100 nM, 1 hour), activated with LPS, and NETs that were assessed by live cell imaging after incubation for 1 hour. A second experiment yielded a similar concentration-dependent pattern of inhibition by A1ATm$^{358}$ but not A1ATm$^{358}$-SCR.

Example 2—nNIF and nNIF-Related Peptides (NRPs) Are a Family of Previously Unrecognized PMN Modulators Additional NET inhibitory peptides were identified based on sequence analysis of nNIF. nNIF has substantial similarity to Cancer-Associated SCM-Recognition, Immunedefense Suppression, and Serine Protease Protection Peptide (CRISPP) (see FIG. 2A), a consensus peptide based on factors present in the blood of patients with cancer (see Cercek L, et al., *Cancer Detect Prev.* 1992; 16 (5-6): 305-19; Cercek L, et al., *Cancer Detect Prev.* 1993; 17 (3):433-45; and Cercek L, et al. *Cancer Detect Prev.* 1993; 17 (3):447-54). CRISPP and a scrambled control peptide (CRISPP-SCR) were synthesized, and it was found that CRISPP inhibits NET formation triggered by LPS, as does nNIF, whereas CRISPP-SCR does not (see FIG. 3A). nNIF and CRISPP inhibited NET formation by neutrophils isolated by Ficoll-Paque and differential centrifugation in addition to PMNs isolated by positive immunoselection. Post-treatment protocols demonstrated that nNIF and CRISPP do not degrade or dismantle previously-formed NETs (see FIGS. 4A and 4B). Thus, they differ from DNases, which have been shown to disrupt NETs after they are formed (see Brinkmann V, et al., *J Cell Biol.* 2012; 198 (5):773-83; Yipp B G, et al., *Blood.* 2013; 122 (16):2784-94; Kolaczkowska E, et al., *Nature communications.* 2015; 6 (6673); Caudrillier A, et al., *J Clin Invest.* 2012; 122 (7):2661-71; and Saffarzadeh M, et al., *Curr Opin Hematol.* 2013; 20 (1):3-9). A previously-described 44 amino acid carboxy terminus cleavage fragment of A1AT, A1ATm$^{358}$, which is bound to matrix in the human placenta and overlaps in sequence with nNIF, was also examined (see Niemann M A, et al., Matrix. 1992; 12 (3):233-41 and Niemann M A, et al., *Journal of* cellular biochemistry. 1997; 66 (3):346-57) (see Table 2 above). A1ATm$^{358}$ was synthesized, and it was found that it inhibits NET formation, although with lesser potency than nNIF (see FIGS. 5A and 5B).

Without being bound by any specific theory, these observations indicate that nNIF, CRISPP, and A1ATm$^{358}$ represent a previously-unrecognized family of nNIF-Related Peptides (NRPs) that modulate NET formation (see FIGS. 1A-5B). The presence of NRPs in umbilical blood (nNIF), placenta (A1ATm$^{358}$), and, in some cases, adult plasma (CRISPP-related peptides) suggests that NET-Inhibitory Factors may be broadly distributed and that other NRPs may be identified.

Figure 11:
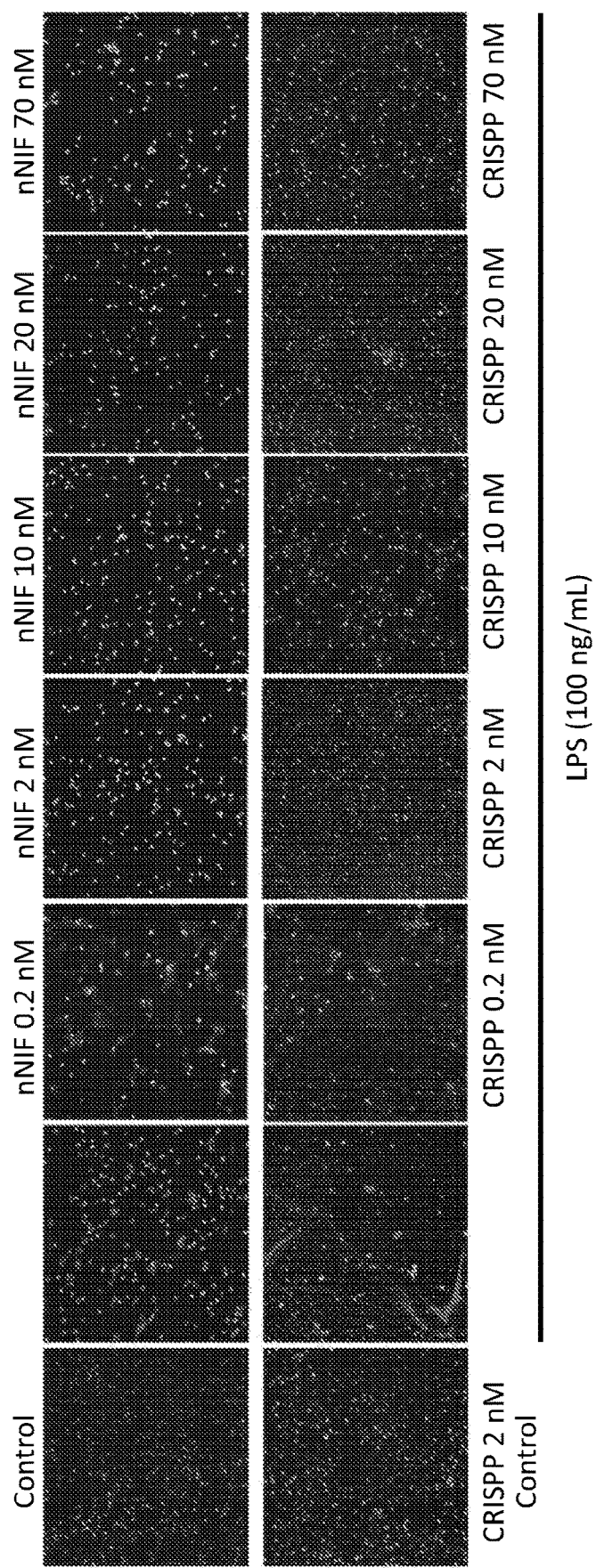
FIG. 11 is a series of images depicting that nNIF and CRISPP inhibit NET formation at nanomolar concentrations. PMNs from healthy adult volunteers were preincubated in medium alone or with nNIF or CRISPP in the indicated concentrations for 1 hour. LPS (100 ng/mL) was then added, and the leukocytes were incubated for 1 hour followed by live cell imaging as in FIG. 1A (red fluorescence=NETs; green fluorescence=nuclear DNA; 20× magnification). This concentration-dependent inhibition of NET formation by nNIF and CRISPP was seen in three experiments with neutrophils from different donors.

Example 3—CRISPP and nNIF Inhibit NET Formation Induced by a Spectrum of NET-Triggering Agonists The inhibitory activity of NRPs when NET formation is induced by diverse agonists, focusing on nNIF and CRISPP, was examined. Both inhibited LPS-stimulated NET deployment in multiple experiments (see FIGS. 2E, 3A, and 11). Phorbol Myristate Acetate (PMA) is commonly employed as a potent non-physiologic agonist to induce NET formation in vitro (see Sorensen O E, et al., *Journal of clinical investigation.* 2016; 126 (5):1612-20; Papayannopoulos V, et al., *J Cell Biol.* 2010; 191 (3):677-91; Farley K, et al., *Journal of immunology.* 2012; 189 (9):4574-81; and Fuchs T A, et al., *J Cell Biol.* 2007; 176 (2):231-41). nNIF and CRISPP, but not CRISPP-SCR, blocked PMA-stimulated NET deployment (see FIG. 3B). CRISPP also inhibited NET formation induced by live *Staphylococcus aureus* (see Brinkmann V, et al., *J Cell Biol.* 2012; 198 (5):773-83; Kolaczkowska E, et al. *Nature communications.* 2015; 6 (6673); Yost C C, et al. *Blood.* 2009; 113 (25):6419-27; and Fuchs T A, et al., *J Cell Biol.* 2007; 176 (2):231-41) (see FIG. 3C). This result may suggest that NRPs inhibit "vital" NETosis in addition to "suicidal" NETosis as is triggered by PMA (see Yipp B G, et al., *Blood.* 2013; 122 (16):2784-94 and Fuchs T A, et al. *J Cell Biol.* 2007; 176 (2):231-41), since *S. aureus* has been reported to release NETs by chromatin decondensation and vesicular export without neutrophil lysis (see Yipp B G, et al., *Blood.* 2013; 122 (16):2784-94; Yipp B G, et al., *Nature medicine.* 2012; 18 (9):1386-93; and Pilsczek F H, et al., *Journal of immunology.* 2010; 185 (12):7413-25). The ability of NRPs to inhibit NETosis induced by other pathogens was also examined, and it was found that CRISPP inhibited NET generation stimulated by dengue virus (see FIG. 3D). Several viruses trigger NET deployment (see Saitoh T, et al. *Cell host & microbe.* 2012; 12 (1):109-16; Jenne C N, et al. *Cell host & microbe.* 2013; 13 (2):169-80; and Raftery M J, et al. *J Exp Med.* 2014; 211 (7):1485-9743-45), but dengue, which interacts with ligands on myeloid cells (see Cheung R, et al. *J Clin Invest.* 2011; 121 (11):4446-61), has not previously been reported to have this activity. To further explore the inhibitory activities of nNIF and NRPs, heme was examined. Heme is an endogenous damage-associated molecular pattern (DAMP) and toxin (see Gladwin M T, et al., *Blood.* 2014; 123 (24):3689-90) that has been shown to induce NETs in a murine model of sickle cell vasculopathy (see Chen G, et al., *Blood.* 2014; 123 (24):3818-27). It was found that heme triggers NET formation by human PMNs and that nNIF and CRISPP inhibit this response (see FIG. 3E). Thus, NRPs inhibit NET deployment induced by microbes and microbial toxins, host-derived DAMPs, and pharmacologic agonists.

Example 4—NRPs Selectively Inhibit NET Formation without Interrupting Other Key Neutrophil Anti-Microbial Functions or Platelet Responses Total, phagocytic, and NET-mediated PMN killing of a pathogenic strain of *Escherichia coli* (*E. coli*) was examined using bacterial killing assays, and it was found that CRISPP depressed extracellular NET-mediated and total bacterial killing, but that phagocytic intracellular killing was not altered (see FIG. 6A). In additional incubations employing nNIF or CRISPP, the NRPs did not inhibit generation of reactive oxygen species (ROS), phagocytosis, or interleukin 8 (IL-8) induced chemotaxis in Boyden chambers (see FIGS. 6B-6D). Although each peptide was not tested in all assays, these experiments indicate that the NRPs selectively inhibit NET formation while leaving other key anti-microbial activities of PMNs intact. In addition, it was found using flow cytometry that CRISPP does not inhibit surface translocation of P-selectin by thrombin-stimulated platelets, or formation of heterotypic aggregates by activated human platelets and PMNs (see FIGS. 6E and 6F). These and other functions of activated platelets have been reported to play a role in anti-microbial defense (see Vieira-de-Abreu A, et al., *Semin Immunopathol.* 2012; 34 (1):5-30). In addition, interaction of activated platelets with neutrophils induces NET formation (see Clark S R, Ma A C, et al., Platelet TLR4 activates neutrophil extracellular traps to ensnare bacteria in septic blood. *Nature medicine.* 2007; 13 (4):463-9; and Caudrillier A, et al., *J Clin Invest.* 2012; 122 (7):2661-71). FIGS. 6E and 6F indicate that PMNs, but not platelets, are cellular targets for NRPs and that platelet inflammatory activities are not disrupted by NRPs.

Example 5—nNIF and CRISPP Inhibit Nuclear Chromatin Decondensation and Histone Citrullination in Activated Neutrophils nNIF and CRISPP were used as probes to dissect mechanisms of action for NRPs. Generation of ROS is thought to be essential in many, but not all, pathways that mediate NET formation (see Brinkmann V, et al., *J Cell Biol.* 2012; 198 (5):773-83; Yipp B G, et al., *Blood.* 2013; 122 (16):2784-94; Papayannopoulos V, et al., *J Cell Biol.* 2010; 191 (3):677-91; Lood C, et al., *Nature medicine.* 2016; 22 (2):146-53; Yost C C, et al., *Blood.* 2009; 113 (25):6419-27; Farley K, et al., *Journal of immunology.* 2012; 189 (9):4574-81; and Branzk N, et al., Semin Immunopathol. 2013; 35 (4):513-30), but was not inhibited by CRISPP (see FIG. 6B). Consistent with this result, previous observations have indicated that ROS supplementation is not sufficient to restore NET competency to neonatal PMNs (see Yost C C, et al., *Blood.* 2009; 113 (25):6419-27), suggesting, but without being bound by any specific theory, that nNIF also acts at a regulatory step or steps different from those influenced by ROS. Decondensation of nuclear chromatin has been reported as a pivotal event that is required for NET formation (see Sorensen O E, et al., *Journal of clinical investigation*. 2016; 126 (5):1612-20; Brinkmann V, et al., *J Cell Biol*. 2012; 198 (5):773-83; Yipp B G, et al., *Blood*. 2013; 122 (16):2784-94; Yipp B G, et al., *Nature medicine*. 2012; 18 (9):1386-93; Papayannopoulos V, et al., *J Cell Biol*. 2010; 191 (3):677-91; Farley K, et al., *Journal of immunology*. 2012; 189 (9):4574-81; Fuchs T A, et al., *J Cell Biol*. 2007; 176 (2):231-41; and Branzk N, et al., 2013; 35 (4):513-30. It was found that PMA induces decondensation and loss of lobulation of PMN nuclei (see FIG. 7A), as previously reported (see Papayannopoulos V, et al., *J Cell Biol*. 2010; 191 (3):677-91). The number of decondensed nuclei was dramatically reduced by nNIF and CRISPP, but not by nNIF-SCR or CRISPP-SCR (see FIG. 7A). Neutrophil chromatin decondensation is mediated by PAD4, which weakens histone-DNA binding by catalyzing conversion of histone arginines to citrullines (see Sorensen O E, et al., *Journal of clinical investigation*. 2016; 126 (5):1612-20; Wang Y, et al., *J Cell Biol*. 2009; 184 (2):205-13; and Li P, et al., *J Exp Med*. 2010; 207 (9):1853-62). Consistent with this, an irreversible inhibitor of PAD4, Cl-amidine (see Li P, et al., *J Exp Med*. 2010; 207 (9):1853-62), blocked nuclear decondensation under the conditions of the experiments disclosed herein (see FIG. 7A, lower panels). A cell-free PAD4 assay was then employed, and it was found that nNIF blocked its activity, as did Cl-amidine used as a control (see FIG. 7C). In an initial comparison of NRPs, the order of potency of inhibition of PAD4 was nNIF ≈CRISPP>A1ATm$^{358}$, which is the same as their relative inhibition of NETosis. In parallel, nuclear histone H3 citrullination was examined in activated neutrophils (see Sorensen O E, et al., 2016; 126 (5):1612-20 and Li P, et al., *J Exp Med*. 2010; 207 (9):1853-62), and rapid citrullination was detected within 15 minutes of activation with PMA. This was inhibited by nNIF and by Cl-amidine (see FIG. 7D), suggesting that NRPs act at this step to block nuclear decondensation (see FIG. 7A).

Neutrophil elastase (NE) is also implicated in nuclear decondensation and NET formation (see Sorensen O E, et al., 2016; 126 (5):1612-20; Brinkmann V, et al., *J Cell Biol*. 2012; 198 (5):773-83; Papayannopoulos V, et al., *J Cell Biol*. 2010; 191 (3):677-91; Kolaczkowska E, et al., *Nature communications*. 2015; 6 (6673); and Branzk N, et al., Semin Immunopathol. 2013; 35 (4):513-30). An NE inhibitor, sivelestat, blocks nuclear decondensation in vitro (see FIGS. 12A and 12B). CRISPP and CRISPP-SCR were synthesized with FLAG tags added to the carboxy terminus of each peptide (CRISPP-F, CRISPP-SCR-F), and it was found that both are internalized by activated neutrophils (see FIG. 7E), that CRISPP-F inhibits NET formation (see FIG. 13), and, in a protein proximity assay, that CRISPP-F is initially localized within 40 nm of NE. This suggested that NRPs may block actions of NE in NETosis. In in vitro assays, however, neither nNIF nor CRISPP inhibited NE activity (see FIGS. 12A and 12B).

NRPs inhibit NET formation in vivo and alter outcomes in systemic inflammation. To determine if nNIF and NRPs inhibit NET formation in vivo, a new model of in vivo NETosis was established using intraperitoneal (i.p.) infection of C57BL/6 mice with a clinical isolate of *E. coli*. Three hours after inoculation, live cell imaging of peritoneal fluid samples demonstrated robust NET formation. In addition, deposition of NETs was observed on the serosal surface of the peritoneal membranes. nNIF and CRISPP, but not CRISPP-SCR, inhibited NET formation by peritoneal fluid PMNs (see FIG. 8A) and deployment of NETs on the peritoneal surface (see FIG. 8B). Active peritonitis was demonstrated with increased neutrophil numbers and bacterial counts (see FIGS. 8C and 8D). The number of PMNs was greater in samples from CRISPP-treated animals, and the trend was to greater numbers in nNIF-treated mice (see FIG. 8C), potentially due to inhibition of lytic NETosis (see Brinkmann V, et al., *J Cell Biol*. 2012; 198 (5):773-83 and Yipp B G, et al., *Blood*. 2013; 122 (16):2784-94). The number of *E. coli* colony forming units was also greater in samples from NRP-treated animals than in those treated with the CRISPP-SCR control (see FIG. 8D), suggesting decreased NET-mediated bacterial killing. nNIF and CRISPP also inhibited peritoneal NET formation in Swiss Webster mice infected with *E. coli* (see FIGS. 8E and 8F), suggesting that this result may be generalizable across mouse backgrounds.

Figure 9A:
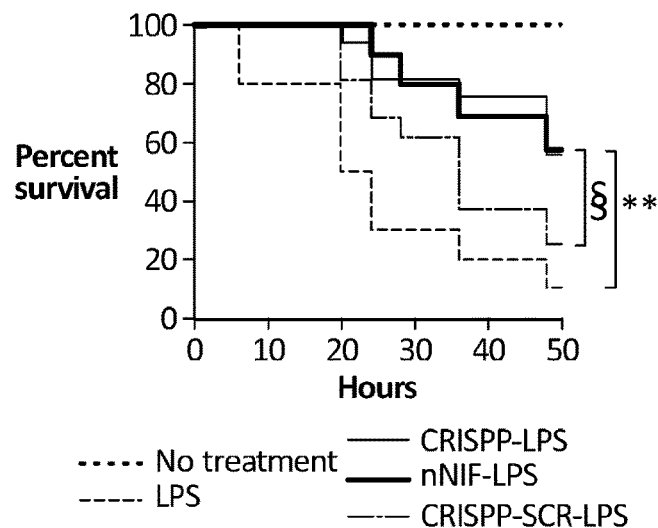
FIG. 9A is a graph depicting C57BL/6 mice that were challenged with LPS (25 mg/kg i.p.). CRISPP, nNIF, or CRISPP-SCR (10 mg/kg i.p.) was given 1 hour before and 6 hours after LPS. Animals with no treatments or given LPS alone were studied in parallel (n≥10 mice for each condition). **P<0.01, log-rank (Mantel-Cox) statistical tool used. The survival difference between nNIF-LPS and CRISPP-LPS compared to CRISPP-SCR-LPS trended toward significance (§ P=0.051).
Figure 9B:
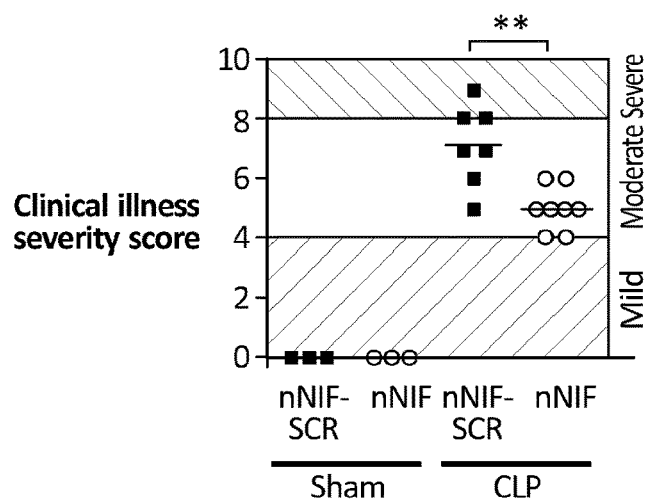
FIG. 9B is a graph depicting C57BL/6 mice that were subjected to cecal ligation and puncture (CLP). nNIF or nNIF-SCR (10 mg/kg i.p.) was given 1 hour before and 6 hours after surgery (n≥7 in each group). Mice subjected to sham surgery were studied in parallel (n=3 in each group). Clinical illness severity scores (see Araujo C V, et al., *Shock.* 2016; 45 (4):393-403) were determined at 24 hours. One way ANOVA with Neuman-Keul's post hoc testing; ** P<0.01 for nNIF versus nNIF-SCR groups.
Figure 9C:
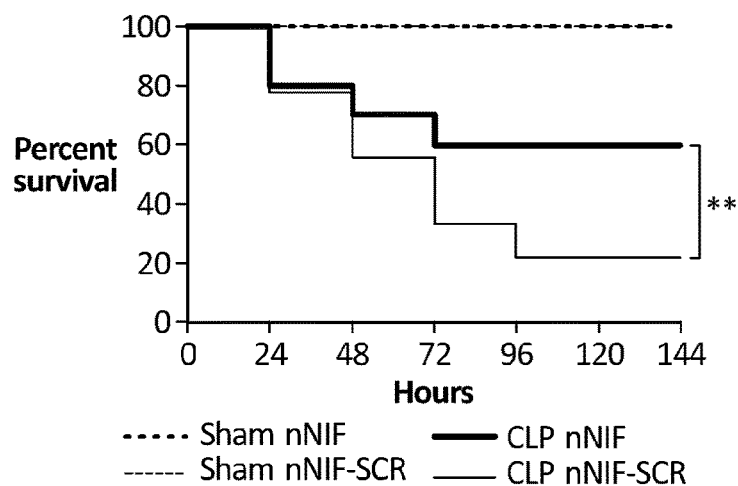
FIG. 9C is a graph depicting mice that were assessed for severity of systemic illness in FIG. 9B and were then followed daily, where survivors were sacrificed at 144 hours. Log-rank (Mantel-Cox) statistical tool used. **P<0.01.
Figure 10:
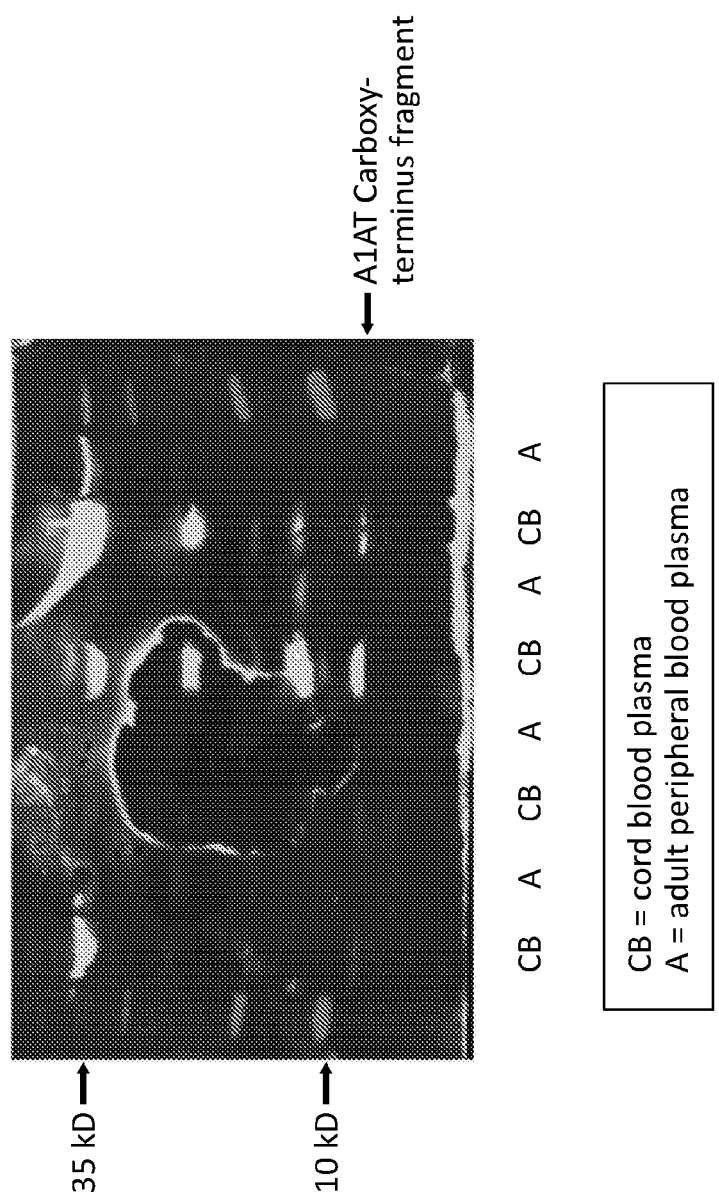
FIG. 10 is an image depicting that a low molecular weight peptide recognized by an antibody against the carboxy-terminus of A1AT is detected in umbilical cord blood samples but not plasma from adults. Samples of cord blood plasma from four healthy term neonates and venous blood samples from four healthy adult volunteers were examined by western blotting. As stated above, this is the full gel from which the left panel of FIG. 2B was prepared.

In a second model, it was found that i.p. LPS triggers peritoneal NET formation in C57BL/6 mice, although not as robustly as do live *E. coli*, and that LPS-induced peritoneal NET formation was inhibited by nNIF and CRISPP but not CRISPP-SCR. Intravascular NETs have been observed in mice challenged with i.p. LPS (see McDonald B, et al., *Cell host & microbe*. 2012; 12 (3):32433 and Tanaka K, et al., *PloS one*. 2014; 9 (11):e111888) and cause tissue damage and contribute to mortality when they are induced by intravenous LPS, bacteria, or other agonists (see Kolaczkowska E, et al., *Nature communications*. 2015; 6 (6673); Xu J, et al., *Nature medicine*. 2009; 15 (11):1318-21; McDonald B, et al., *Cell host & microbe*. 2012; 12 (3): 32433; Caudrillier A, et al., *J Clin Invest*. 2012; 122 (7): 2661-71; and Chen G, et al., *Blood*. 2014; 123 (24):3818-27). Therefore, mortality was examined in mice given i.p. LPS, and it was found that all animals treated with CRISPP (n=6), but only 30% of those treated with CRISPP-SCR (n=6), were alive when the experiment was terminated at 50 hours (P<0.02). In a second experiment, in which nNIF was also examined, and which was extended to 72 hours, there was reduced mortality in the NRP-treated groups challenged with LPS compared to mice treated with CRISPP-SCR or LPS alone (n=10 for each group) at 50 hours. FIG. 9A illustrates combined data from the two experiments. At 72 hours in the second experiment, the survival advantage provided by nNIF was durable (P=0.007 compared to LPS alone), whereas that of CRISPP was not. This may be due to differences in pharmacokinetics or half-lives of nNIF and CRISPP under these conditions.

Similar experiments were also performed using the cecal ligation and puncture (CLP) model of polymicrobial sepsis (see Hubbard W J, et al., *Shock*. 2005; 24 Suppl 1 (52-7); Araujo C V, et al., *Shock*. 2016; 45 (4):393-403; and Czaikoski P G, et al., *PloS one*. 2016; 11 (2):e0148142). Mice treated with nNIF had lower clinical illness scores (see Araujo C V, et al., *Shock*. 2016; 45 (4):393-403) at 24 hours and significantly increased survival at 144 hours after CLP compared to nNIF-SCR-treated animals (see FIGS. 9B and 9C). Together, these experiments (see FIGS. 8A-9C) demonstrate that nNIF and CRISPP inhibit NET formation in vivo, and provide initial evidence that they have beneficial effects in models of systemic sterile inflammation and infection in which NET formation may influence tissue injury and mortality (see Kolaczkowska E, et al., *Nature communications*. 2015; 6 (6673); Clark S R, et al., *Nature medicine*. 2007; 13 (4):463-9; McDonald B, et al., *Cell host & microbe*. 2012; 12 (3):32433; and Czaikoski P G, et al., *PloS one*. 2016; 11 (2):e0148142).

Example 6—an A1AT Cleavage Fragment Generated by HTRA1 (HTRA1-CF) Inhibits NET Formation Progressive proteolytic cleavage of A1AT in the placenta may occur, and cleavage of A1AT by human stromelysin-3, yielding A1ATm[358], has been reported (see Pei D, et al., *J Biol Chem.* 1994; 269 (41):25849-55). In addition, other proteases can fragment A1AT. Accordingly, one or more placental proteases may cleave A1AT to yield nNIF. This could occur in extravascular placental compartments or in cord blood, depending on the protease(s) and local availability of substrate. A protease, high temperature requirement A1 (HTRA1) is upregulated in the human placenta in the third trimester of pregnancy, and HTRA1 cleaves A1AT in the C-terminus, generating a fragment somewhat larger in size but including the sequence of nNIF (see Frochaux V et al., *Plos One.* 9(10): e109483. doi:10.1371).

Figure 14:
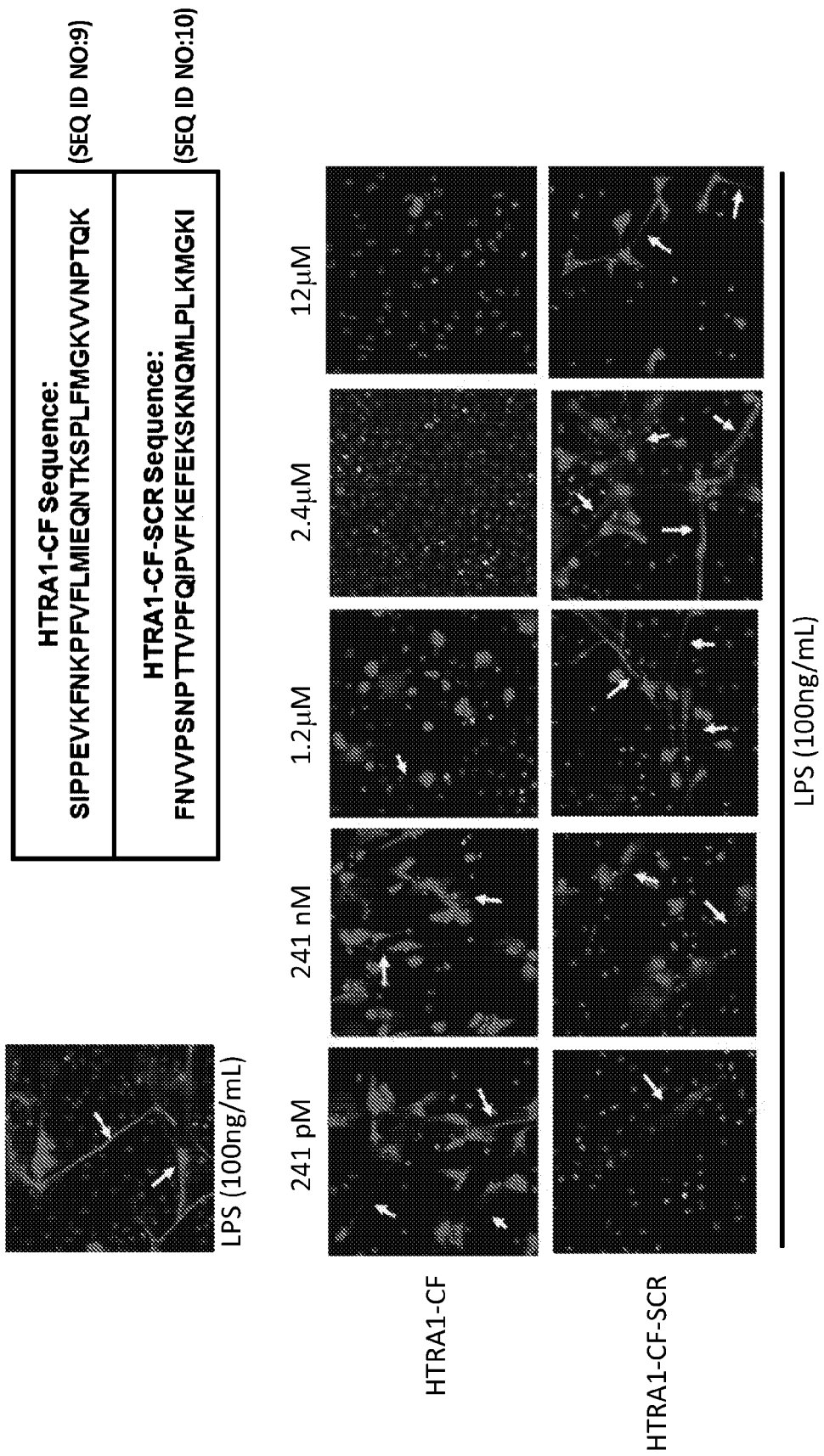
FIG. 14 depicts that a protease, high temperature requirement A1 (HTRA1), is upregulated in the human placenta in the third trimester of pregnancy and cleaves A1AT in the C-terminus, generating a fragment somewhat larger in size but including the sequence of nNIF (see Frochaux V, et al., *Plos one.* 9(10): e109483. doi:10.1371). The peptide generated by cleavage of A1AT by HTRA1 was synthesized and it was found that the peptide inhibits NET formation.

The peptide generated by cleavage of A1AT by HTRA1 (HTRA1-CF) was synthesized, and it was found that HTRA1-CF inhibits NET formation (see FIG. 14). Without being bound by any specific theory, as one or more placental proteases can enzymatically cleave A1AT, such cleavage may be a mechanism for production of nNIF.

Example 7—Animal Studies

All mouse studies were approved by the University of Utah's Institutional Animal Care and Review Board. Swiss Webster and C57BL/6 male mice between the ages of 8 and 12 weeks were purchased from CHARLES RIVERS LABORATORIES™ or JACKSON LABORATORIES™ for all experiments. Mice were housed in specific pathogen-free microisolator cages that were located in a room maintaining a constant temperature and on a 12-hour light-dark cycle. All treatment groups were weight matched and randomized to treatment at the initiation of an experiment. The researchers conducting the experiments were blinded to the experimental groups during testing. No inclusion or exclusion criteria were used in designing the experiments.

Example 8—Reagents

Lipopolysaccharide (*E. coli* serotype 0111:134 and *Salmonella enteritidis*), poly-L-lysine, cytochalasin B, cytochalasin D, paraformaldehyde (p-FA), sivelestat, NE, the NE substrate (MeOSuc)-AAPV-(pNA), and thrombin were purchased from SIGMA-ALDRICH®. Additional reagents were: TO-PRO®-3 stain, phalloidin, SYTO® Green (cell permeable DNA stain), and SYTOX® Orange (cell impermeable DNA stain) (MOLECULAR PROBES®); Cl-amidine (CALBIOCHEM®); DNase (PROMEGA™); Anti-CD15-microbeads (MILTENYI™); Medium-199 (LONZA™) and micrococcal DNase (WORTHINGTON®).

Example 9—nNIF and NRP Synthesis nNIF, NRPs, and their specific scrambled peptide controls (see Table 2 above) were synthesized by the DNA/Peptide Facility, a unit of the Health Sciences Center Cores at the University of Utah. The core facility also verified the sequence and purity of the provided peptides.

Example 10—PMN and Platelet Isolation

PMNs were isolated from ACD or EDTA anticoagulated venous blood from healthy adults, healthy term infants, and prematurely born infants (see Yost C C, et al., *Blood.* 2009; 113 (25):6419-27 and McInturff A M, et al., *Blood.* 2012; 120 (15):3118-25) under protocols approved by the University of Utah Institutional Review Board. For the eight prematurely born infants from whom cord and peripheral blood samples were collected, cord and peripheral blood plasma and PMN preparations were obtained at five separate time points throughout the first two months of life. PMN suspensions (>96% pure) were prepared by positive immunoselection using anti-CD15-coated microbeads and an AUTO-MACS® cell sorter (MILTENYI™), and were resuspended at $2\times10^6$ cells/mL concentration in serum-free M-199 media at 370° C. in 5% $CO_2$/95% air. Human platelets were isolated as described (see Weyrich A S, et al., *J Clin Invest.* 1996; 97 (6):1525-34).

Example 11—Live Cell Imaging of NET Formation

Qualitative assessment of NET formation was performed as previously reported (see Yost C C, et al., *Blood.* 2009; 113 (25):6419-27 and McInturff A M, et al., *Blood.* 2012; 120 (15):3118-25). Briefly, primary PMNs isolated from preterm infants, healthy term infants, and healthy adults ($2\times10^6$ cells/mL) were incubated with control buffer or stimulated with indicated agonists or bacteria for 1 hour at 37° C. in 5% $CO_2$/95% air on glass coverslips coated with poly-L-lysine. For selected experiments, primary PMNs were pre-incubated with autologous plasma, cord blood plasma, nNIF (0.2-70 nM), CRISPP (0.2-70 nM), nNIF-SCR (1 nM), or CRISPP-SCR (1 nM) for one hour prior to stimulation. After pre-incubation and/or stimulation, PMNs were gently washed with PBS and incubated with a mixture of cell permeable (SYTO® Green, MOLECULAR PROBES®) and impermeable (SYTOX® Orange, MOLECULAR PROBES®) DNA fluorescent dyes. Confocal microscopy was accomplished using a FV1000 IX81 confocal microscope and FLUOVIEW™ software (OLYMPUS™). Both 20× and 60× objectives were used. Z-series images were obtained at a step size of 1 µm over a range of 20 µm for each field. FLUOVIEW™ and ADOBE™ PHOTOSHOP™ CS2 software was used for image processing.

Example 12—Imaging of Dengue Virus-Induced NET Formation

Using BSL 2 safety protocols, primary PMNs isolated from healthy adults ($2\times10^6$ cells/mL) were incubated with mock infection buffer or live dengue virus (M010.05) as for live cell imaging. After a 1-hour incubation, the infected PMNs were fixed with 2% p-FA for 10 minutes prior to incubation with fluorescently-labeled, cell-permeable and cell-impermeable DNA dyes, and imaged as for live cell imaging using confocal microscopy.

Example 13—Quantitation of NET Formation: NET-Associated Histone H3 Content

NET-associated histone H3 content was determined as previously described (see McInturff A M, et al., *Blood.* 2012; 120 (15):3118-25). After live cell imaging of control and stimulated primary PMNs ($2\times10^6$/mL; various agonists), the cells were incubated with PBS containing DNase (40 U/mL) for 15 minutes at room temperature to break down and release NETs formed in response to stimulation. The supernatant was gently removed and centrifuged at 420×g for 5 minutes. The cell-free supernatant was then mixed 3:1 with 4× Laemmli buffer prior to western blotting. A polyclonal primary antibody against human histone H3 protein (CELL SIGNALING®) and infrared-conjugated secondary antibodies (LI-COR®) were used. Imaging and densitometry were performed on the ODYSSEY® infrared imaging system)(LI-COR®). This assay was previously validated as a surrogate for NET formation under in vitro conditions (see McInturff A M, et al., *Blood.* 2012; 120 (15):3118-25) as employed in the present studies.

Example 14—Isolation and Identification of nNIF in Umbilical Cord Blood Plasma Two plasma samples from a single preterm infant, one from the umbilical cord blood and one from a peripheral blood sample taken on ex utero day 28, were subjected to abundant plasma protein removal (NORGEN™) prior to 2D-electrophoresis, using separation first by isoelectric focusing (pH range 3-8) and then by size (TGX™ precast gel, BIO-RAD™). The resulting gels were compared for differential protein content. Six differentially expressed protein clusters ("spots") were sent to the University of Utah Proteomics Core for analysis. Following trypsin digestion and tandem mass spectroscopy using an LTQ-FT ion-trap/FTMS hybrid mass spectrometer (THERMO ELECTRON™), candidate proteins/peptides were identified as potential NET-Inhibitory Factors.

Example 15—Affinity Removal of nNIF

Plasma samples were subjected to abundant plasma protein removal (NORGEN™). A polyclonal antibody raised against the carboxy terminal 18 amino acids of A1AT (LIFESPAN BIOSCIENCES™) coupled to resin beads from an immunoprecipitation kit purchased from THERMO SCIENTIFIC™ was then used to immunodeplete the samples. Non-immune IgG coupled to resin beads was used in parallel as a control. Plasma was diluted in lysis buffer from the kit and incubated with the anti-A1AT C-terminus antibody coupled beads or with control beads overnight at 4° C. The beads were then separated by centrifugation, and the immunodepleted and control plasma samples were collected. The A1AT C-terminus antibody coupled and control beads were resuspended in kit-included elution buffer for 10 minutes at room temperature, followed by centrifugation and collection of the eluate and control supernatants. The eluate was analyzed by western blotting (16.5% Tris-tricine gel, BIO-RAD™) using the A1AT C-terminus antibody and by tandem mass spectroscopy. Immunodepleted plasma and eluate samples were examined in assays of NET formation. Active full-length native and recombinant A1AT (both from SIGMA-ALDRICH®) were suspended in elution buffer and tested in parallel.

Example 16—Bacterial Killing Assay

NET-mediated and phagocytic bacterial killing by primary human PMNs was determined as previously described (see Yost C C, et al., *Blood.* 2009; 113 (25):6419-27).

Example 17—Chemotaxis Assay

Chemotaxis by PMNs isolated from healthy adult donors was assessed using a modified Boyden chamber assay ± a 1 hour pre-incubation with nNIF (1 nM), CRISPP (1 nM), or CRISPP-SCR (1 nM). Recombinant human IL-8 (2 ng/mL) was used as the chemoattractant. Chemotaxis through a 5 micron filter was determined by counting PMNs in 10 randomly selected high-power fields as previously described (see Hill H R, et al., *Lancet.* 1974; 2 (7881):617-9). In separate experiments, nNIF, CRISPP, or CRISPP-SCR (all at 1 nM) were evaluated for chemoattractant activity using the same system.

Example 18—Phagocytosis Assay

PMNs were isolated from blood of healthy adult donors and resuspended in M-199 at a concentration of $2\times10^6$ cells/mL. Leukocytes were pre-incubated for 60 minutes under standard conditions with cytochalasin D and B (10 µM), nNIF (1 nM), CRISPP (1 nM), or CRISPP-SCR (1 nM). Following pre-incubation, PMNs were incubated with $6\times10^6$ *E. coli* bioparticles (MOLECULAR PROBES®) on a rotator for 4 hours at 37° C. in 5% $CO_2$/95% air. The PMNs were then washed and resuspended in the starting volume of M-199 before being spun down onto glass coverslips and fixed with 2% p-FA for 10 minutes and permeabilized with 0.1% Triton-X-100 for 10 minutes. Leukocytes were stained with WGA 555 (INVITROGEN™) and TO-PRO®-3 (MOLECULAR PROBES®), and randomly selected high-power visual field images were captured using confocal microscopy. IMAGEJ™ software (NIH) was used to determine the percentage of PMNs that were positive for fluorescently labeled *E. coli* bioparticles detected at 488 nm.

Example 19—Reactive Oxygen Species Generation

Human PMNs isolated from healthy adult whole blood were resuspended to a concentration of $2\times10^6$ cells/mL in M-199 media and pre-incubated±CRISPP (1 nM) or CRISPP-SCR (1 nM) peptide for 1 hour at 37° C. in 5% $CO_2$/95% air. The PMNs were then stimulated with LPS (100 ng/mL) for 1 hour, washed, and resuspended with a dihydrorhodamine (7.25 mM; MOLECULAR PROBES®) and catalase (1000 Units/mL; SIGMA-ALDRICH®) mixture and incubated at 37° C. for 10 minutes. After incubation, samples were placed at 4° C. and analyzed for ROS-dependent fluorescence using flow cytometry as performed in the University of Utah core facility (BECTON DICKINSON™, CELLQUEST™ software).

Example 20—Platelet Activation Assays

P-selectin translocation and surface display by activated platelets (see van Velzen J F, et al., *Thromb Res.* 2012; 130 (1):92-8) and formation of platelet-neutrophil aggregates (see Evangelista V, et al., *Blood.* 1996; 88 (11):4183-94) were measured as described.

Example 21—Nuclear Decondensation Assay

PMNs were isolated and resuspended to $2\times10^6$ cells/mL in M-199 media, pre-incubated with nNIF (1 nM), CRISPP (1 nM), nNIF-SCR (1 nM), CRISPP-SCR (1 nM), or the PAD4 inhibitor Cl-amidine (10 µM) for 1 hour at 37° C. in 5% $CO_2$/95% air, and treated ±PMA (20 nM) on poly-L-lysine coated glass coverslips for 2 hours. Nuclear decondensation was identified as described (see Papayannopoulos V, et al., *J Cell Biol.* 2010; 191 (3):677-91). Five randomly selected high-power visual fields per sample were captured via confocal microscopy and analyzed for nuclear area using the cell-permeable, fluorescent DNA dye SYTO® Green. The nuclear pixel areas of >100 individual cells per high-power field were determined using IMAGEJ™ software (NIH).

Example 22—PAD4 Activity Assay nNIF inhibition of PAD4 activity was determined using a PAD4 inhibitor screening assay kit (CAYMAN™). Briefly, nNIF (1 nM) was incubated with recombinant PAD4 and PAD4 enzyme substrate (2 mM) in PAD4 assay reagent for 30 minutes at 37° C. The PAD4 inhibitor, Cl-amidine (10 µM), was used as a positive control for PAD4 inhibition. The reaction was stopped with PAD4 Stop Solution and detected using an included ammonia detector assay. Ammonia detector fluorescence was measured at 470 nm following excitation at 405 nm on a SPECTRAMAX™ M5 fluorescence plate reader (MOLECULAR DEVICES™).

Example 23—Histone H3 Citrullination Determination

Adult PMNs were stimulated with PMA (20 nM) for 15 minutes at 37° C. in 5% $CO_2$/95% air following a 15 minute preincubation with nNIF, CRISPP, nNIF-SCR, or CRISPP-SCR (1 nM) or with Cl-amidine (10 µM), spun onto poly-L-lysine coated slides, and examined by immunocytochemistry with a primary antibody used to detect human citrullinated histone H3 (ABCAM™). Imaging was accomplished via confocal microscopy using a FV1000 IX81 confocal microscope and FLUOVIEW™ software (OLYMPUS™). Semi-quantitation was accomplished using IMAGEJ™ software (NIH) to determine the average citrullinated histone H3 content per cell.

Example 24—CRISPP Peptide Cellular Localization

FLAG-tagged CRISPP (F-CRISPP) and FLAG-tagged CRISPP-SCR (F—CRISPP-SCR) peptides were synthesized by the University of Utah's core facility and detected using immunocytochemistry. Adult neutrophils were preincubated with either F-CRISPP (1 nM) or F—CRISPP-SCR (1 nM) for 1 hour at 37° C. in 5% $CO_2$/95% air followed by stimulation with LPS (100 ng/mL) for 2 hours. The PMNs were then spun down onto glass coverslips with 2% p-FA fixation and 0.1% Triton X-100 permeabilization. FLAG-tagged peptide was detected using a monoclonal anti-FLAG antibody (SIGMA-ALDRICH®) with TO-PRO®-3 as a nuclear counterstain.

Example 25—Mouse Models of *E. coli* and LPS-Induced Peritonitis

C57/BL6 or Swiss-Webster mice were pretreated in blinded fashion with CRISPP (10 mg/kg), nNIF (10 mg/kg), or CRISPP-SCR (10 mg/kg) by i.p. injection 1 hour prior to infection (*E. coli*, $4.5 \times 10^7$ cfu/mouse, i.p.) or inoculation (LPS, 25 mg/kg, i.p.) (SIGMA-ALDRICH®). Control mice were injected with saline alone. The mice were sacrificed in a $CO_2$ chamber 3 hours post-infection/inoculation, and the peritoneal fluid and membrane samples were harvested. Briefly, the abdomen was disinfected and opened in the midline without injuring the muscle. The peritoneal cavity was lavaged with sterile saline solution (1 mL) and analyzed for in vivo NET formation, bacteriology, and leukocyte accumulation. NETs in the peritoneal fluid were qualitatively and quantitatively analyzed using live cell imaging with confocal microscopy and NET-associated histone H3 release assays. NETs on the serosal surface of the peritoneal membrane were assessed quantitatively using live cell imaging, followed by standardized grid analysis of five randomly selected high-power visual fields per tissue sample (IMAGEJ™ software, NIH). Peritoneal bacterial colony forming unit (cfu) counts were quantified by permeabilizing all recovered leukocytes with 0.1% Triton X-100 for 10 minutes and performing serial dilutions and bacterial cultures on 5% sheep blood agar plates (HARDY DIAGNOSTICS™). After a 24-hour incubation, bacterial counts were determined. Total leukocyte counts in the peritoneal lavage were determined in Neubauer chambers using an optical microscope after dilution in Turk's solution (2% acetic acid). Differential leukocyte analysis was performed using a 60× oil immersion objective to assess morphology of cytocentrifuged cells stained with May-Gruenwald-Giemsa dye. All mice were included in the final analysis.

Example 26—Mouse Model of Systemic Inflammation Induced by LPS ("Endotoxemia")

C57/BL6 mice were pretreated in blinded fashion with CRISPP (10 mg/kg), nNIF (10 mg/kg), or CRISPP-SCR (10 mg/kg) by i.p. injection 1 hour prior to and 6 hours after inoculation with LPS (25 mg/kg, i.p. injection). Control mice were i.p. injected with saline alone. Fluid resuscitation and antibiotic treatment were not used in these experiments. Survival was assessed over 50 or 72 hour intervals. All mice were included in the final survival analysis.

Example 27—Mouse Model of Polymicrobial Sepsis Using Cecal Ligation and Puncture (CLP)

C57BL/6 mice were anaesthetized with ketamine/xylazine (100 mg/kg and 10 mg/kg, i.p; respectively), and cecal ligation and puncture (CLP) was performed as previously described (see Araujo C V, et al., *Shock*. 2016; 45 (4):393-403). nNIF (10 mg/kg) or nNIF-SCR (10 mg/kg) i.p. was given 1 hour prior to and 6 hours after CLP surgery. The animals received subcutaneous sterile isotonic saline (1 mL) for fluid resuscitation immediately after the surgery. Sham-operated mice were subjected to identical procedures except that CLP was not done. 24 hours after CLP, all animals were scored for clinical illness severity as previously described (see Araujo C V, et al., *Shock*. 2016; 45 (4):393-403). In this assessment, higher scores reflect increased illness severity. Survival of mice in the nNIF/CLP (n=7), nNIF-SCR/CLP (n=8), nNIF/sham surgery (n=3), or nNIF-SCR/sham surgery (n=3) groups was followed for 5 days after the surgical procedure.

Example 28—Neutrophil Elastase Activity Assay

Synthetic fluorogenic substrate of NE, (MeOSuc)-AAPV-(pNA) (160 µM), was incubated with bioactive NE (500 nM)±the NE inhibitor, sivelestat (160 µM) or nNIF (50 nM), for 3 hours at 37° C. The reactions were quenched with 5% glacial acetic acid and centrifuged at 14,000 rpm for 5 minutes. Chromatograms were obtained using an AGILENT™ 1100 Series HPLC and a PHENOMENEX® 5 µm C18 LUNA® column (100 Å, 4.6×150 mm) over a 30 minute 10% to 90% B gradient (Buffer A 0.1% TFA in $H_2O$, Buffer B 0.1% TFA in ACN). Mass spectra were obtained for secondary validation of the reaction products using an API® 3500 triple quadrupole mass spectrometer. Chromatograms were offset on both the X and Y axes (by 0.5 minutes and 0.1 $A_{214}$, respectively) for greater visibility. Relative $A_{214}$ was determined by normalizing all of the data to the tallest HPLC peak displayed in each graph.

Example 29—Statistics

GRAPHPAD PRISM™ statistical software (version 5) was used to analyze results. The mean±standard error of the mean (SEM) was determined for each experimental variable. A Student t-test was used in FIGS. 2B, 6C, and 7B.

ANOVA was used to identify differences that existed among multiple experimental groups. If significant differences were found, a Tukey's post hoc test (FIGS. 1A, 1D, 2E, 3A-3C, 3E, 6B-6F, 7C, 7D, 8A, 8E, and 8F), a Bonferroni's multiple comparison test (FIG. 6A), or the Newman-Keuls post-hoc procedure (FIGS. 8C and 9B) was used to determine the groups with significant differences. A single tailed Mann-Whitney statistical tool was used for FIG. 8D. For FIGS. 9A and 9C, the Log-rank (Mantel-Cox) statistical tool was used to compare the survival curves between groups, and the post hoc Bonferroni correction was employed. All the data used in each statistical test met the assumption of the specific test and were normally distributed. All P values of <0.05 were considered as statistically significant.

Example 30—Study Approval

The University of Utah Institutional Review Board approved this study (IRB # s: 0392, 11919, and 39621), and all human subjects provided informed consent in accordance with the Declaration of Helsinki. All murine experiments were approved by the University of Utah Institutional Animal Care and Use Committee (#12-11017) and performed in a facility approved by the American Association of Laboratory Animal Care.

Example 31—Placental HTRA1 Protease Cleaves Alpha-1-Antitrypsin and Generates Neonatal NET-Inhibitory Factor Without being bound by any specific theory, it was hypothesized that placentally expressed HTRA1, a serine protease, regulates the formation of NET-inhibitory peptides through cleavage of AAT. To test this hypothesis, term and preterm placenta were assessed for HTRA1 expression via western blotting. HTRA1 and AAT plasma expression from term and preterm infants and adults were determined by ELISA. Bioactive (0.5 µg) or placental eluted HTRA1 was incubated with AAT (8 µM) for 18 hours at 37° C. Carboxy-terminus fragments of AAT were detected using western blotting and mass spectrometry. The reaction products were incubated for 1 hour with PMNs isolated from healthy adults prior to LPS stimulation (100 ng/mL) and assessed for NET formation using live cell imaging. Reactive oxygen species were assessed using flow cytometry, chemotaxis using a modified Boyden chamber assay, and bacterial killing using *E. coli*.

Term and preterm infant placentas expressed HTRA1, with significantly higher levels of HTRA1 in plasma from term (465.1±71.8 µg/mL) and preterm (385.9±71.3 µg/mL) infant cord blood compared to adults (58.6±11.6 µg/mL). Bioactive and placental-derived HTRA1 incubated with AAT generated a 4 kD AAT fragment. Furthermore, pre-incubation of this fragment with LPS-stimulated PMNs inhibited NET formation. The cleavage fragment from HTRA1-AAT had no effect on reactive oxygen species generation, chemotaxis, or phagocytosis. However, incubation of this fragment with LPS-stimulated PMNs significantly reduced NET-associated bacterial killing compared to a scrambled HTRA1-AAT fragment.

HTRA1 expressed in the placenta interacts with AAT to generate a carboxy-terminus cleavage fragment with identical NET-inhibitory properties to nNIF. Accordingly, placental HTRA1 may generate nNIF in the fetal circulation as a mechanism of tolerance during gestation.

It will be obvious to those having skill in the art that many changes may be made to the details of the above-described embodiments without departing from the underlying principles of the invention. The scope of the present invention should, therefore, be determined only by the following claims.

The invention claimed is:

1. A method of inhibiting development, growth, or spread of a cancer having NET formation in a patient, the method comprising:
administering to the patient an effective amount of a pharmaceutical composition comprising a peptide consisting of the amino acid sequence of SEQ ID NO:1 or SEQ ID NO:2 and a pharmaceutically acceptable carrier, to reduce a pathological effect or symptom of the cancer, to reduce the risk of developing the cancer, or to reduce a risk of metastasis.

2. The method of claim 1, wherein the cancer is at least one of melanoma, ovarian cancer, stomach cancer, or lung cancer.

3. The method of claim 1, wherein the pharmaceutical composition substantially inhibits neutrophil extracellular trap (NET) formation.

4. The method of claim 1, wherein the patient is mammal.

5. The method of claim 1, wherein the cancer is at least one of melanoma, ovarian cancer, stomach cancer, or lung cancer.

6. The method of claim 1, wherein the pharmaceutical composition substantially inhibits neutrophil extracellular trap (NET) formation.

7. A method of diagnosing a patient having cancer who would benefit from treatment with a NET-Inhibitory Peptide (NIP), the method comprising:
obtaining a sample from the patient;
detecting whether NET formation is present in the sample; and
diagnosing the patient as a patient who would benefit from treatment with a peptide consisting of the amino acid sequence of SEQ ID NO:1 or SEQ ID NO:2 when the presence of NET formation in the sample is detected.

8. The method of claim 7, wherein the sample is cancerous cells or cancerous cells including their microenvironment.

9. The method of claim 8, wherein the cancerous cells include at least one of melanocytes, ovarian cells, stomach cells, or lung cells.

10. The method of claim 7 further comprising after the detecting step,
administering an effective amount of a pharmaceutical composition comprising a peptide consisting of the amino acid sequence of SEQ ID NO:1 or SEQ ID NO:2 and a pharmaceutically acceptable carrier to the diagnosed patient and thereby treating a patient having cancer who would benefit from treating with a NIP.

11. The method of claim 10, wherein the cancerous cells include at least one of melanocytes, ovarian cells, stomach cells, or lung cells.

12. The method of claim 10, wherein the pharmaceutical composition substantially inhibits NET formation.

13. The method of claim 10, wherein the patient is mammal.

14. The method of claim 4 or claim 13, wherein the mammal is human.

15. The method of claim 1, wherein the pathological effect of the cancer is thrombosis.

* * * * *